US012788581B2

(12) United States Patent
Beach et al.

(10) Patent No.: US 12,788,581 B2
(45) Date of Patent: Nov. 10, 2026

(54) EXPANDABLE INTERBODY

(71) Applicant: Alphatec Spine, Inc., Carlsbad, CA (US)

(72) Inventors: Jared Beach, Del Mar, CA (US); Thomas Hackathorn, Vista, CA (US); Tyler Hammann, Encinitas, CA (US)

(73) Assignee: Alphatec Spine, Inc., Carlsbad, CA (US)

(*) Notice: Subject to any disclaimer, the term of this patent is extended or adjusted under 35 U.S.C. 154(b) by 0 days.

(21) Appl. No.: 19/315,305

(22) Filed: Aug. 29, 2025

(65) Prior Publication Data

US 2026/0060813 A1 Mar. 5, 2026

Related U.S. Application Data

(60) Provisional application No. 63/689,624, filed on Aug. 30, 2024.

(51) Int. Cl.
*A61F 2/44* (2006.01)
*A61F 2/30* (2006.01)

(52) U.S. Cl.
CPC .... *A61F 2/447* (2013.01); *A61F 2002/30148* (2013.01); *A61F 2002/30326* (2013.01); *A61F 2002/30401* (2013.01); *A61F 2002/30405* (2013.01); *A61F 2002/30429* (2013.01); *A61F 2002/30476* (2013.01); *A61F 2002/30538* (2013.01); *A61F 2002/30553* (2013.01);
(Continued)

(58) Field of Classification Search
CPC .. A61F 2002/30405; A61F 2002/30556; A61F 2002/30411; A61F 2/4455; A61F 2/4611; A61F 2/447
See application file for complete search history.

(56) References Cited

U.S. PATENT DOCUMENTS

| | | | | |
|---|---|---|---|---|
| 10,105,238 | B2 | 10/2018 | Koch et al. | |
| 11,357,640 | B2 * | 6/2022 | Weiman | A61F 2/4425 |
| 11,826,260 | B2 | 11/2023 | Valkoun et al. | |

(Continued)

FOREIGN PATENT DOCUMENTS

| | | | | |
|---|---|---|---|---|
| EP | 3340938 B1 * | 7/2024 | | A61F 2/44 |
| EP | 3818964 B1 * | 7/2024 | | A61F 2/447 |
| WO | WO-2014164625 A1 * | 10/2014 | | A61F 2/447 |

OTHER PUBLICATIONS

International Searching Authority, "International Search Report and Written Opinion," for PCT Application No. PCT/US2025/044138, Dec. 11, 2025.

*Primary Examiner* — Jacqueline T Johanas
(74) *Attorney, Agent, or Firm* — Dentons Durham Jones Pinegar; Sarah W. Matthews

(57) ABSTRACT

In various aspects, an expandable implant for use in a surgical procedure includes a distal cage, a proximal cage mechanically connectable with the distal cage, a top expandable assembly, and a bottom expandable assembly. Each of the top and bottom expandable assemblies have a distal portion in communication with a surface of the distal cage and a proximal portion in communication with a surface of the proximal cage. The expandable implant is expandable firstly in a medial-lateral direction, secondly in a lordotic (e.g., angular) direction, and thirdly a cranial-caudal direction. Additionally, the expandable implant may be diagonally symmetrical about a longitudinal axis of the expandable implant.

22 Claims, 43 Drawing Sheets

(52) U.S. Cl.
CPC ............... *A61F 2002/30556* (2013.01); *A61F 2002/30622* (2013.01)

(56) References Cited

U.S. PATENT DOCUMENTS

| | | | | |
|---|---|---|---|---|
| 2014/0039622 | A1* | 2/2014 | Glerum | A61F 2/446 623/17.15 |
| 2018/0193164 | A1 | 7/2018 | Shoshtaev | |
| 2019/0117409 | A1* | 4/2019 | Shoshtaev | A61F 2/4425 |
| 2019/0269521 | A1 | 9/2019 | Shoshtaev | |
| 2019/0388232 | A1* | 12/2019 | Purcell | A61F 2/442 |
| 2020/0352731 | A1* | 11/2020 | Berry | A61F 2/447 |
| 2021/0137695 | A1* | 5/2021 | Huang | A61F 2/4455 |
| 2022/0008212 | A1 | 1/2022 | Weiman et al. | |
| 2022/0015923 | A1 | 1/2022 | Shoshtaev | |
| 2022/0125596 | A1* | 4/2022 | Valkoun | A61F 2/442 |
| 2022/0395379 | A1* | 12/2022 | Ries | A61F 2/44 |
| 2022/0395381 | A1* | 12/2022 | Valkoun | A61F 2/447 |
| 2023/0190490 | A1* | 6/2023 | Corrao, Jr. | A61F 2/447 623/17.11 |
| 2024/0299187 | A1* | 9/2024 | Hutton | A61F 2/447 |
| 2025/0120820 | A1* | 4/2025 | Valkoun | A61F 2/447 |
| 2025/0359999 | A1* | 11/2025 | Valkoun | A61F 2/4455 |
| 2026/0060813 | A1* | 3/2026 | Beach | A61F 2/447 |

* cited by examiner

EXPANDABLE INTERBODY

CROSS REFERENCE TO RELATED MATTER

This application claims priority to U.S. Provisional Application No. 63/689,624, filed Aug. 30, 2024, the entirety of which is incorporated herein by reference.

TECHNICAL FIELD

This disclosure relates generally to interbody implants used in surgical procedures that are expandable in multiple anatomical directions.

SUMMARY

Disclosed are systems, devices, and/or methods of use thereof concerning interbody implants used in surgical procedures that are expandable in multiple anatomical directions. In various aspects, an expandable implant for use in a surgical procedure includes a distal cage, a proximal cage opposite the distal cage, and a drive screw connecting the distal cage to the proximal cage. The expandable implant may also include a top distal pivot slidable along a top surface of the distal cage and a bottom distal pivot slidable along a bottom surface of the distal cage, the bottom surface opposite the top surface. Additionally, the expandable implant may include a top proximal pivot slidable along a top surface of the proximal cage and a bottom proximal pivot slidable along a bottom surface of the proximal cage, the bottom surface opposite the top surface. Further, the expandable implant may include a top pair of endplates, with each top endplate having a proximal end slidable along a surface of the top proximal pivot. The proximal end defines a proximal channel for slidably receiving a projection of the top proximal pivot. Each top endplate also has a distal end slidable along a surface of the top distal pivot, with the distal end defining a distal channel for slidably receiving a projection of the top distal pivot. A first endplate of the top pair of endplates may be connected to a hook portion of the bottom distal pivot when the expandable implant is in a collapsed state.

Still further, the expandable implant may include a bottom pair of endplates, with each endplate having a proximal end slidable along a surface of the bottom proximal pivot and the proximal end defining a proximal channel for slidably receiving a projection of the bottom proximal pivot. Each bottom endplate also has a distal end slidable along a surface of the bottom distal pivot, the distal end defining a distal channel for slidably receiving a projection of the bottom distal pivot. A first endplate of the bottom pair of endplates may be connected to a hook portion of the top distal pivot when the expandable implant is in the collapsed state. The expandable implant is expandable first in a medial-lateral direction, second in a lordotic (e.g., angular) direction, and third in a cranial-caudal direction.

In various aspects, an expandable implant for use in a surgical procedure includes a distal cage, a proximal cage opposite the distal cage, and a drive screw connecting the distal cage to the proximal cage. The expandable implant may also include a top expandable assembly having a distal portion in communication with a top surface of the distal cage and a proximal portion in communication with a top surface of the proximal cage. Additionally, the top expandable assembly includes a first top endplate having a distal end in connection with the distal portion and a proximal end in connection with the proximal portion, and a second top endplate adjacent to the first endplate, the second endplate having a distal end in connection with the distal portion and a proximal end in connection with the proximal portion.

The expandable implant may further include a bottom expandable assembly, where a distal portion of the bottom expandable assembly is in communication with a bottom surface of the distal cage and a proximal portion of the bottom expandable assembly is in communication with a bottom surface of the proximal cage. The bottom surface of the distal cage is opposite the top surface and the bottom surface of the proximal cage is opposite the top surface. The distal portion of the top expandable assembly includes a hook for mechanically connecting to a distal end of a first bottom endplate of the bottom expandable assembly. The distal portion of the bottom expandable assembly includes a hook for mechanically connecting to the distal end of the second top endplate of the top expandable assembly. The expandable implant is expandable firstly in a medial-lateral direction, secondly in a lordotic (e.g., angular) direction, and thirdly in a cranial-caudal direction.

In various aspects, an expandable implant for use in a surgical procedure includes a distal cage, a proximal cage in mechanical communication with the distal cage, a top distal ramp slidable along a top surface of the distal cage, and a bottom distal ramp slidable along a bottom surface of the distal cage, the bottom surface opposite the top surface. The top and bottom distal ramps facilitate expansion of the expandable interbody in a lordotic direction and a cranial-caudal direction. The expandable implant may also include a top proximal ramp slidable along a top surface of the proximal cage and a bottom proximal ramp slidable along a bottom surface of the proximal cage, the bottom surface opposite the top surface. The top and bottom proximal ramps facilitate expansion of the expandable interbody in the cranial-caudal direction.

Further, the expandable implant may include a plurality of endplates in mechanical connection with the top distal ramp, the bottom distal ramp, the top proximal ramp, and the bottom proximal ramp. The plurality of endplates may be expandable in a medial-lateral direction. The expandable interbody may be diagonally symmetrical about a longitudinal axis of the expandable interbody.

In various aspects, a method of expanding an expandable interbody includes first translating a distal cage proximally towards a proximal cage to a first position to cause a plurality of endplates to expand in a medial-lateral direction relative to a longitudinal axis of the expandable interbody. The method may also include second translating the distal cage proximally towards the proximal cage from the first position to a second position different than the first position, such that a locking hook of a top distal ramp clears a channel defined in a distal end of a first bottom endplate and a locking hook of a bottom distal ramp clears a channel defined in a distal end of a first top endplate. The second translating may cause: the top distal ramp to slide along the distal cage to achieve a desired lordosis; a first projection of the proximal cage to clear a channel defined in a proximal end of the first bottom endplate; and a second projection of the proximal cage to clear a channel defined in a proximal end of a second bottom endplate.

The method may additionally include third translating the distal cage proximally towards the proximal cage from the second position to a third position, a bore of the distal cage abutting a distal face of the proximal cage, the distal face of the proximal cage preventing further proximal translation of the distal cage. The third translating may cause a top proximal ramp to slide along the proximal cage in a cranial-caudal direction, such that a protrusion of the first bottom endplate slides within a groove defined in a proximal extension of a second top endplate, thereby allowing the first bottom endplate to vertically separate from the second top endplate.

Other aspects of the disclosed subject matter, as well as features and advantages of various aspects of the disclosed subject matter, should be apparent to those of ordinary skill in the art through consideration of the ensuing description, the accompanying drawings, and the appended claims.

DETAILED DESCRIPTION

Figure 1:
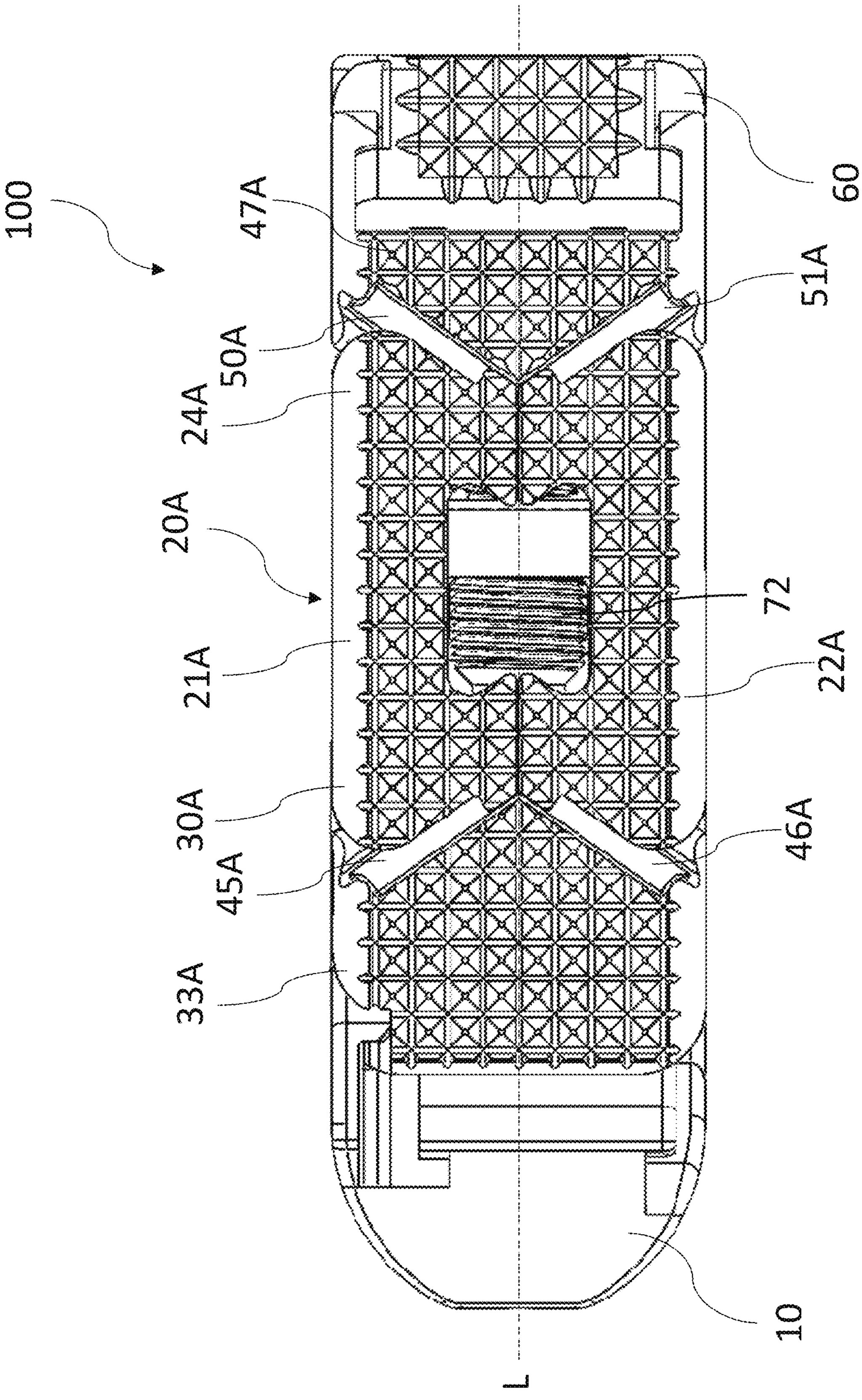
FIG. 1 illustrates a top or superior view of an expandable interbody implant in a fully collapsed configuration.
Figure 2A:
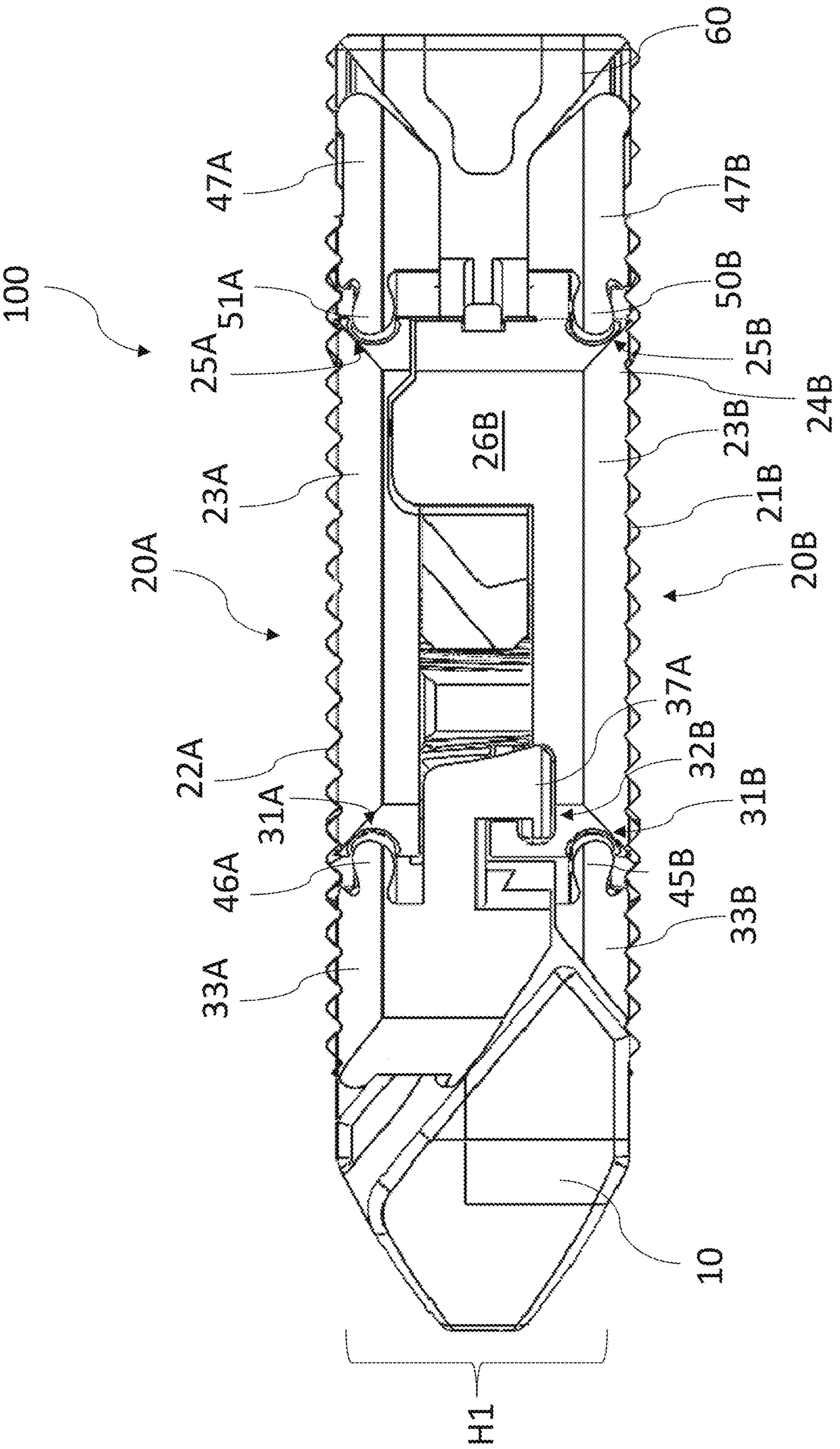
FIG. 2A illustrates a left-side view of the expandable interbody implant of FIG. 1 in the fully collapsed configuration and FIG. 2B illustrates a right-side view of the expandable interbody implant in the fully collapsed configuration.
Figure 2B:
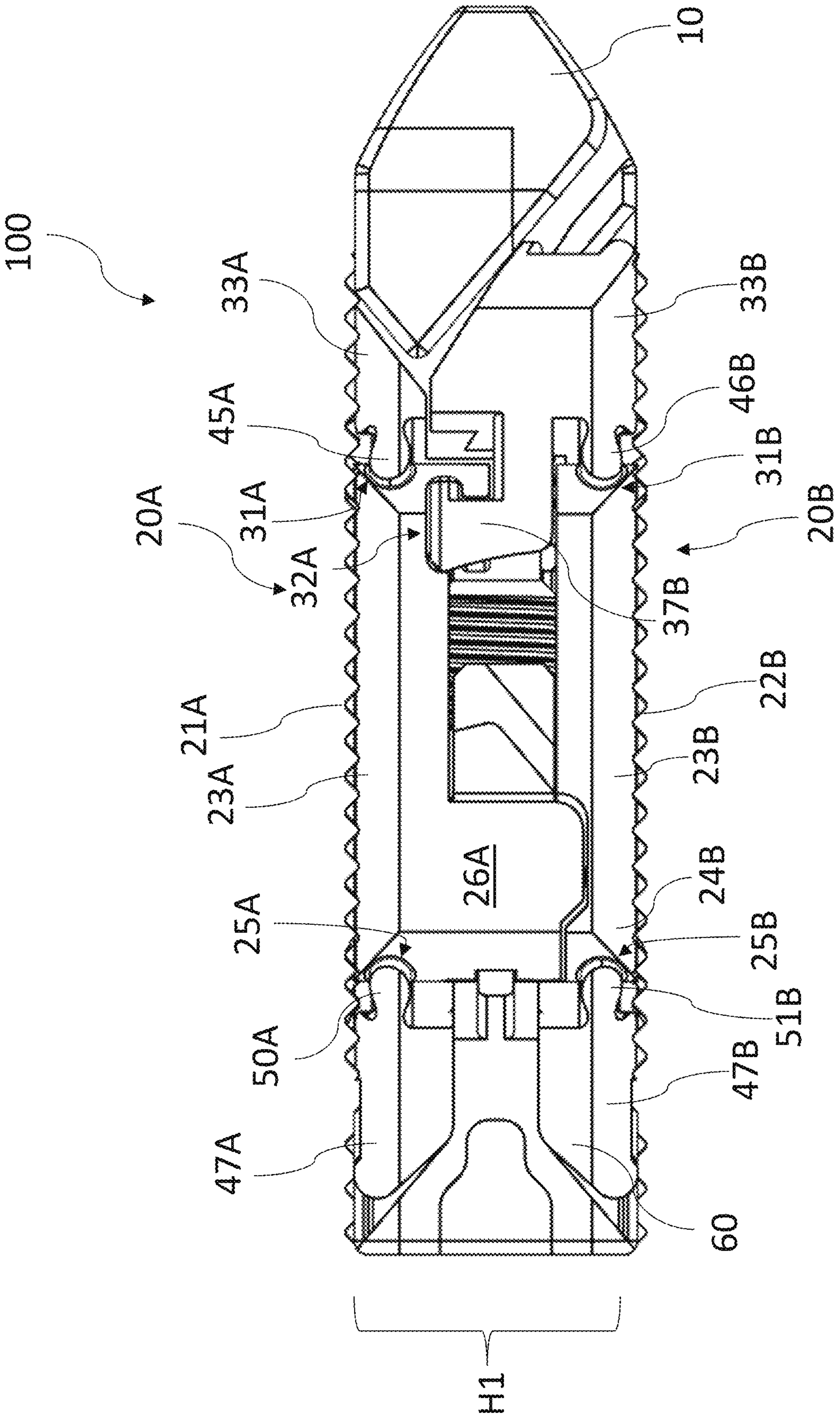

FIGS. 1 through 2B illustrate an expandable interbody implant 100 in a fully collapsed configuration. The expandable interbody implant 100 (also referred to herein as, "the implant 100" or "the interbody 100") includes a distal cage 10, a top expandable assembly 20A, a proximal cage 60, and a bottom expandable assembly 20B. The distal cage 10 is mechanically connectable to the proximal cage 60 through a dual-threaded drive screw 72. The bottom expandable assembly 20B is identical or substantially identical to the top expandable assembly 20A, and is diagonally symmetrical to the top expandable assembly 20A about a longitudinal axis L of the expandable interbody implant 100.

The expandable interbody implant 100 is expandable in at least three (3) directions. Firstly, the expandable interbody implant 100 is expandable in a medial-lateral direction or a planar direction to increase the width of the expandable interbody implant 100. Secondly, the expandable interbody implant 100 is expandable in a lordotic direction or an angular direction. Thirdly, the expandable interbody implant 100 is expandable in a cranial-caudal direction or a vertical direction to increase the height of the expandable interbody implant 100. Translation of the distal cage 10 towards the proximal cage 60 facilitates expansion of the expandable interbody implant 100 in each of the three directions. Additionally, each of the top expandable assembly 20A and the bottom expandable assembly 20B expand in the three directions.

The top expandable assembly 20A includes a first top endplate 21A, a second top endplate 22A adjacent to the first top endplate 21A in the collapsed configuration, a top distal pivot or ramp 33A and a top proximal pivot or ramp 47A. The top distal ramp 33A interfaces with and engages a surface (e.g., a top surface or other surface) of the distal cage 10. Likewise, the top proximal ramp 47A interfaces with and engages a surface (e.g., a top surface or other surface) of the proximal cage 60. Each of the first top endplate 21A and the second top endplate 22A have a body 23A extending between a proximal end 24A and a distal end 30A. The proximal end 24A interfaces and engages the top proximal pivot or ramp 47A and the distal end 30A interfaces and engages with the top distal pivot or ramp 33A. The proximal end 24A of the first top endplate 21A and the second top endplate 22A also includes a proximal extension 26A that interfaces and engages with a corresponding proximal extension 26B of the first bottom endplate 21B or the second bottom endplate 22B as discussed in more detail below.

For example, the proximal end 24A of both the first top endplate 21A and the second top endplate 22A defines a channel 25A for engaging a first projection 50A or a second projection 51A of the top proximal ramp 47A (FIGS. 2A and 2B). Similarly, the distal end 30A of both the first top endplate 21A and the second top endplate 22A defines a channel 31A for engaging a first projection 45A or a second projection 46A of the top distal ramp 33A.

Referring to FIGS. 2A and 2B, the bottom expandable assembly 20B is identical to the top expandable assembly 20A (but diagonally symmetrical) and includes all of the same components as the top expandable assembly 20A. That is, the bottom expandable assembly 20B includes a first bottom endplate 21B, a second bottom endplate 22B adjacent to the first bottom endplate 21B, a bottom distal pivot or ramp 33B and a bottom proximal pivot or ramp 47B. Because of the diagonal symmetry, the first bottom endplate 21B is identical or substantially identical to the second top endplate 22A, and the second bottom endplate 22B is identical or substantially identical to the first top endplate 21A. The bottom distal ramp 33B interfaces with and engages a surface (e.g., a bottom surface) of the distal cage 10. Likewise, the bottom proximal ramp 47B interfaces with and engages a surface (e.g., a bottom surface) of the proximal cage 60. Each of the first bottom endplate 21B and the second bottom endplate 22B have a body 23B extending between a proximal end 24B and a distal end 30B. The proximal end 24B interfaces and engages the bottom proximal pivot or ramp 47B and the distal end 30B interfaces and engages with the bottom distal pivot or ramp 33B.

Additionally, as with the top expandable assembly 20A, the proximal end 24B of both the first bottom endplate 21B and the bottom second endplate 22B defines a channel 25B for engaging a first projection 50B or a second projection 51B of the bottom proximal ramp 47B. Similarly, the distal end 30B of both the first bottom endplate 21B and the second bottom endplate 22B defines a channel 31B for engaging a first projection 45B or a second projection 46B of the bottom distal ramp 33B. The proximal end 24B of the first bottom endplate 21B and the second bottom endplate 22B also includes a proximal extension 26B (FIG. 4) that interfaces and engages with a corresponding proximal extension 26A of the first top endplate 21A or the second top endplate 22A.

A portion of the top distal ramp 33A of the top expandable assembly 20A is connected to the first bottom endplate 21B of the bottom expandable assembly 20B. Specifically, a hook portion 37A of the top distal ramp 33A is connected to and engaged by a channel 32B defined in the distal end 30B of the first bottom endplate 21B. Though not shown in FIG. 2, as the bottom expandable assembly 20B is identical to the top expandable assembly 20A, the bottom distal ramp 33B of the bottom expandable assembly 20B also includes a hook portion 37B that is connected to and engaged by a channel 32A defined in the distal end 30A of the first top endplate 21A.

The expandable interbody implant 100 is diagonally symmetrical about the longitudinal axis L of the expandable interbody implant 100. That is, the bottom expandable assembly 20B is identical or substantially identical to the top expandable assembly 20A rotated 180°. As such, the first top endplate 21A sits on top of and engages the second bottom endplate 22B. Likewise, the second top endplate 22A sits on top of and engages the first bottom endplate 21B.

Figure 3:
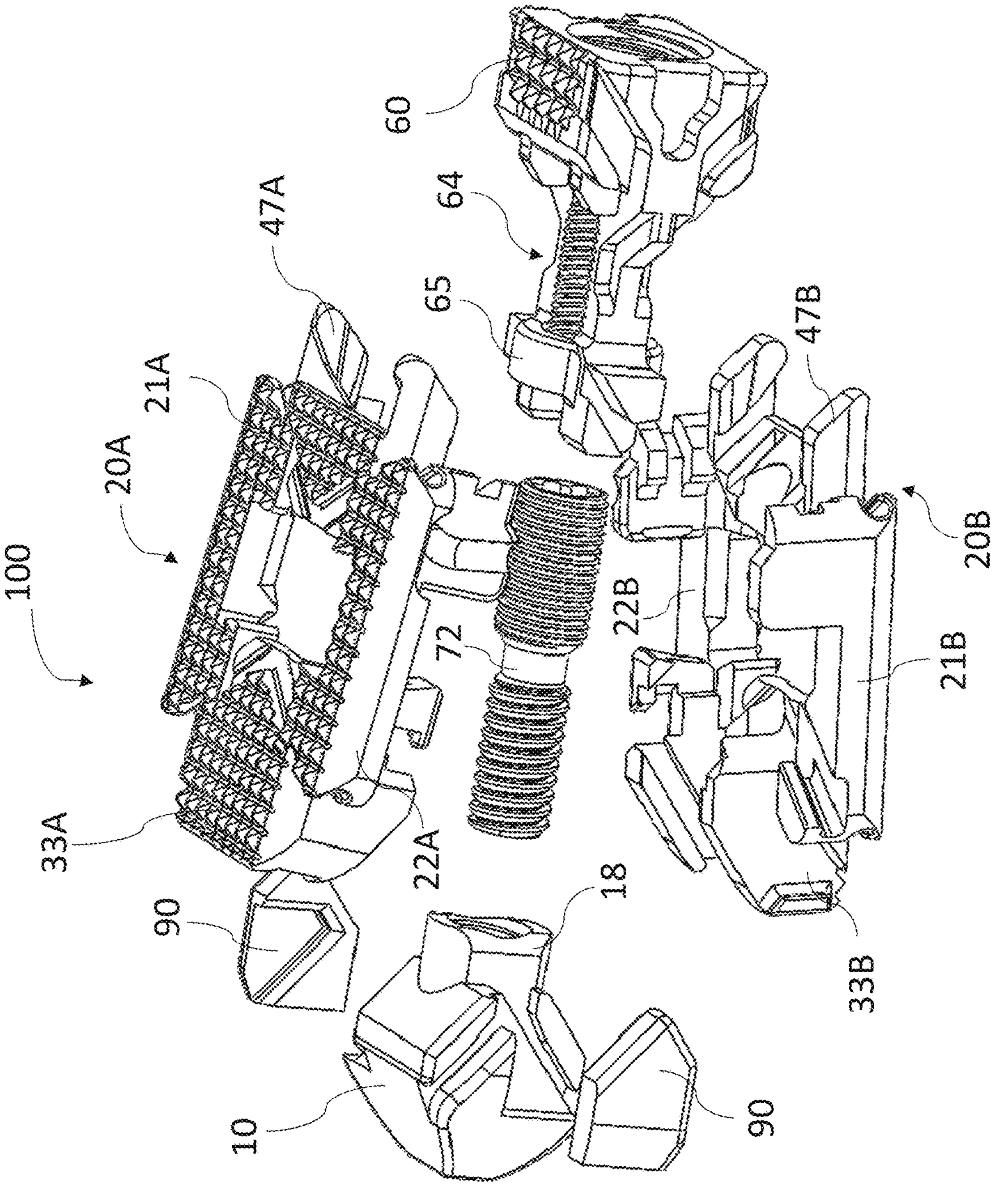
FIGS. 3 and 4 illustrate additional exploded views of the expandable interbody implant of FIGS. 1 through 2B.
Figure 4:
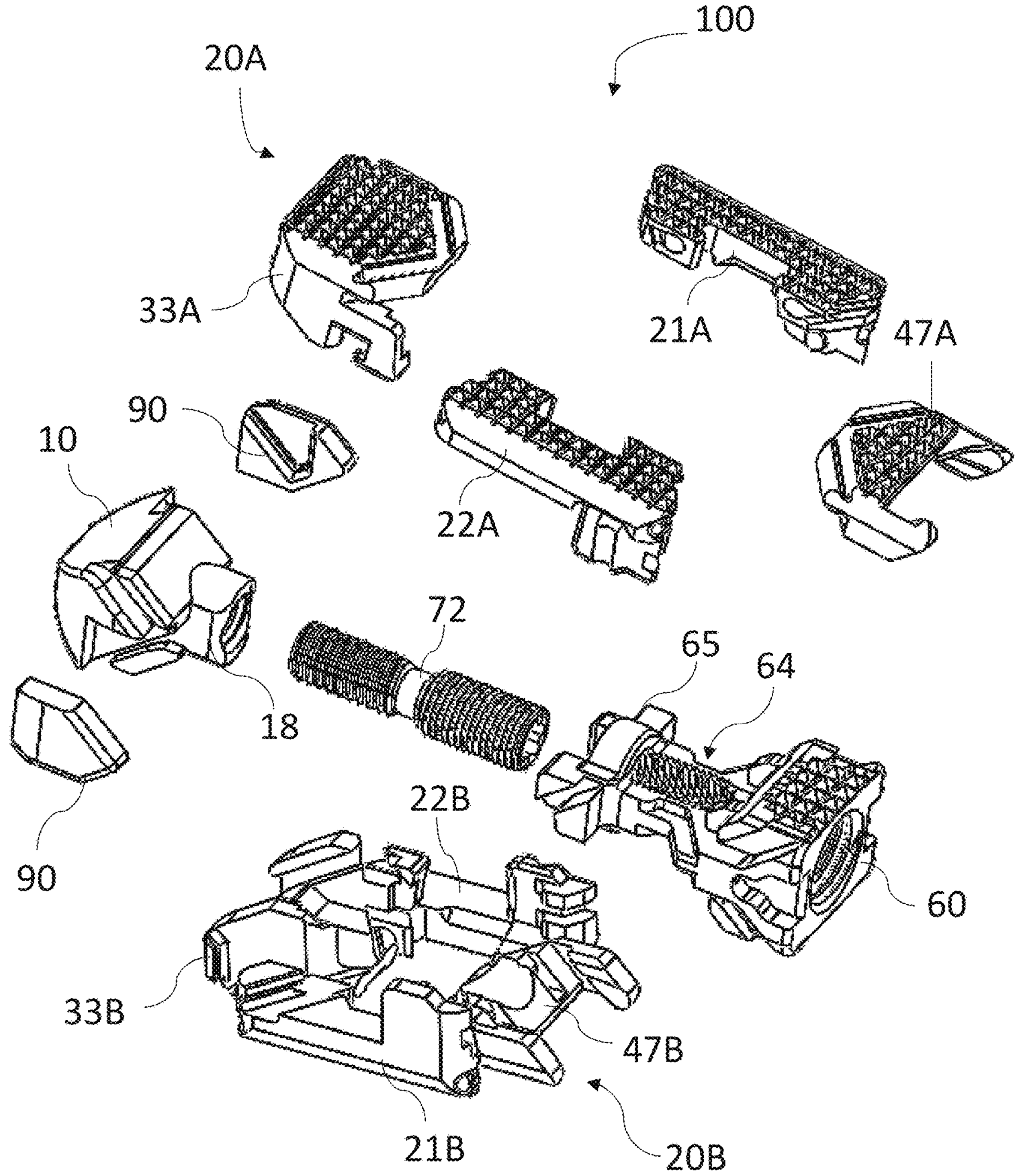

FIGS. 3 and 4 illustrate additional exploded views of the expandable interbody implant 100 of FIGS. 1 through 2B. As illustrated in FIG. 3, the distal cage 10 receives a cap 90 on each side of the body 11. Additionally, the drive screw 72 can be seen positioned between the proximal cage 60 and the distal cage 10. The drive screw 72 mechanically connects the proximal cage 60 and the distal cage 10.

FIGS. 5 through 9 illustrate the expandable interbody implant 100 of FIG. 1 in a first medial-lateral expanded configuration 102 to increase the width of the implant 100. Components from each of the top expandable assembly 20A and the bottom expandable assembly 20B expand in the medial-lateral direction. The distal cage 10 is driven or translated proximally towards the proximal cage 60 to a first position via action of the drive screw 72. Upon translation of the distal cage 10 proximally towards the proximal cage 60, the interbody 100 expands laterally, with the first top endplate 21A and second top endplate 22A moving outwardly and away from each other, and similarly the first bottom endplate 21B and second bottom endplate 22B move outwardly and away from each other. To enable this outward movement of the endplates, slots and channels are provided at the distal and proximal ends. In one configuration, four slots/channels are provided in each of the distal and proximal ends.

At the distal end, the projection 46A of the top distal ramp 33A slides within channel 31A of the second top endplate 22A at the distal end, and the projection 46B of the bottom distal ramp 33B slides within the channel 31B of the first bottom endplate 21B at the distal end. Similarly, the projection 45A of the top distal ramp 33A slides within channel 31A of the first top endplate 21A at the distal end, and the projection 45B of the bottom distal ramp 33B slides within the channel 31B of the second bottom endplate 22B. However, the top distal ramp 33A and the bottom distal ramp 33B experience substantially no movement or sliding relative to the distal cage 10. That is, the top distal ramp 33A and the bottom distal ramp 33B stay substantially static relative to the distal cage 10, with the first top endplate 21A, the second top endplate 22A, the first bottom endplate 21B, and the second bottom endplate 22B moving in the medial-lateral direction.

Figure 5:
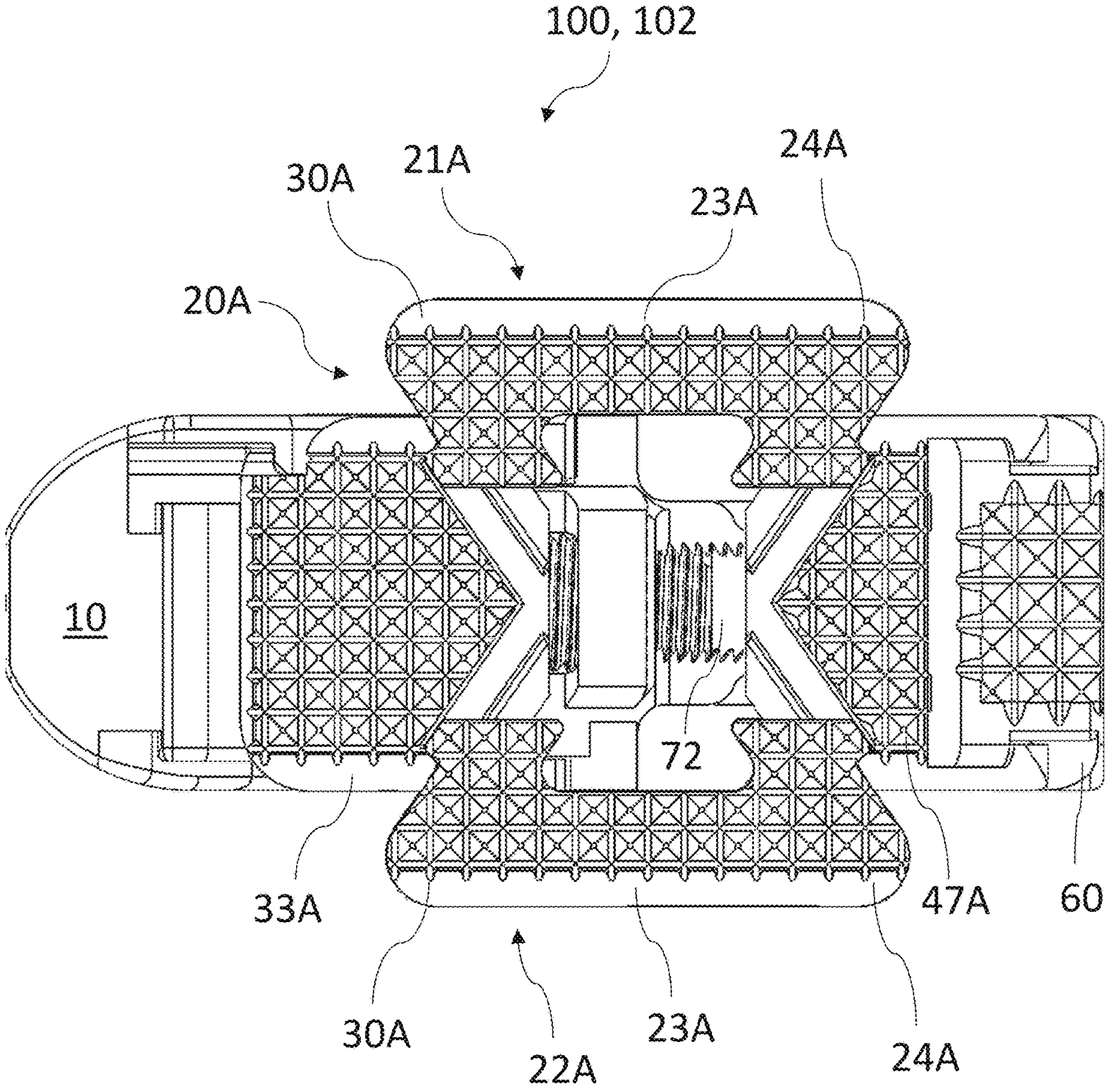
FIG. 5 illustrates a top view of the expandable interbody implant of FIG. 1 in a first medial-lateral expanded configuration.

At the proximal end, the proximal channel 25A at the proximal end 24A of the first top endplate 21A slides along the first projection 50A of the top proximal ramp 47A (see FIG. 5). Identically, the proximal channel 25A at the proximal end 24A of the second top endplate 22A slides along the second projection 51A of the top proximal ramp 47A (see FIG. 5). In this way, the first top endplate 21A and the second top endplate 22A may expand laterally away from a mid-line of the implant 100 and away from each other. However, the top proximal ramp 47A and the bottom proximal ramp 47B experience substantially no movement or sliding relative to the proximal cage 60. That is, the top proximal ramp 47A and the bottom proximal ramp 47B stay substantially static relative to the proximal cage 60, with the first top endplate 21A, the second top endplate 22A, the first bottom endplate 21B, and the second bottom endplate 22B moving in the medial-lateral direction.

Similarly, the proximal channel 25B at the proximal end 24B of the first bottom endplate 21B slides along the first projection 50B of the bottom proximal ramp 47B. Identically, the proximal channel 25B at the proximal end 24B of the second bottom endplate 22B slides along the second projection 51B of the top proximal ramp 47A (see FIG. 5) and the distal channel 31B in the distal end 30B of the second bottom endplate 22B slides along the second projection 46B of the bottom distal ramp 33B. In this way, the first bottom endplate 21B and the second bottom endplate 22B may expand laterally away from a mid-line of the implant 100 and away from each other.

Figure 6:
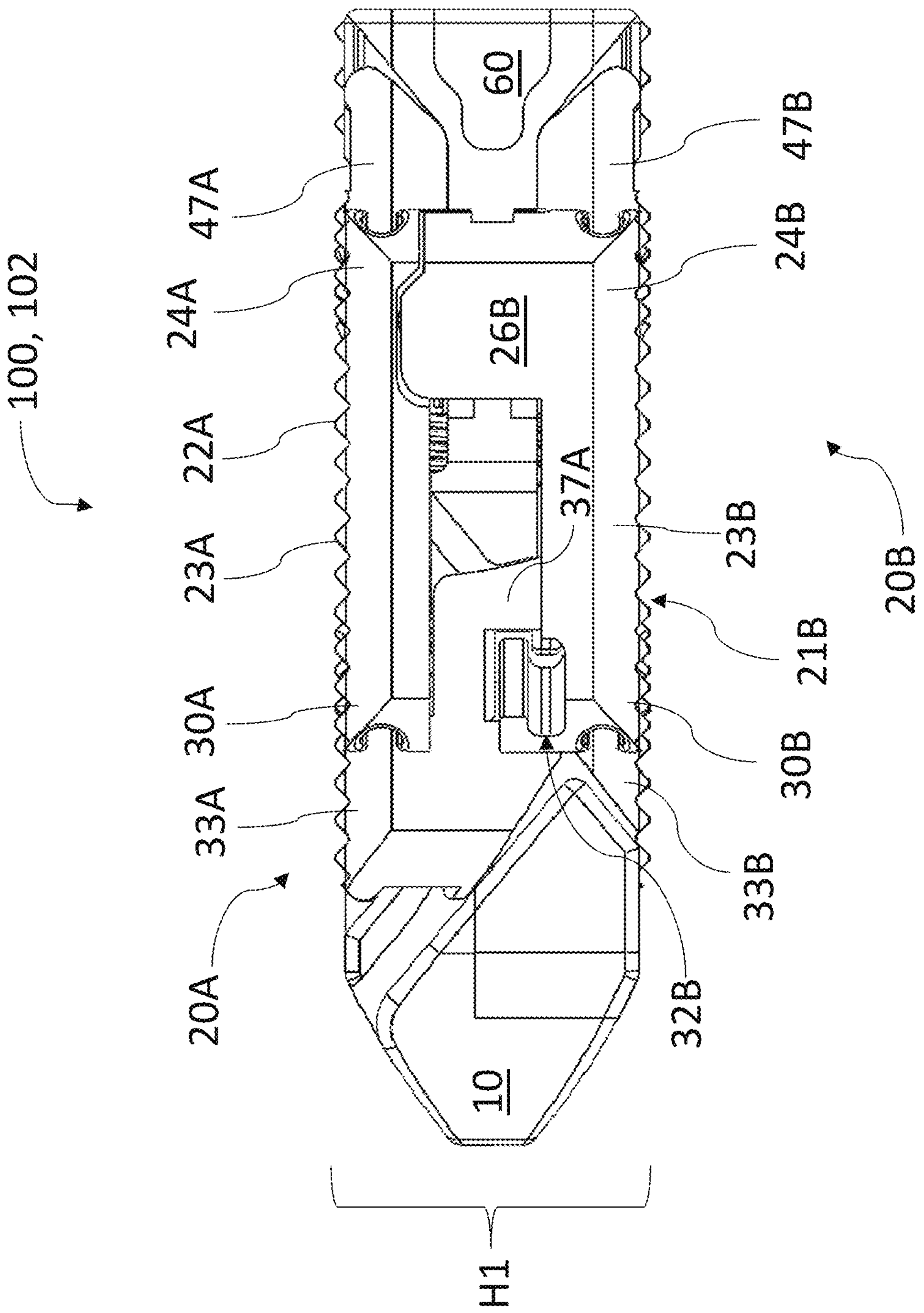
FIG. 6 illustrates a side view of the expandable interbody implant of the expandable interbody implant of FIG. 3 in the first medial-lateral expanded configuration.
Figure 7:
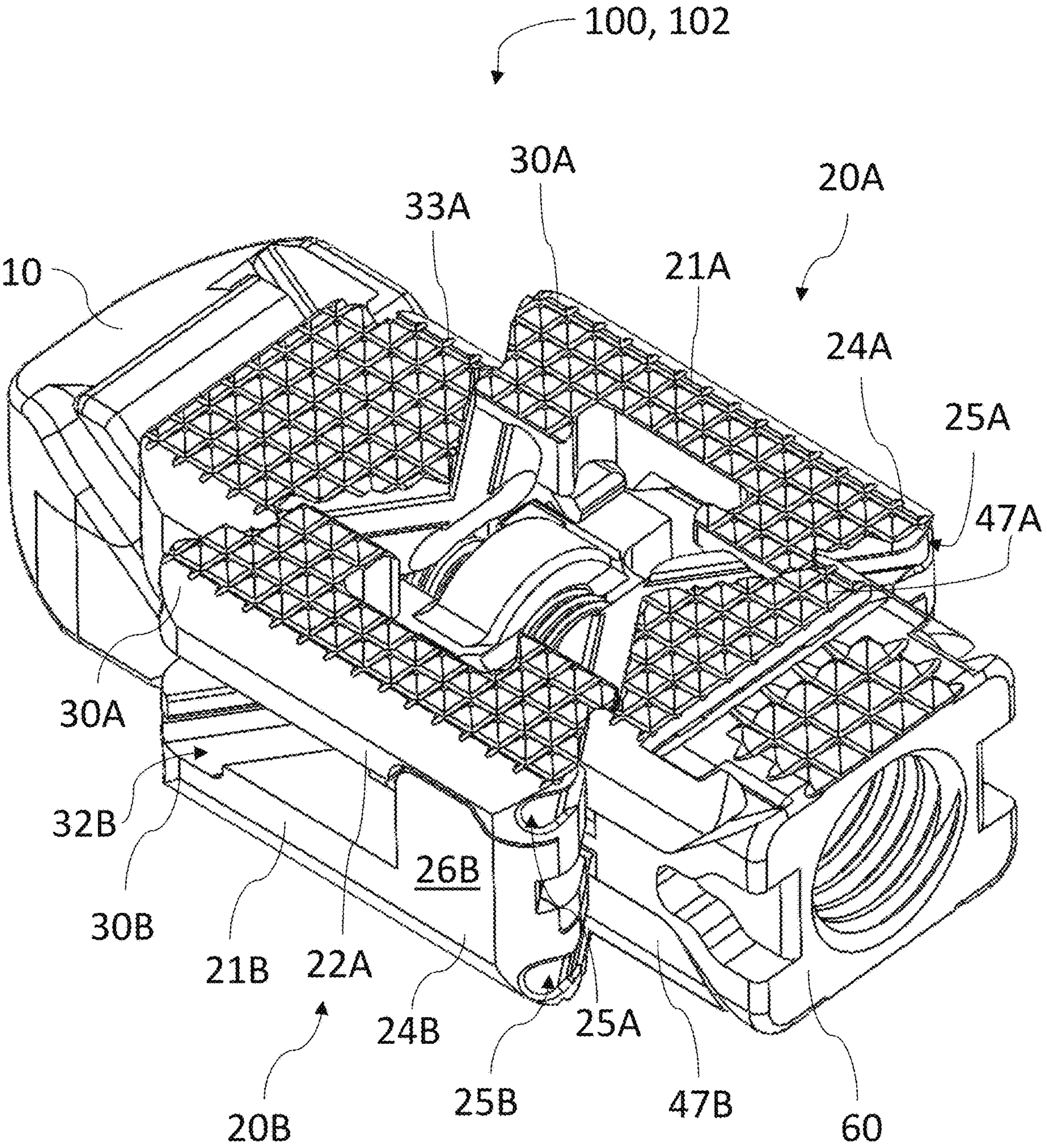
FIG. 7 illustrates a proximal, top, perspective view of the expandable interbody implant of FIG. 5 in the first medial-lateral expanded configuration.
Figure 8:
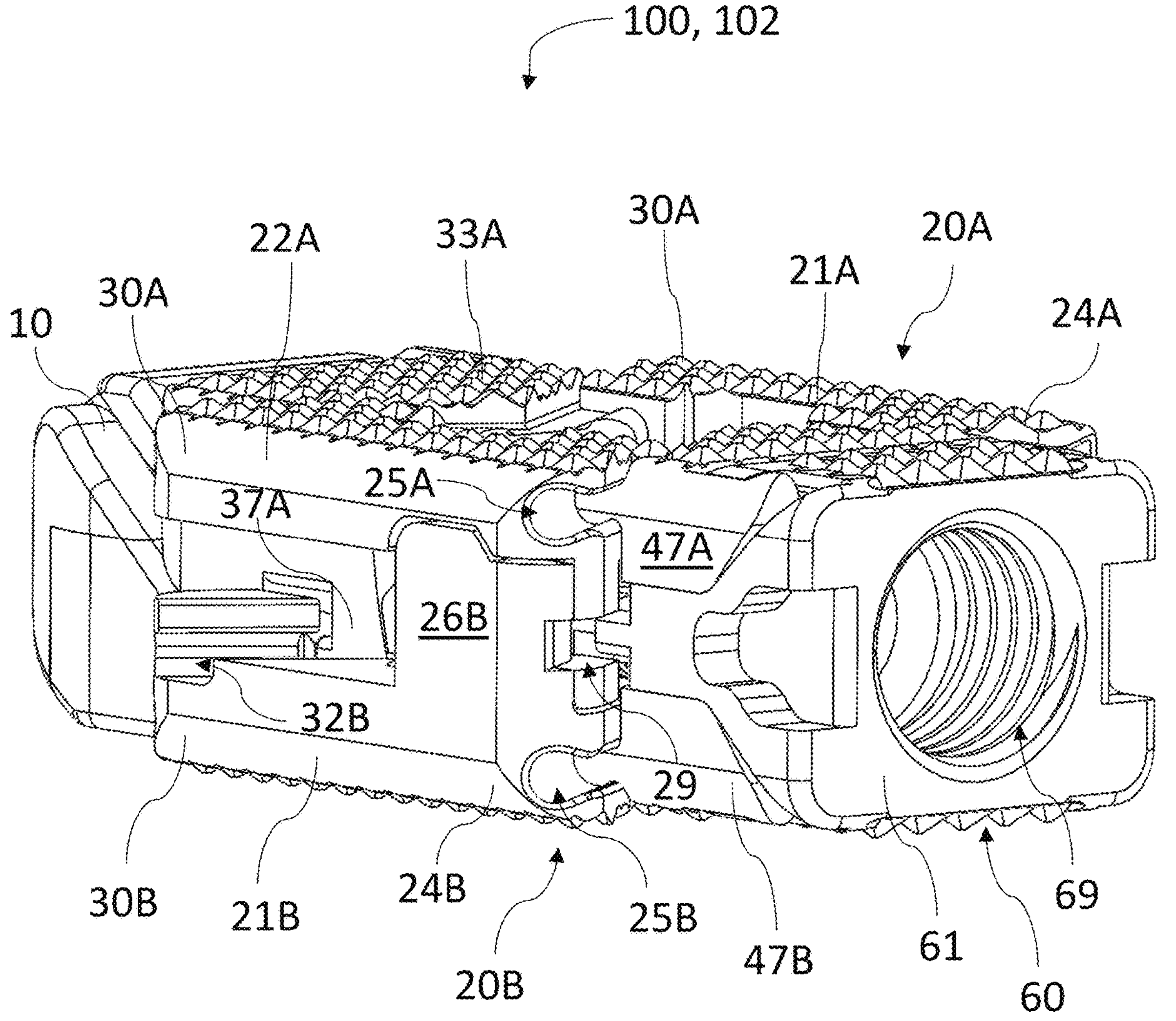
FIG. 8 illustrates a proximal end, perspective view of the expandable interbody implant of FIG. 5 in the first medial-lateral expanded configuration.
Figure 9:
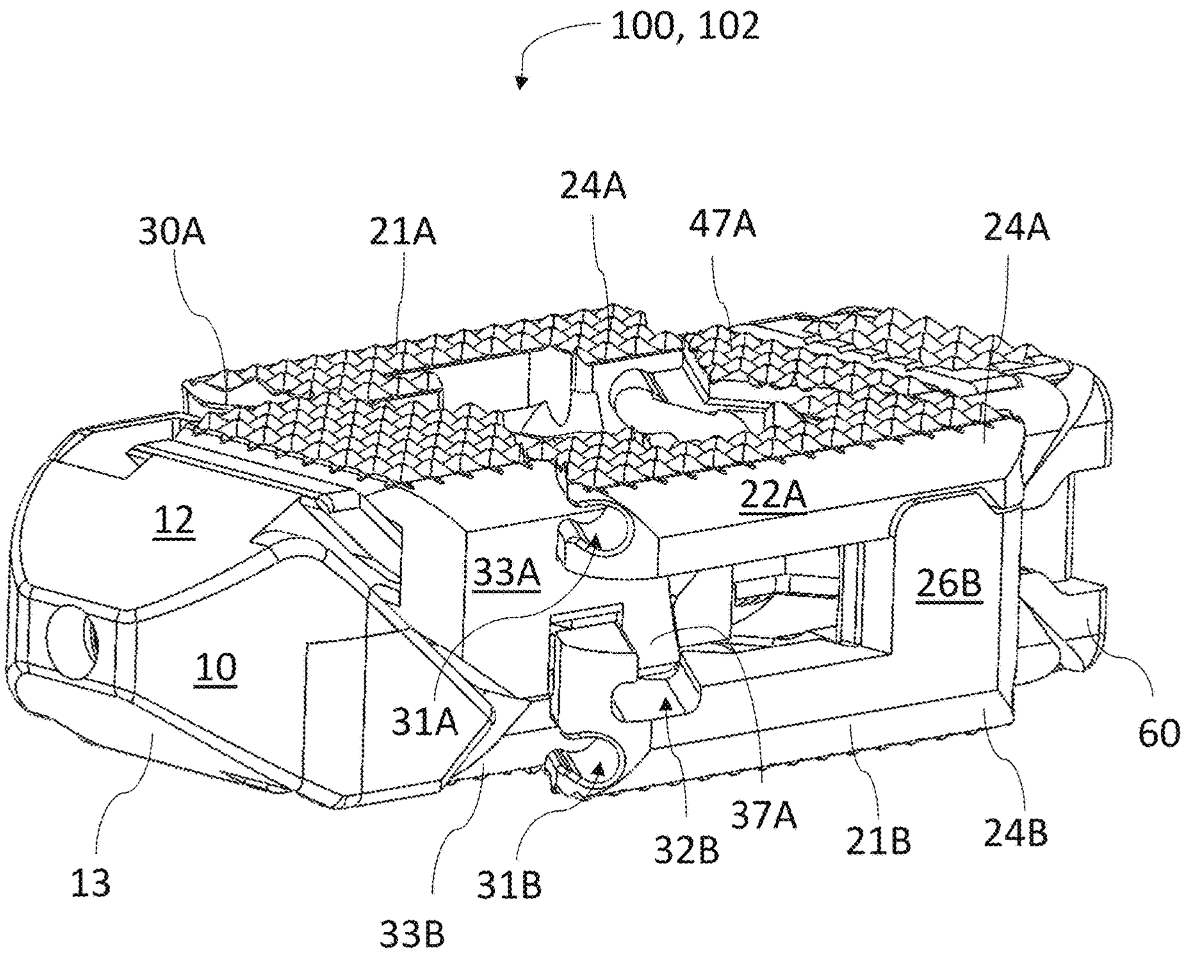
FIG. 9 illustrates distal end, perspective view of the expandable interbody implant of FIG. 5 in the first medial-lateral expanded configuration.

As seen in FIGS. 6, 8, and 9, when the first bottom endplate 21B expands in the medial-lateral direction, the hook portion 37A of the top distal ramp 33A clears the channel 32B in the distal end 30B of the first bottom endplate 21B. Similarly, when the first top endplate 21A expands in the medial-lateral direction, the hook portion 37B (visible in FIG. 2B) of the bottom distal ramp 33B clears the channel 32A in the distal end 30A of the first top endplate 21A. This clearance of the hook portions 37A, 37B allows for further expansion of the implant 100. In other words, the hook portions 37A, 37B, interact with the channels of the end plates to constrain movement of the endplates to the medial-lateral direction only until the hook portions 37A, 37B clear the channels.

Referring to FIG. 8, the proximal extension 26A (not visible in FIG. 8) of the second top endplate 22A is mechanically engaged with the proximal extension 26B of the first bottom endplate 21B. Together, the proximal extensions 26A and 26B define or create a cut-out 29 (see FIGS. 22A-22B) that engages a projection 61P of the proximal cage 60 (see FIGS. 18A and 18B). When the top expandable assembly 20A and the bottom expandable assembly 20B expand in the medial-lateral direction, the projection 61P begins to clear the cut-out 29, allowing for additional expansion in the second top endplate 22A and the first bottom endplate 21B. A similar relationship and cut-out 29 is formed between the first top endplate 21B and the second bottom endplate 22B.

Little to no vertical gain is realized in the medial-lateral expanded configuration. Accordingly, the implant 100 has a height H1 when the implant is expanded in the medial-lateral or first direction, which is substantially the same height as when the implant 100 is fully collapsed, as in FIGS. 1 through 2B. H1 may range from about 7 mm to about 9 mm, such as 7 mm, 7.5 mm, 8 mm, 8.5 mm, 9 mm, etc.

Figure 10:
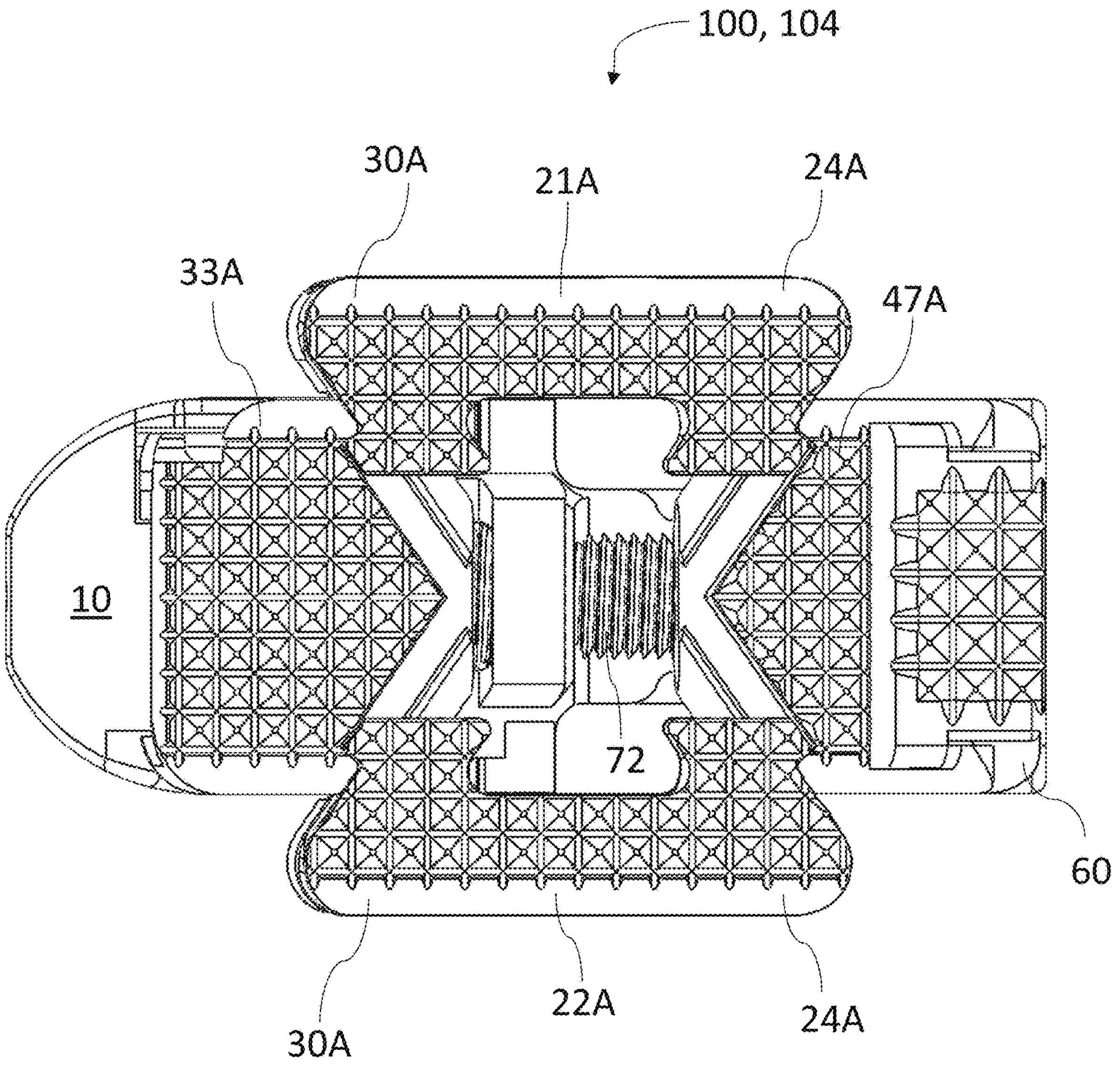
FIG. 10 illustrates a top view of the expandable interbody implant of FIG. 1 in a second lordotic or angular expanded configuration.
Figure 11:
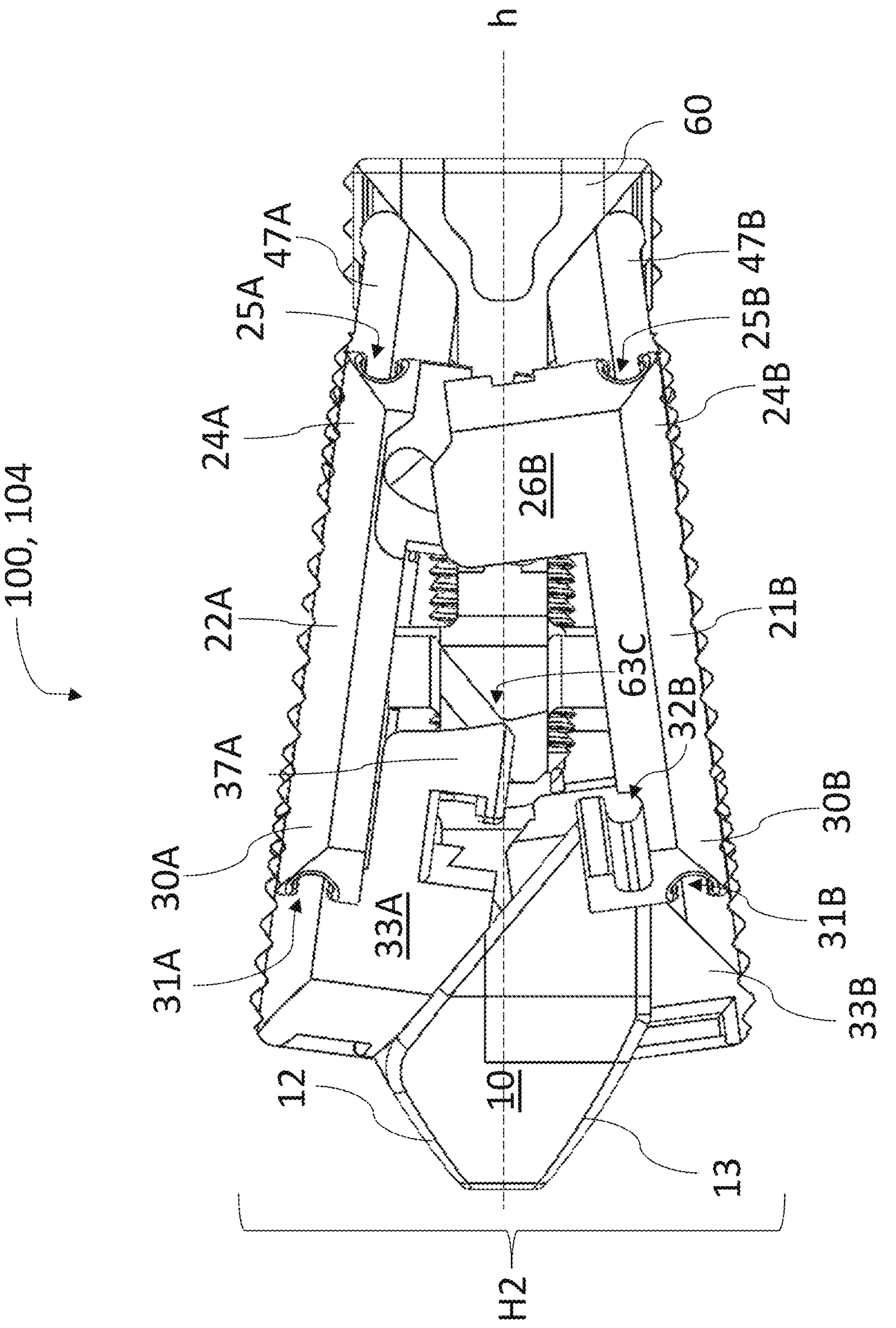
FIG. 11 illustrates a side view of the expandable interbody implant of FIG. 10 in the second lordotic or angular expanded configuration.

FIGS. 10 and 11 illustrate the expandable interbody implant 100 of FIG. 1 in a second lordotic or angular expanded configuration 104. As seen in FIG. 10, the medial-lateral expansion of the top expandable assembly 20A and the bottom expandable assembly 20B is maintained throughout the lordotic or angular expansion. Components from each of the top expandable assembly 20A and the bottom expandable assembly 20B expand in the lordotic or angular direction. The distal cage 10 is driven or translated proximally towards the proximal cage 60 to a second position via further action of the drive screw 72. Upon translation of the distal cage 10 proximally towards the proximal cage 60, the top expandable assembly 20A and the bottom expandable assembly 20B are vertically expanded away from each other until each of the top expandable assembly 20A and the bottom expandable assembly 20B are disposed at a desired angle relative to the horizontal (h). The desired angle may range from about 7° to about 20°, such as about 7.5°, 8°, 10°, 12°, 15°, 18°, or an angle within a range defined by any two of the foregoing values.

Figure 19A:
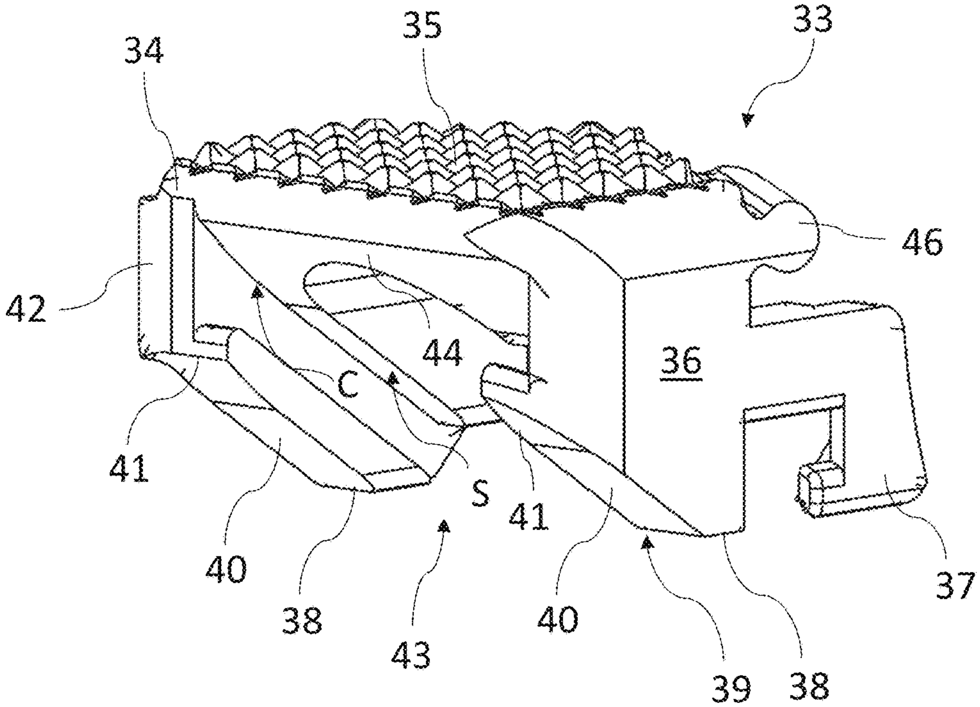
FIG. 19A illustrates a distal perspective view and FIG. 19B illustrates a proximal perspective view of the distal pivot or ramp from the expandable interbody implant of FIGS. 1 through 16.
Figure 19B:
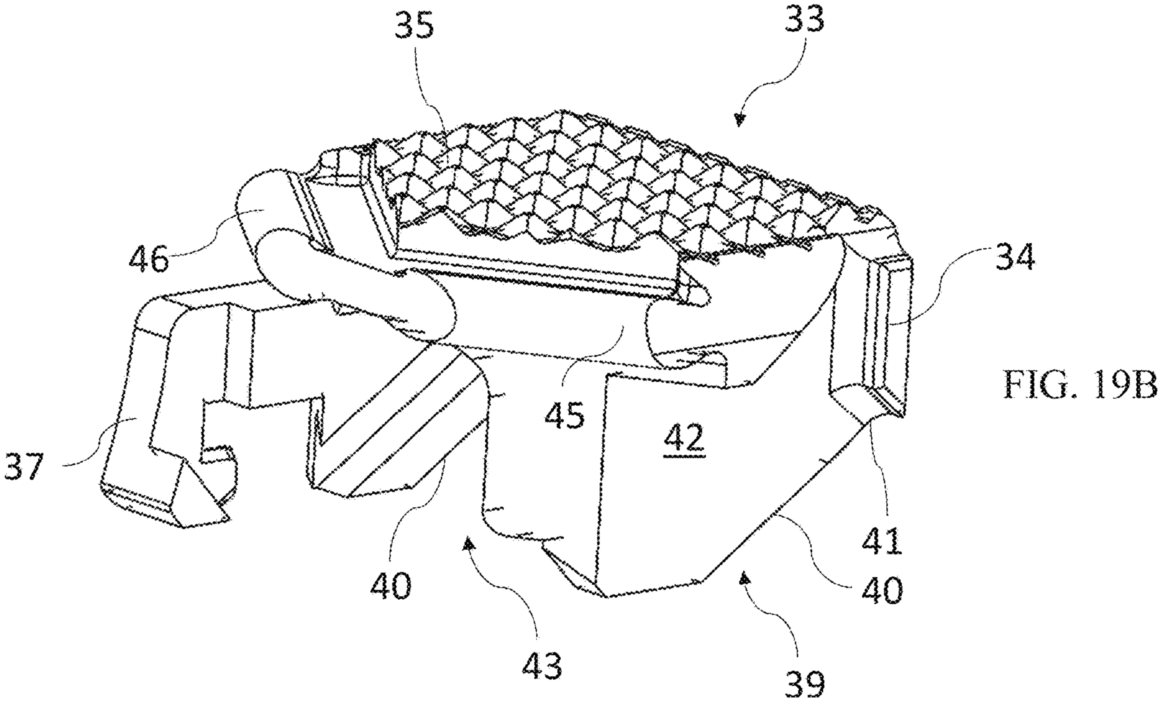

As the distal cage 10 is driven or translated proximally towards the proximal cage 60, the top distal ramp 33A (and the bottom distal ramp 33B) slides along the surface of the distal cage 10. Referring briefly to FIGS. 19A and 19B, in which a distal ramp 33 is illustrated, the top distal ramp 33A (and the bottom distal ramp 33B) includes a first sidewall 36 which includes the hook portion 37 and a ramp portion 39. The ramp portion 39 includes a straight portion 40 and a curved portion 41. Referring now to FIG. 11 together with FIGS. 19A and 19B, as the top distal ramp 33A (and the bottom distal ramp 33B) continues to slide along the surface of the distal cage 10, the straight portion 40 of the ramp portion 39 becomes parallel to the surface of the distal cage 10.

Referring briefly to FIGS. 6 and 9, when the implant 100 is in the collapsed configuration and/or the medial-lateral expansion configuration 102, the straight portion 40 of the ramp portion 39 is not parallel to and not in contact with the distal cage 10. However, as the distal cage 10 is driven proximally towards the proximal cage 60 to the second position, the straight portion 40 of the ramp portion 39 becomes parallel to and abuts the surface of the distal cage 10. This connection between the straight portion 40 of the ramp portion 39 and the distal cage 10 facilitates disposition of the top expandable assembly 20A in the desired angle. As translation of the distal cage 10 towards the proximal cage 60 continues, the straight portion 40 of the ramp portion 39 of the top distal ramp 33A (and the bottom distal ramp 33B) will continue to slide along the distal cage 10.

Figure 20A:
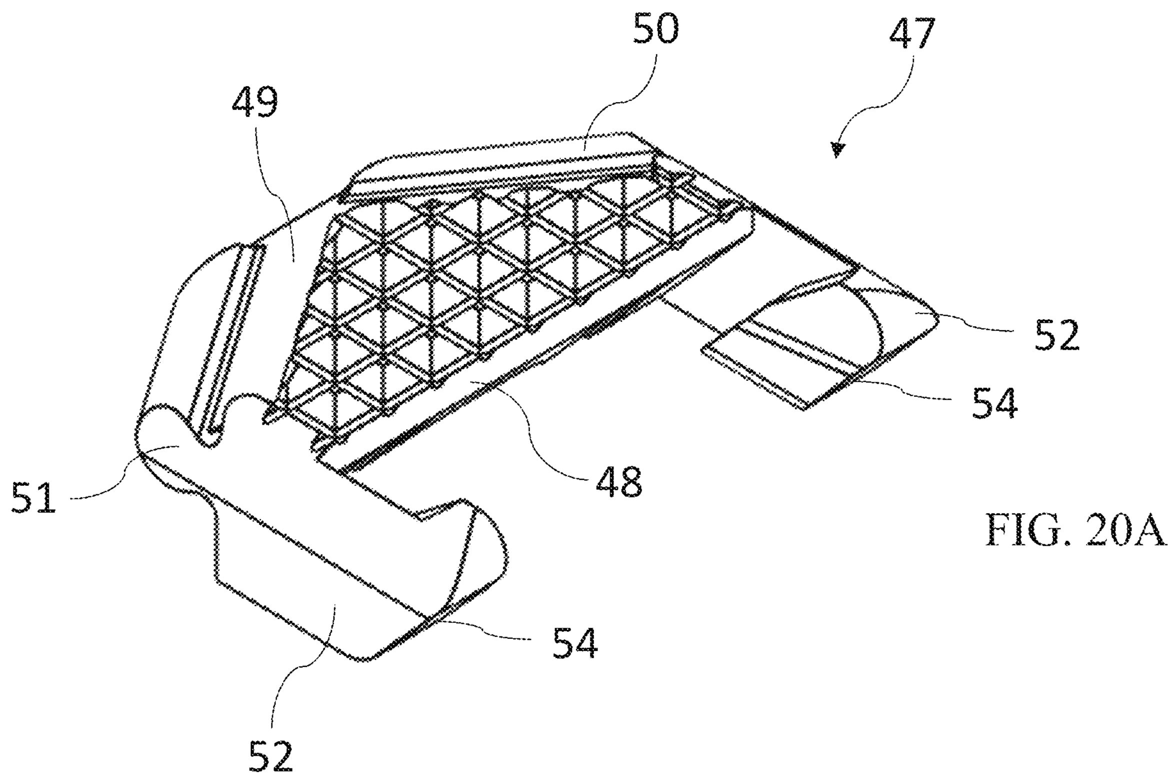
FIG. 20A illustrates a top, proximal perspective view
Figure 20B:
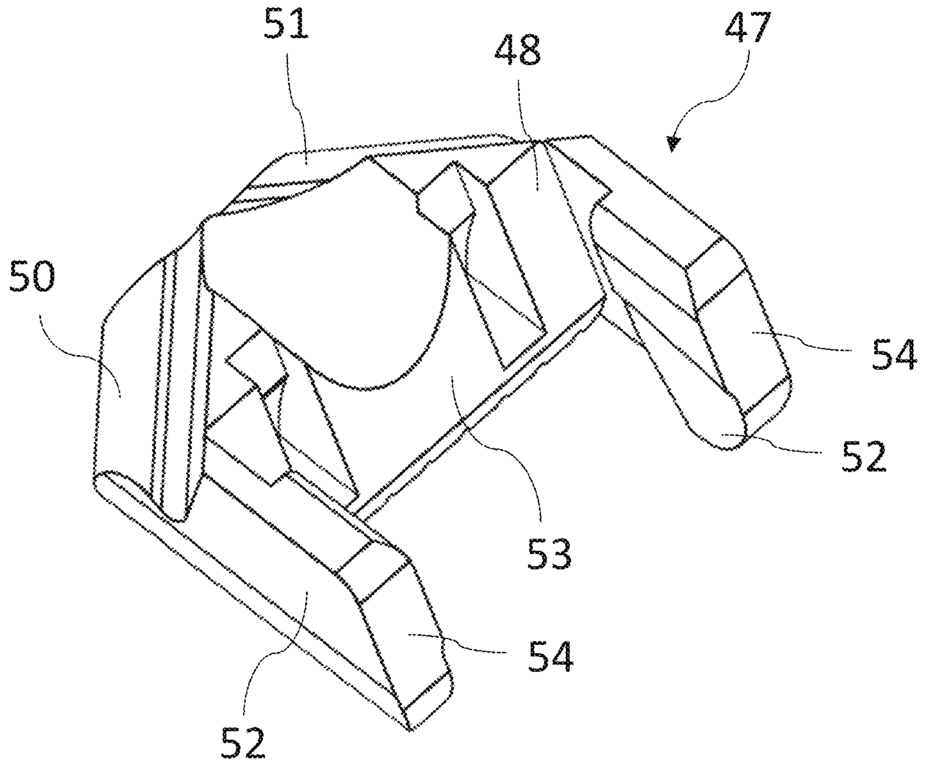
FIG. 20B illustrates a bottom, proximal perspective view of the proximal pivot or ramp from the expandable interbody implant of FIGS. 1 through 16.

A similar alignment occurs with the proximal ramps 47 (e.g., the top proximal ramp 47A and the bottom proximal ramp 47B) and the proximal cage 60. Referring briefly to FIGS. 20A and 20B, which illustrate a proximal ramp 47, the top proximal ramp 47A includes lateral wings 52 extending from a body 48. The lateral wings 52 each include a ramp portion 54 which interfaces and engages with the proximal cage 60. Referring briefly to FIGS. 6 and 9, when the implant 100 is in the medial-lateral expansion configuration 102, the ramp portion 54 of the top proximal ramp 47A is not parallel to the proximal cage 60 when the implant 100 is in the collapsed configuration or the medial-lateral expansion configuration 102. However, as the distal cage 10 is driven proximally towards the proximal cage 60 to the second position, the ramp portion 54 of the top proximal ramp 47A becomes parallel to and abuts the surface of the proximal cage 60.

Referring to FIG. 11, clearance of the hook portion 37A from the channel 32B in the first bottom endplate 21B allows for the lordotic or angular expansion of the top and bottom expandable assemblies 20A and 20B. Specifically, clearance of the hook portion 37A from the channel 32B in the first bottom endplate 21B allows the top distal ramp 33A to slide along the distal cage 10.

Additionally, clearance of the cut-out 29 by the projection 61P of the proximal cage 60 allows for the lordotic or angular expansion of the top and bottom expandable assemblies 20A and 20B. Specifically, clearance of the cut-out 29 by the projection 61P of the proximal cage 60 allows the proximal extension 26A of the second top endplate 22A to hingedly move away from the proximal extension 26B of the first bottom endplate 21B. Clearance of the cut-out 29 by the projection 61P of the proximal cage 60 also allows the ramp portion 54 of the lateral wings 52 of the top proximal ramp 47A to abut the surface of the proximal cage 60 and slide along the proximal cage 60.

Figure 13:
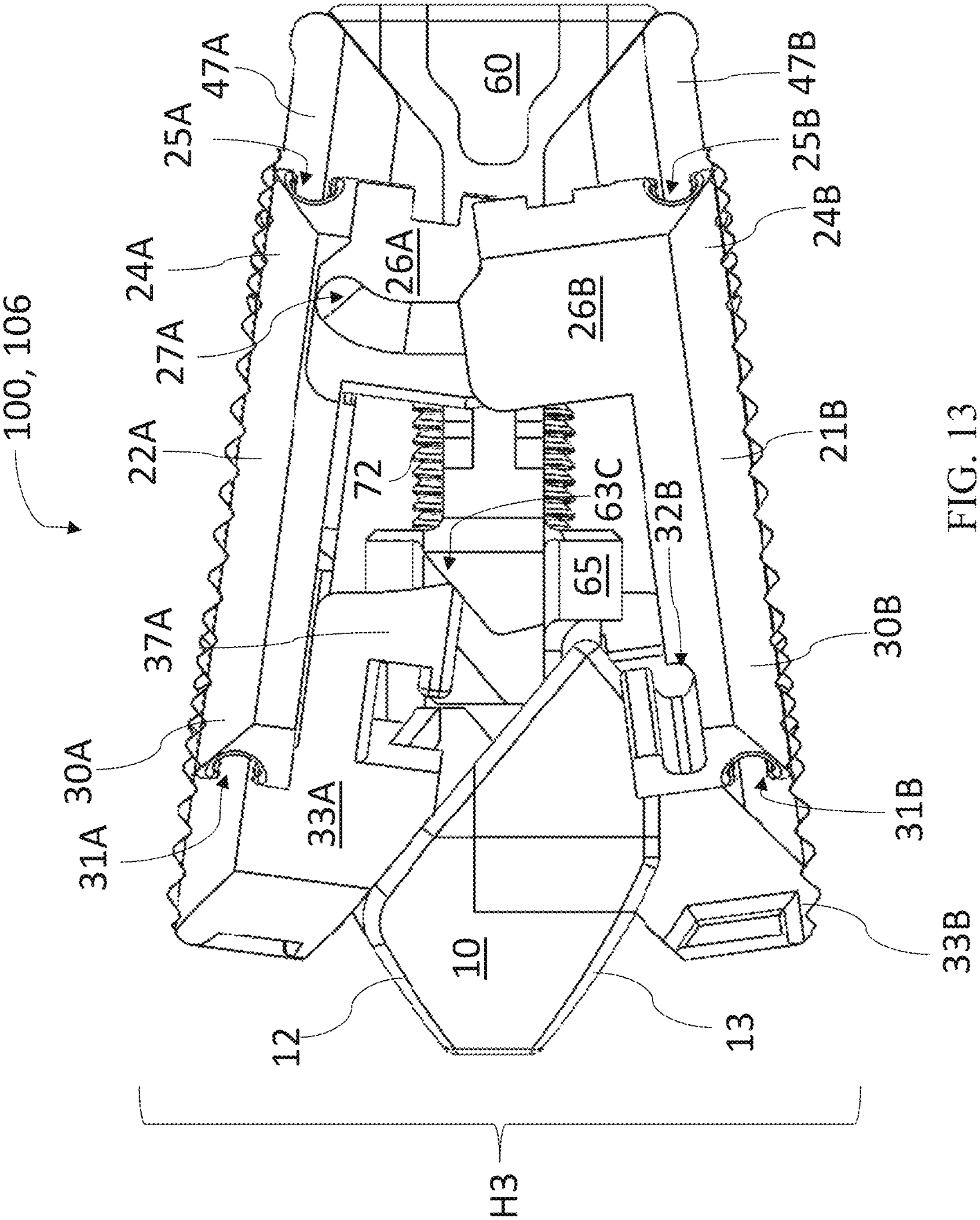
FIG. 13 illustrates a side view of the expandable interbody implant of FIG. 12 in a third cranial-caudal expanded configuration.
Figure 14:
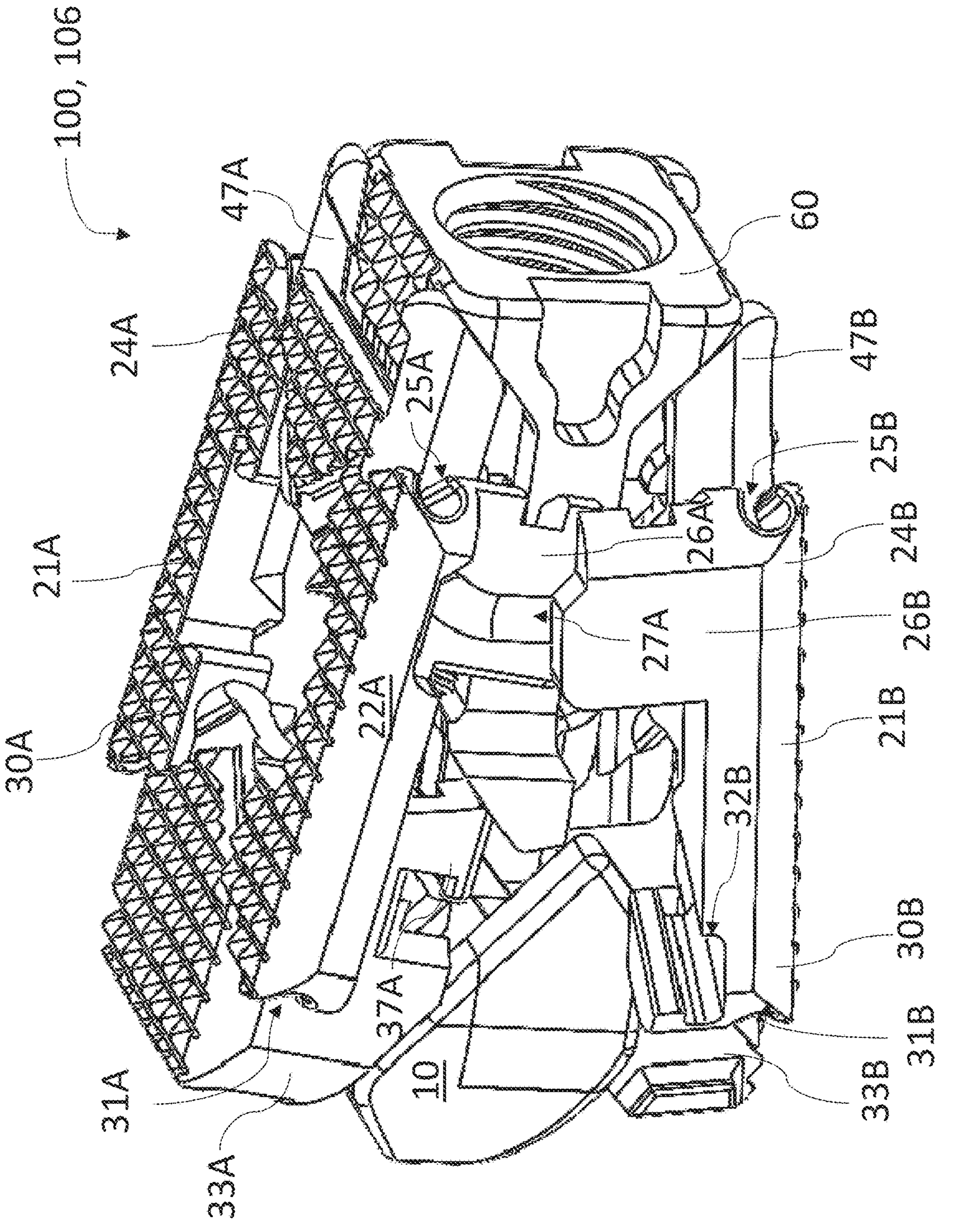
FIG. 14 illustrates proximal, perspective view of the expandable interbody implant of FIG. 12 in a third cranial-caudal expanded configuration.

As the top expandable assembly 20A is moved vertically away from the bottom expandable assembly 20B to the desired angle, the implant 100 increases in height from H1 to H2. H2 may range from about 9.5 mm to about 12.5 mm, such as 10, 10.5, 11, 11.5, 12 mm, or a height within a range defined by any two of the foregoing values. Additionally, to enable the angular movement of the top endplate assembly 20A away from the bottom endplate assembly 20B, as seen in FIG. 13, the proximal extension 26A of the second top endplate 22A defines a groove 27A in which a projection 28B of the first bottom endplate 21B (not illustrated, see FIG. 21B) slides and moves. As the top distal ramp 33A and the bottom distal ramp 33B slide along distal cage 10, the projection or protrusion 28B of the first bottom endplate 21B moves along the groove 27A, allowing the second top endplate 22A to be moved angularly with respect to the first bottom endplate 21B. Similarly, the first top endplate 21A moves angularly with respect to the second bottom endplate 22B.

Figure 12:
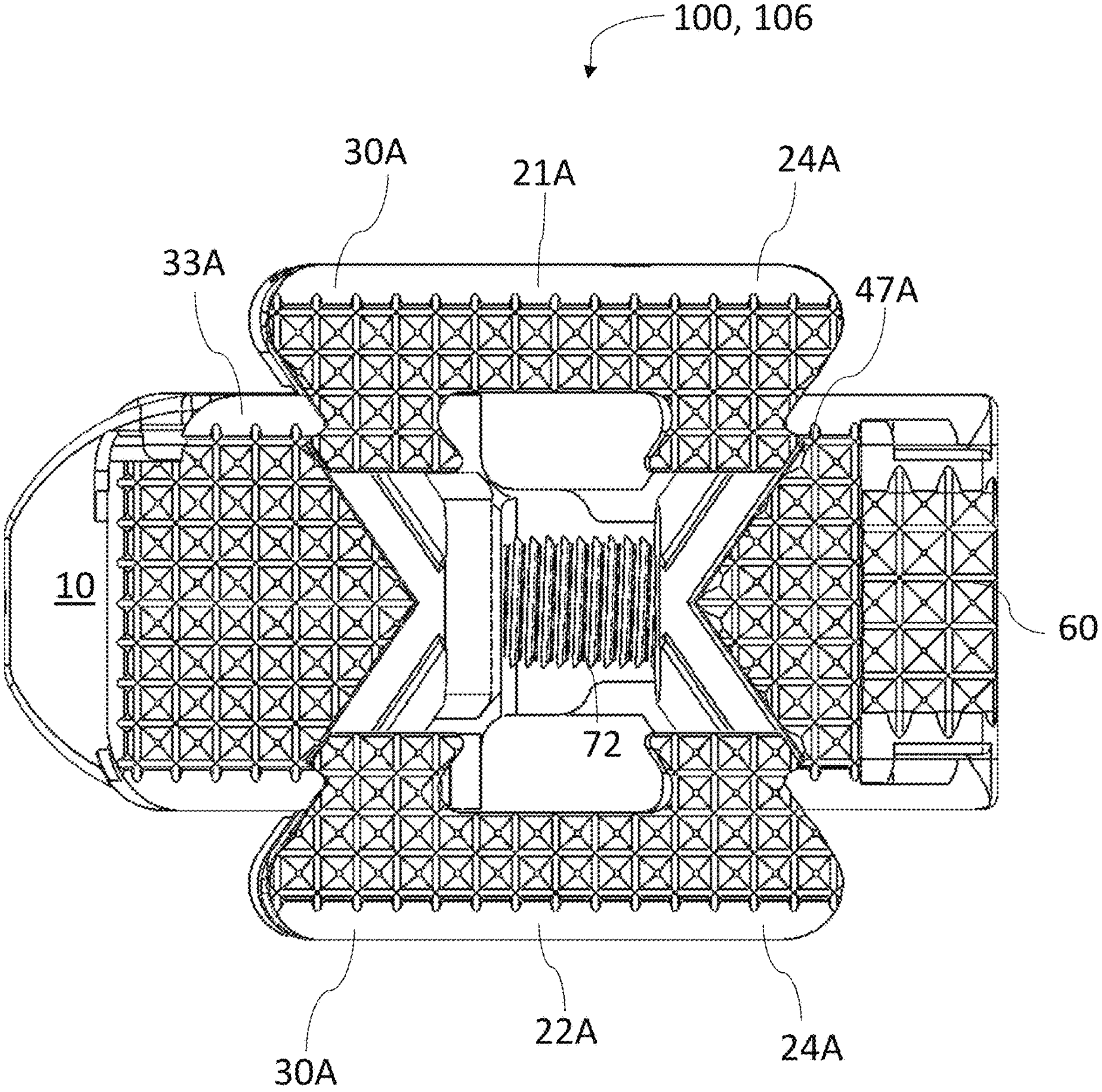
FIG. 12 illustrates a top view of the expandable interbody implant of FIG. 1 in a third cranial-caudal expanded configuration.

FIGS. 12 through 16 illustrate the expandable interbody implant 100 of FIG. 1 in a third cranial-caudal expanded configuration 106. As seen in FIG. 12, the medial-lateral expansion of the top expandable assembly 20A and the bottom expandable assembly 20B is maintained throughout the cranial-caudal or vertical expansion. As seen in FIG. 13, the desired angle of the top expandable assembly 20A and the bottom expandable assembly 20B reached during the lordotic or angular expansion is also maintained throughout the cranial-caudal or vertical expansion.

Figure 15:
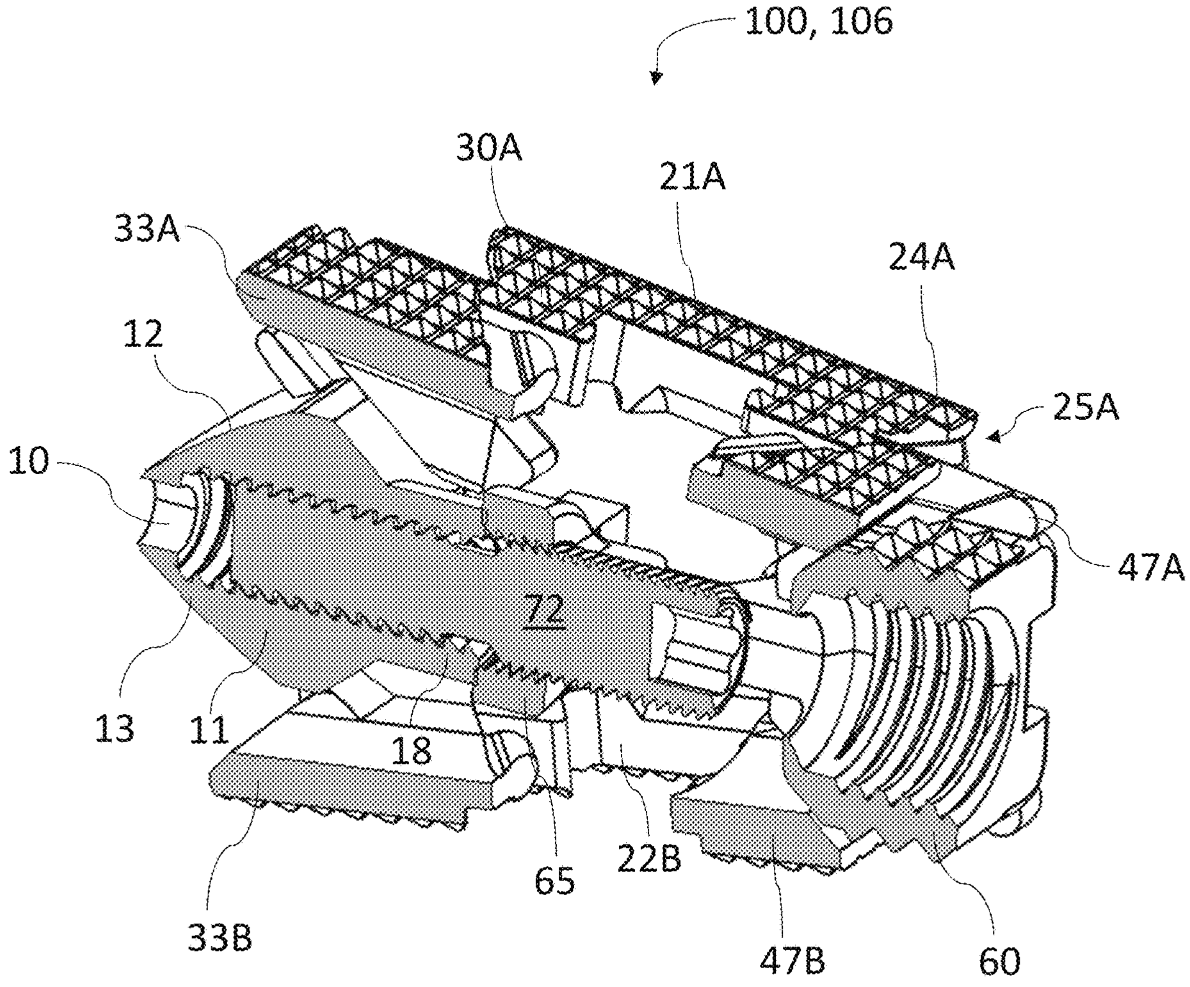
FIG. 15 illustrates a cross-sectional view of FIG. 14.
Figure 16:
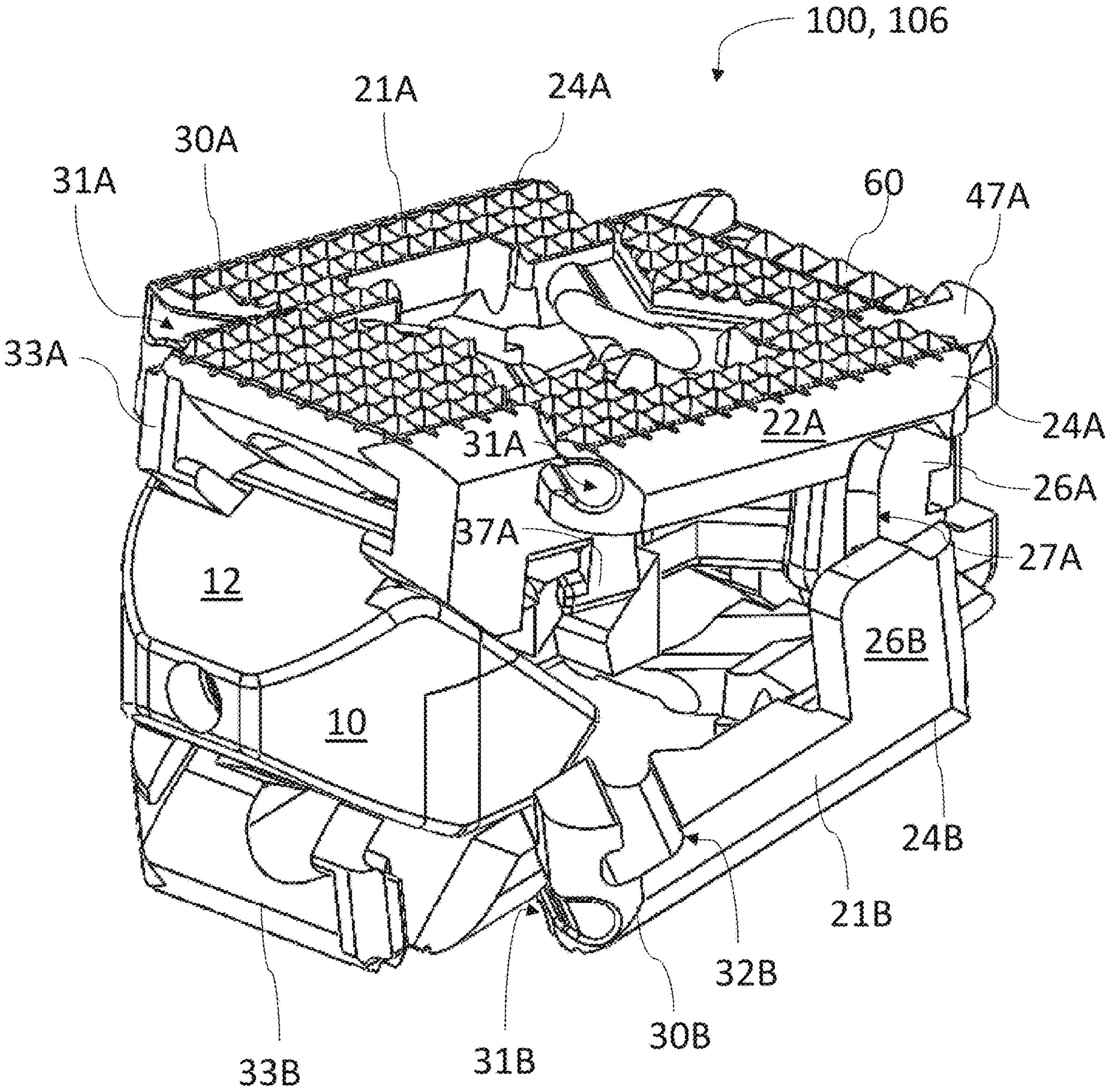
FIG. 16 illustrates a distal, perspective view of the expandable interbody implant of FIG. 12 in a third cranial-caudal expanded configuration.

Components from each of the top expandable assembly 20A and the bottom expandable assembly 20B expand in the cranial-caudal or vertical direction. The distal cage 10 is driven or translated proximally towards the proximal cage 60 to a third position via further action of the drive screw 72. As seen in FIG. 15, in the third position, the distal cage 10 hits a stop 65 of the proximal cage 60 and cannot further move proximally. The distal cage 10 includes a proximal extension 18 that hits and abuts the stop 65 of the proximal cage 60, thereby arresting further proximal movement of the distal cage 10 towards the proximal cage 60. Upon translation of the distal cage 10 proximally towards the proximal cage 60, the top expandable assembly 20A and the bottom expandable assembly 20B are vertically expanded away from each other.

Specifically, each of the top distal ramp 33A and the bottom distal ramp 33B slide along respective surfaces (e.g., top surface 12 and bottom surface 13) of the distal cage 10. As the top distal ramp 33A and the bottom distal ramp 33B slide along distal cage 10, the top proximal ramp 47A and the bottom proximal ramp 47B slide along respective surfaces of the proximal cage 60. Additionally, the proximal extension 26A of the second top endplate 22A moves (e.g., in a hinge-type motion) along the proximal extension 26B of the first bottom endplate 21B vertically extending the endplates away from each other. As seen in FIG. 13, the proximal extension 26A of the second top endplate 22A defines a groove 27A in which a projection 28B of the first bottom endplate 21B (not illustrated, see FIG. 21B) slides and moves. As the top distal ramp 33A and the bottom distal ramp 33B slide along distal cage 10, the projection or protrusion 28B of the first bottom endplate 21B moves along the groove 27A, allowing the second top endplate 22A to be moved vertically away from the first bottom endplate 21B.

The proximal extension 26A of the first top endplate 21A has the same hinged relationship with the proximal extension 26B of the second bottom endplate 22B. Specifically, the proximal extension 26A of the first top endplate 21A moves (e.g., in a hinge-type motion) vertically away from the proximal extension 26B of the second bottom endplate 22B. However, the second bottom endplate 22B defines a groove 27B through which a projection or protrusion 28A of the first top endplate 21A slides and moves.

As the top expandable assembly 20A is moved vertically away from the bottom expandable assembly 20B to the desired angle, the implant 100 increases in height from H2 to H3. H3 may range from about 12.5 mm to about 17.5 mm, such as 13, 13.5, 14, 14.5, 15, 15.25, 15.5 mm, 16 mm, 16.5 mm, 17 mm, 17.5 mm, or a height within a range defined by any two of the foregoing values.

Figure 17A:
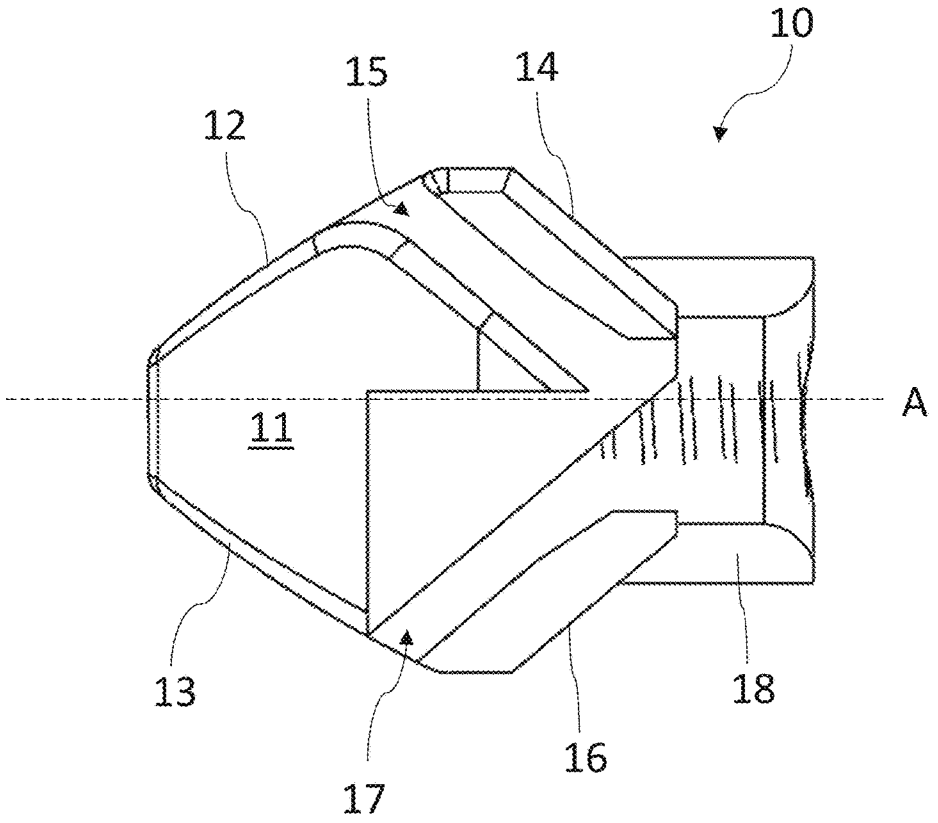
FIG. 17A illustrates a side view and FIG. 17B illustrates a proximal perspective view of the distal cage from the expandable interbody implant of FIGS. 1 through 16.
Figure 17B:
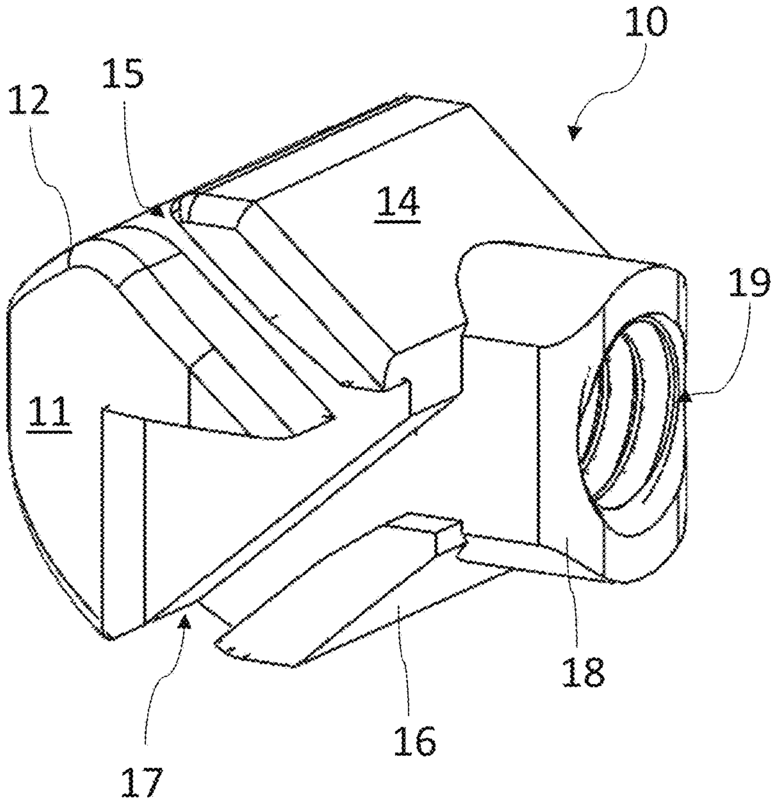

FIGS. 17A and 17B illustrate the distal cage 10 from the expandable interbody implant 100 of FIGS. 1 through 16. The distal cage 10 includes a body 11 having a top surface 12 and a bottom surface 13 opposite the top surface 12. The body 11 may have a substantially diamond shape, where the top surface 12 tapers towards the bottom surface 13. In some embodiments, the body 11 may receive a cap 90, such as illustrated in FIG. 24. The cap may cover grooves of the distal cage 10 and may be welded onto the distal cage 10 during assembly. The body 11 also includes a proximal extension 18 that defines a threaded bore 19. The threaded bore 19 has threads that correspond to threadings at a distal end 76 of the drive screw 72 (see FIGS. 23A and 23B). The distal cage 10 is diagonally symmetrical about an axis A of the distal cage 10.

The top surface 12 of the body 11 includes a top ramp 14 and a top slot 15. The top surface 12 may taper towards the bottom surface 13 in an opposite direction of the top ramp 14. Similarly, the bottom surface 13 includes a bottom ramp 16 and a bottom slot 17. The top distal pivot or ramp 33A of the top expandable assembly 20A slides along the top ramp 14 of the distal cage 10 and engages the top slot 15. Similarly, the bottom distal pivot or ramp 33B of the bottom expandable assembly 20B slides along the bottom ramp 16 and engages the bottom slot 17. Referring briefly to FIGS. 11 and 13, when the implant 100 is in the lordotic expansion configuration 104 and/or the cranial-caudal expansion configuration 106, the straight portion 40 of the ramp portion 39 of the top distal ramps 33A is parallel to the top ramp 14 and the top slot 15. Likewise, the straight portion 40 of the ramp portion 39 of the bottom distal ramps 33B is parallel to the bottom ramp 16 and the bottom slot 17.

Figure 18A:
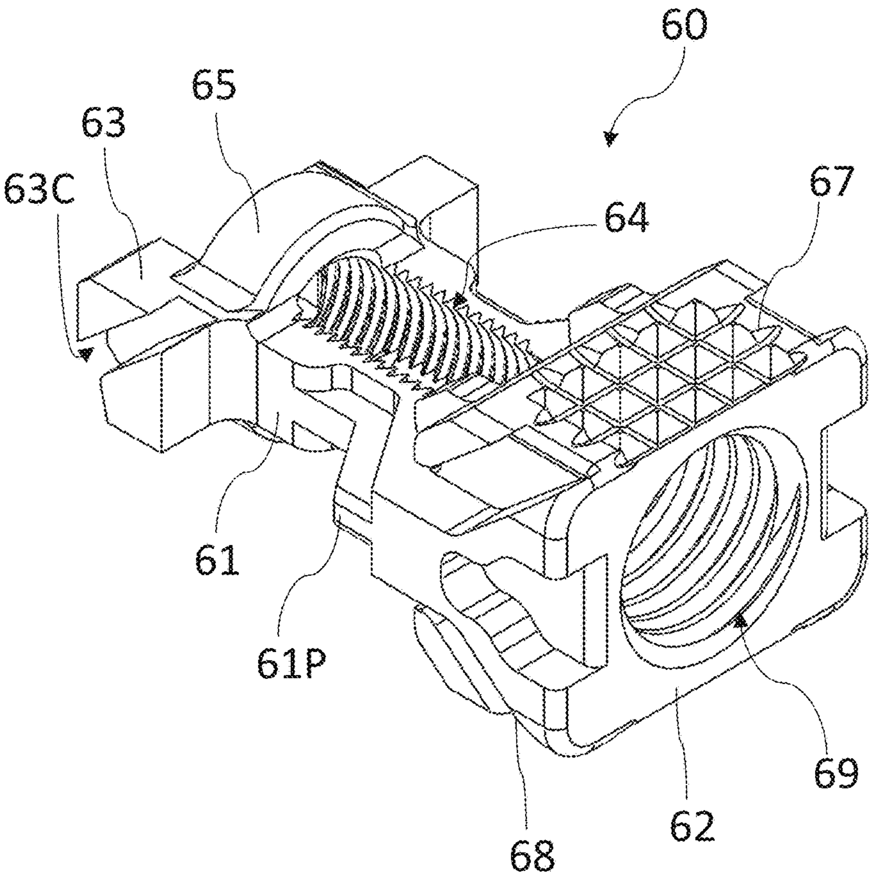
FIG. 18A illustrates a proximal perspective view and FIG. 18B illustrates a distal perspective view of the proximal cage from the expandable interbody implant of FIGS. 1 through 16.
Figure 18B:
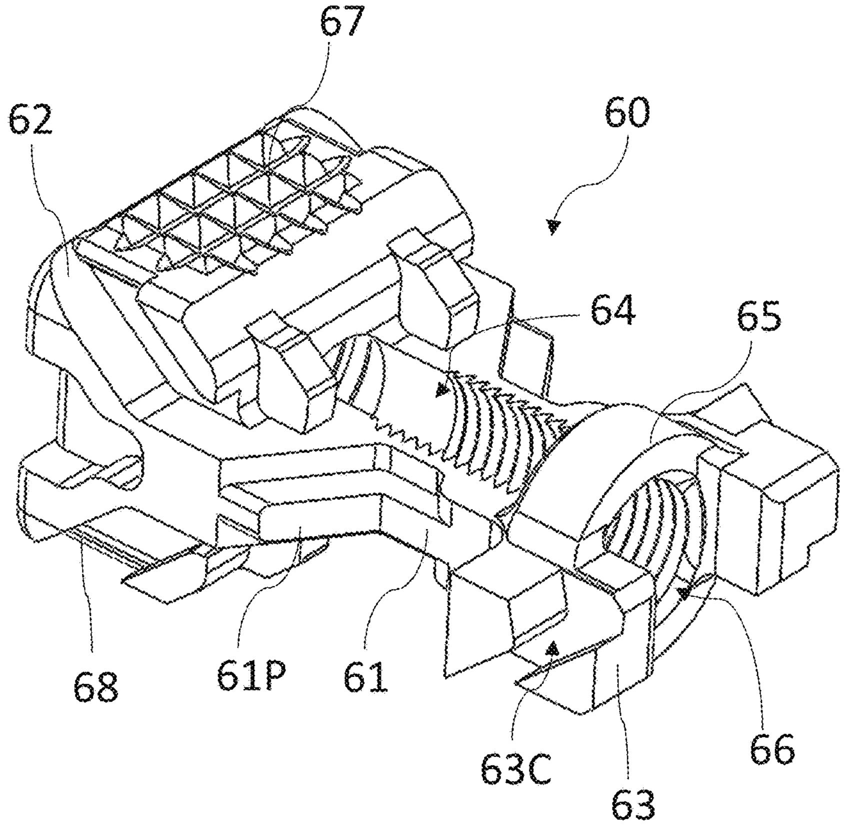

FIGS. 18A and 18B illustrate the proximal cage 60 from the expandable interbody implant 100 of FIGS. 1 through 16. The proximal cage 60 includes a body 61 extending between a proximal end 62 and a distal end 63, and having a top surface 67 and a bottom surface 68. The proximal end 62 defines an opening 69 for receiving a driver or handle, such as the driver 95 in FIGS. 26A through 27. The distal end 63 may be open or substantially open to receive the proximal extension 18 of the distal cage 10 in the third position (see FIG. 13).

Disposed near the distal end 63 is the stop 65 which mechanically stops proximal motion of the distal cage 10 when the proximal extension 18 of the distal cage 10 is received within the distal end 63 of the proximal cage 60. The stop 65 defines a threaded opening 66 to receive a proximal end 74 of the drive screw 72. Defined in the distal end 63 are channels 63C that engage with the hook portion 37 of the distal ramp 33 when the expandable interbody implant 100 is in the third cranial-caudal configuration 106. For example, referring briefly to FIG. 11, as the top distal ramp 33A (or the bottom distal ramp 33B) slides along the distal cage 10, the hook portion 37A starts to engage the channel 63C. Referring to FIG. 13, as the top distal ramp 33A (or the bottom distal ramp 33B) continues to slide along the distal cage 10, the hook portion 37A slides within the channel 63C, thereby facilitating the vertical expansion. This coupling of the hook portion 37A and the channel 63C stabilizes the expandable interbody implant 100 during the cranial-caudal expansion 106.

The body 61 of the proximal cage 60 also defines a threaded channel 64 extending between the stop 65, the opening 66, the proximal end 62, and the opening 69. The body 61 also includes projections 61P that engage the channel 29 defined in the proximal extensions 26A and 26B of the top and bottom expandable assemblies 20A and 20B (see FIGS. 4, 8, 11, and 13).

FIGS. 19A and 19B illustrate the distal pivot or ramp 33 (either 33A or 33B) from the expandable interbody implant 100 of FIGS. 1 through 16. As discussed, the top distal ramp 33A is identical to the bottom distal ramp 33B. Accordingly, the illustrated distal ramp 33 in FIGS. 19A and 19B will be discussed generally and it is to be understood that the features discussed in FIGS. 19A and 19B apply to both the top distal ramp 33A and the bottom distal ramp 33B. The distal ramp 33 includes a body 34 having an outer surface 35 and a ramped inner surface 44 opposite the outer surface 35. The outer surface 35 includes a first projection 45 for interfacing with the distal ends 30A, 30B of the second endplates 22A, 22B and a second projection 46 for interfacing with the distal ends 30A, 30B of the first endplates 21A, 21B. The body 34 includes a first sidewall 36 and a second sidewall 42 opposite the first sidewall 36.

The outer surface 35, the first sidewall 36, and the second sidewall 42 together define an open inner surface 43. The open inner surface 43 includes the ramped surface 44, which slides against the distal cage 10 when the interbody 100 is expanded in the lordotic configuration 104, and the cranial-caudal configuration 106. The ramped surface 44 slides along the ramps 14 or 16 of the distal cage 10, as appropriate (i.e., a bottom ramped surface 44 of the bottom distal ramp 33B slides along the bottom ramp 16 of the distal cage 10). The first sidewall 36 includes the hook portion 37.

The ramped surface 44 includes a straight portion S and a curved portion C. The curved portion C of the ramped surface 44 facilitates engagement of the distal cage 10, such that the ramped surface 44 may slide along the distal cage 10. As the ramped surface 44 slides along the distal cage 10, the straight portion S will become parallel to a surface of the distal cage 10 (see FIG. 16).

The hook portion 37 provides an interlock between the top expandable assembly 20A and the bottom expandable assembly 20B. Specifically, the hook portion 37A of the top distal ramp 33A interlocks with the first bottom endplate 21B (the channel 32B at the distal end 30B) of the bottom expandable assembly 20B. Simultaneously, the hook portion 37B of the bottom distal ramp 33B interlocks with the first top endplate 21A (the channel 32A at the distal end 30A) of the top expandable assembly 20A. Until the hook portion clears the channels, the interbody 100 can only expand in the medial-lateral direction (i.e., in width).

The first sidewall 36 and the second sidewall 42 each also include a ramped portion 39. Specifically, the first sidewall 36 and the second sidewall 42 each extend from the outer surface 34 to an edge 38, which includes the ramp portion 39. The ramp portion 39 includes a straight portion 40 and a curved portion 41. The curved portion 41 of the ramp portion 39 facilitates engagement of the slots 15 or 17 of the distal cage 10, such that the ramp portion 39 may slide within the slots 15 or 17.

FIGS. 20A and 20B illustrate the proximal pivot or ramp 47 (either 47A or 47B) from the expandable interbody implant 100 of FIGS. 1 through 16. As discussed, the top proximal ramp 47A is identical to the bottom proximal ramp 47B. Accordingly, the illustrated proximal ramp 47 in FIGS. 20A and 20B will be discussed generally and it is to be understood that the features discussed in FIGS. 20A and 20B apply to both the top proximal ramp 47A and the bottom proximal ramp 47B. The proximal ramp 47 includes a body 48 having an outer surface 49 and a ramped inner surface 53 opposite the outer surface 49. The outer surface 49 includes a first projection 50 for interfacing with the proximal ends 24A, 24B of the second endplates 22A, 22B and a second projection 51 for interfacing with the proximal ends 24A, 24B of the first endplates 21A, 21B.

The body 48 also includes lateral wings 52, which include a ramp portion 54. The ramped bottom surface 53 slides along a surface (e.g., a top surface 67 or a bottom surface 68) of the proximal cage 60. The ramp portion 54 of the lateral wings 52 also slides along the proximal cage 60 (see, for example, FIGS. 6, 8, 11, and 13).

Figure 21A:
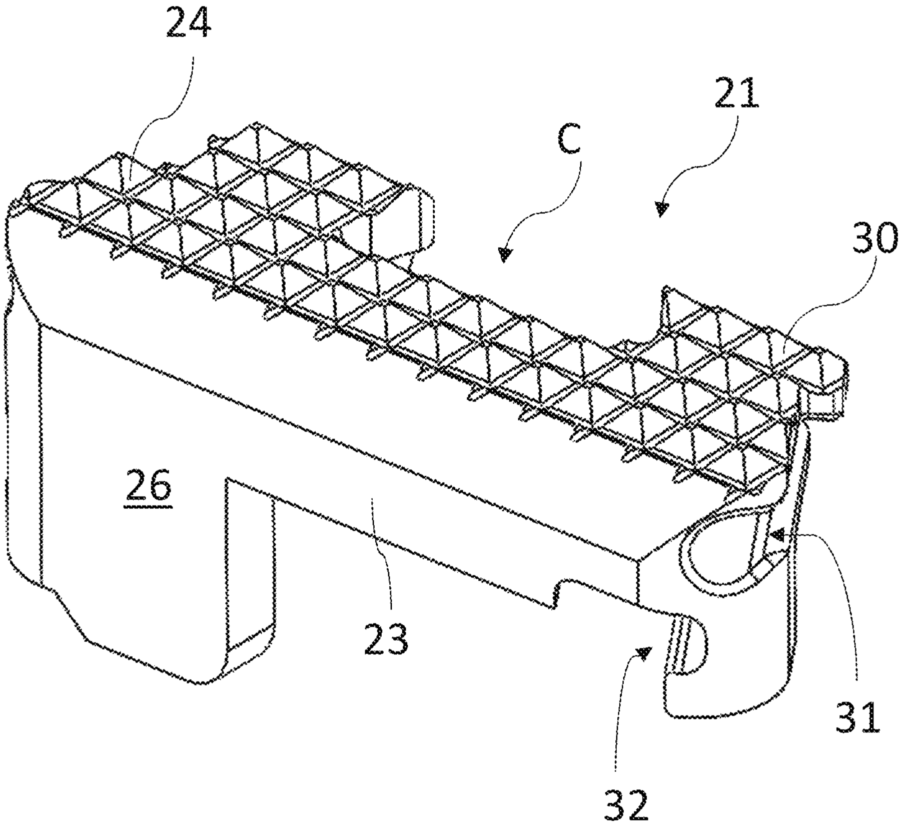
FIG. 21A illustrates a distal, perspective view
Figure 21B:
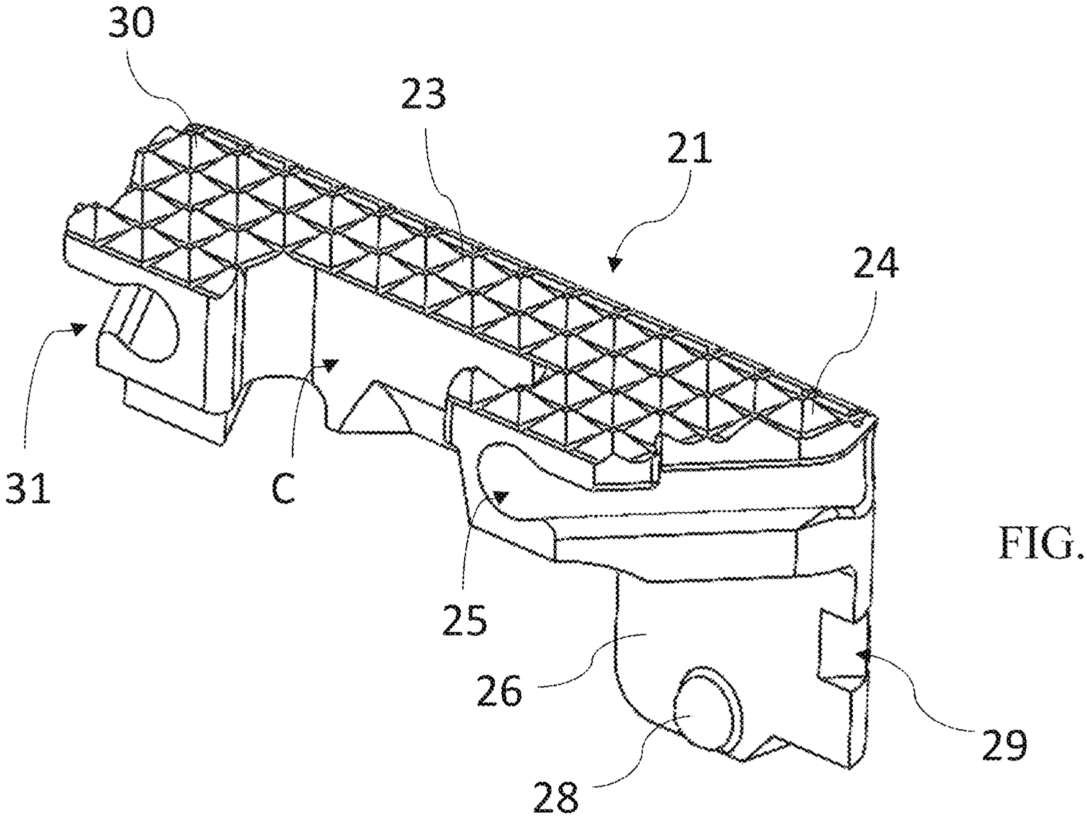
FIG. 21B illustrates a proximal, perspective view of the first endplate of the top or bottom expandable assembly from the expandable interbody implant of FIGS. 1 through 16, and the first endplate includes a channel that locks with a hook portion of the distal pivot or ramp from FIGS. 19A and 19B.

FIG. 21A illustrates a distal, perspective view and FIG. 21B illustrates a proximal perspective view of the first endplate 21 of the top (21A) or bottom (21B) expandable assemblies 20A, 20B from the expandable interbody implant 100 of FIGS. 1 through 16. Similar to the distal ramp 33 and the proximal ramp 47, the first top endplate 21A is identical to the first bottom endplate 21B. Accordingly, the illustrated first endplate 21 in FIGS. 21A and 21B will be discussed generally and it is to be understood that the features discussed in FIGS. 21A and 21B apply to both the first top endplate 21A and the first bottom endplate 21B.

The first endplate 21 includes a body 23 extending between a proximal end 24 and a distal end 30. Defined in the proximal end 24 is a channel 25 for engaging and sliding along the second projection 51 of the proximal ramp 47. The proximal end 24 also includes a proximal extension 26 for mating and mechanically engaging a proximal extension 26 of a corresponding second endplate 22 (see, for example, FIGS. 6, 8, 11, and 14). The proximal extension 26 of the first endplate 21 includes a protrusion 28 that mechanically engages a groove 27 defined in the proximal extension 26 of the second endplate 22. The proximal extension 26 also defines a cut-out or channel 29 that mates and overlaps with the cut-out 29 in a corresponding second endplate 22. The joined cut-outs 29 receive the projection 61P of the proximal cage 60 when the implant 100 is in the collapsed configuration.

The first endplate 21 includes or defines a channel 32 at the distal end 30 that locks with the hook portion 37 of the distal pivot or ramp 33 from FIGS. 19A and 19B. The hook portion 37 must clear the channel 32 to allow the implant 100 to expand in the lordotic configuration 104 and the cranial-caudal configuration 106. The distal end 30 also includes or defines a channel 31 for engaging and sliding along the second projection 46 of the distal ramp 33. The first endplate 21 and/or the body 23 may also define a cut-out C in a medial edge, thereby reducing an amount of material required to form the first endplate 21.

Figure 22A:
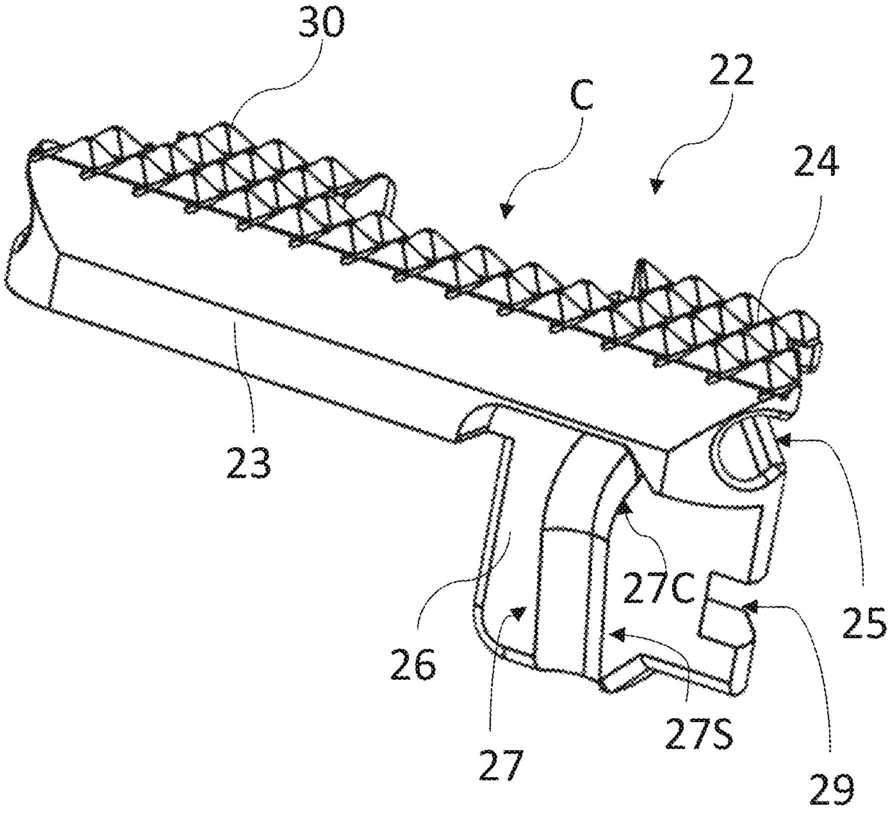
FIG. 22A illustrates a distal, perspective view
Figure 22B:
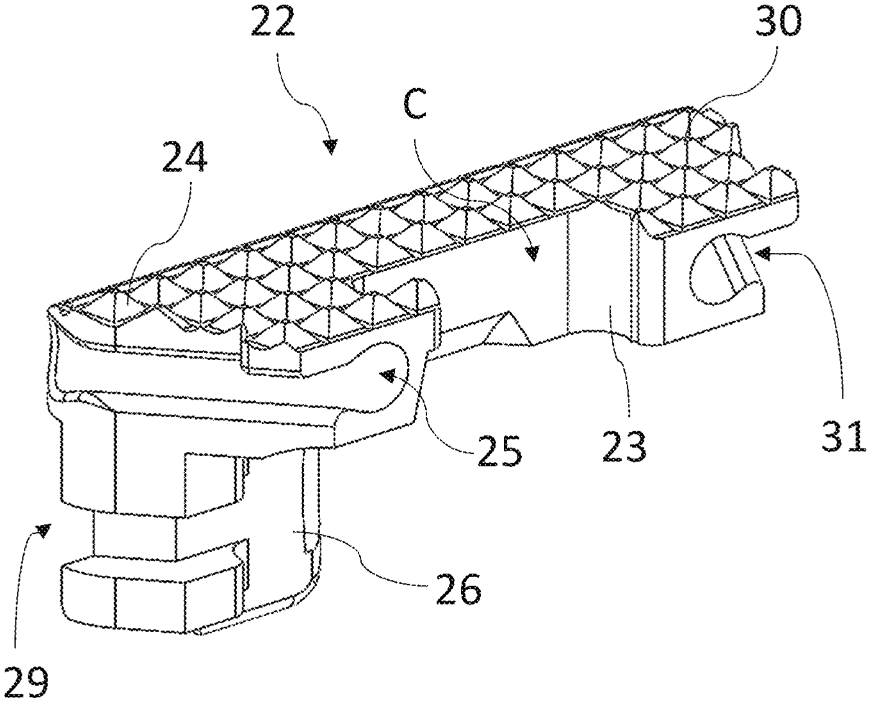
FIG. 22B illustrates a proximal perspective view of the second endplate of the top or bottom expandable assembly from the expandable interbody implant of FIGS. 1 through 16, and the second endplate includes a groove that engages with a projection of the first endplate of FIGS. 21A and 21B.

FIGS. 22A and 22B illustrate a second endplate 22 of the top or bottom expandable assemblies 20A, 20B from the expandable interbody implant 100 of FIGS. 1 through 16. As with the first endplate 21, the second top endplate 22A is identical to the second bottom endplate 22B. Accordingly, the illustrated second endplate 22 in FIGS. 22A and 22B will be discussed generally and it is to be understood that the features discussed in FIGS. 22A and 22B apply to both the second top endplate 22A and the second bottom endplate 22B. The second endplate 22 is also substantially identical to the first endplate 21, so like features will be labelled with like reference numbers.

The second endplate 22 includes a body 23 extending between a proximal end 24 and a distal end 30. Defined in the proximal end 24 is a channel 25 for engaging and sliding along the first projection 50 of the proximal ramp 47. The proximal end 24 also includes a proximal extension 26 for mating and mechanically engaging a proximal extension 26 of a corresponding first endplate 21 (see, for example, FIGS. 6, 8, 11, and 14). The proximal extension 26 of the second endplate 22 defines a groove 27 in which the projection 28 of the first endplate 21 slides and moves.

Referring briefly to FIG. 13 in conjunction with FIGS. 22A and 22B, the channel 27 is shaped to guide, first, the lordotic or angular movement and then, second, the cranial-caudal or height movement. Specifically, the shape of the groove 27 includes a curved section 27C then a substantially straight section 27S to facilitate these movements. The curved section 27C allows the top expandable assembly 20A and the bottom expandable assembly 20B to be angularly disposed in the lordotic direction. Then, the straight section 27S allows the top expandable assembly 20A and the bottom expandable assembly 20B to be vertically moved away from each other in the cranial-caudal direction.

The proximal extension 26 also defines a cut-out 29 that mates and overlaps with the cut-out 29 of the corresponding first endplate 21. The joined cut-outs 29 receive the projection 61P of the proximal cage 60 when the implant 100 is in the collapsed configuration.

The distal end 30 of the second endplate 22 includes or defines a channel 31 for engaging and sliding along the first projection 45 of the distal ramp 33. The second endplate 22 and/or the body 23 may also define a cut-out C in a medial edge, thereby reducing an amount of material required to form the second endplate 22.

Figure 23A:
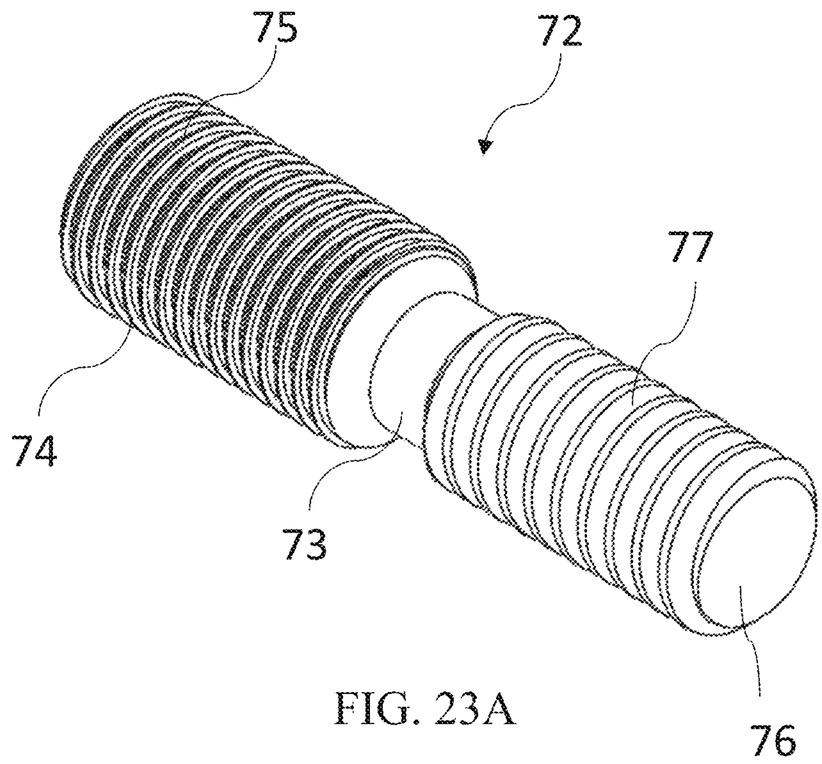
FIG. 23A illustrates a distal perspective view and FIG. 23B illustrates a proximal perspective view of the drive screw from the expandable interbody implant of FIGS. 1 through 16.
Figure 23B:
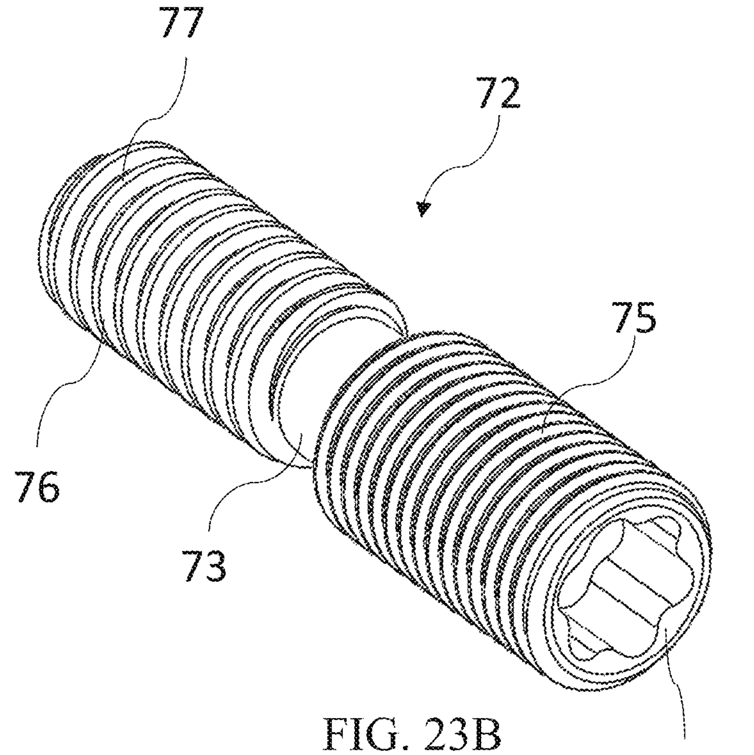
Figure 24:
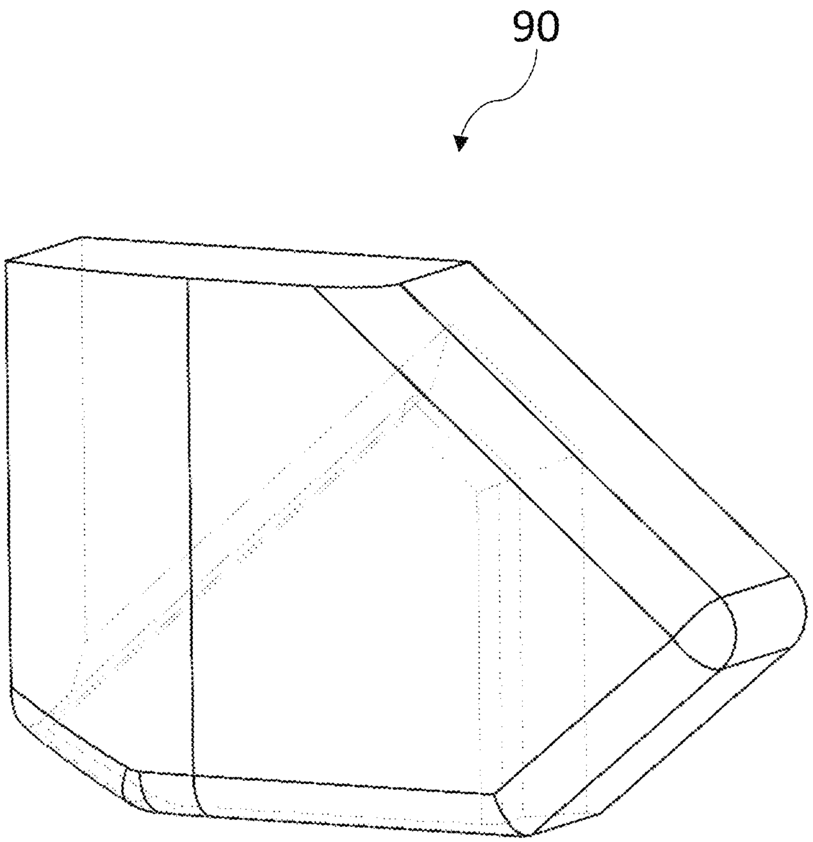
FIG. 24 illustrates a distal cage cap to cover a portion of the distal cage of FIGS. 17A and 17B.

FIGS. 23A and 23B illustrate the drive screw 72 from the expandable interbody implant 100 of FIGS. 1 through 16. The drive screw 72 includes a body 73 extending between a proximal end 74 and a distal end 76. The proximal end 74 includes threading 75 that corresponds to threading of the proximal cage 60. The distal end 76 includes threading 77 that corresponds to threading of the distal cage 10. The threadings 75 and 77 may be different from each other. Driving of the drive screw 72 causes the distal cage 10 to be translated proximally towards the proximal cage 60, thereby causing the implant 100 to expand firstly in the medial-lateral direction, secondly in the lordotic direction, and thirdly in the cranial-caudal direction.

Figure 25:
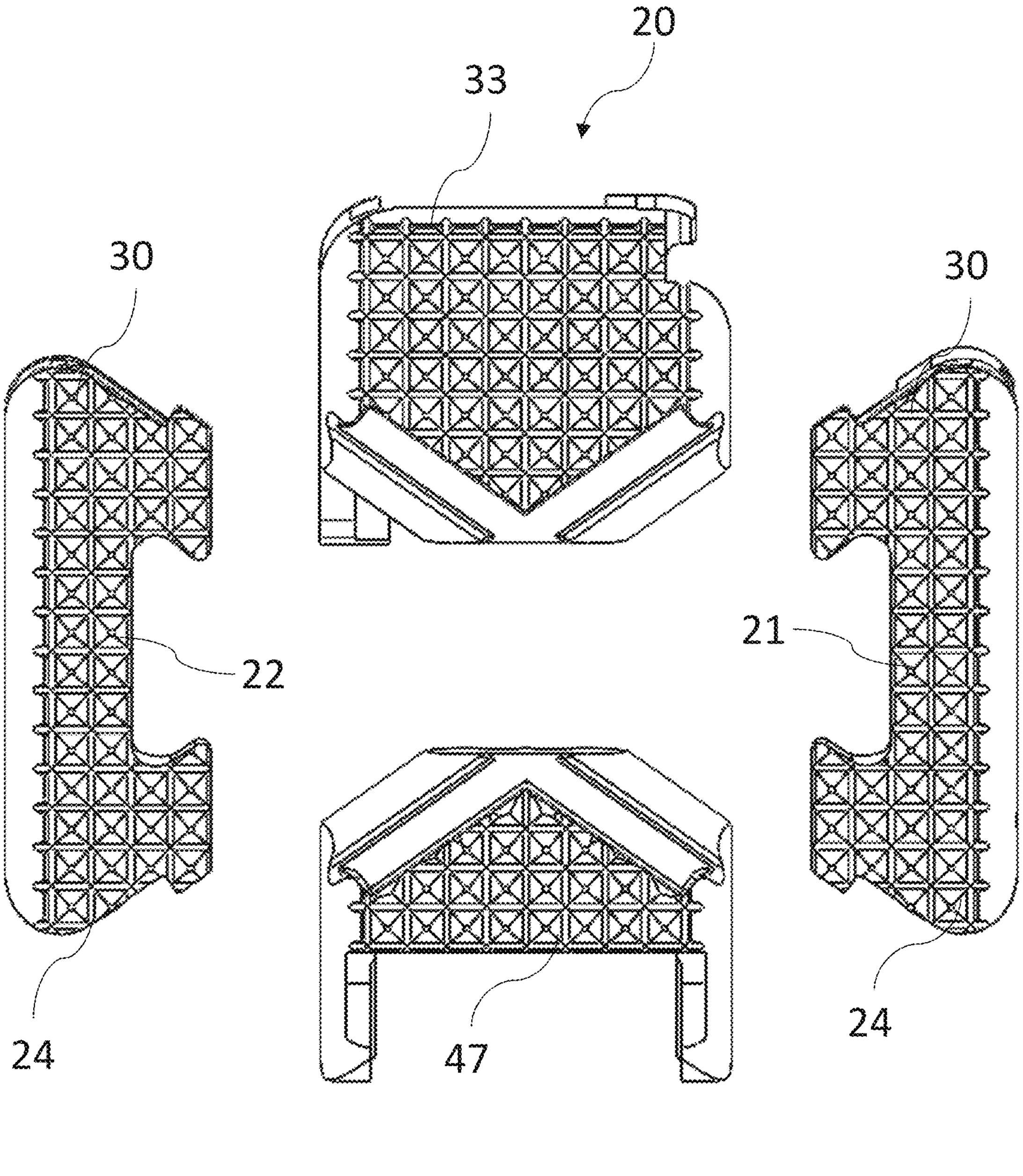
FIG. 25 illustrates an exploded view of the top or bottom expandable assembly from the expandable interbody implant of FIGS. 1 through 16.

FIG. 25 illustrates an exploded view of the top or bottom expandable assembly 20A, 20B from the expandable interbody implant 100 of FIGS. 1 through 16. As the top expandable assembly 20A is identical to the bottom expandable assembly 20B, discussion of the expandable assembly 20 of FIG. 25 equally applies to both the top and bottom expandable assemblies 20A, 20B. The expandable assembly 20 includes a first endplate 21, a second endplate 22 adjacent to the first endplate 21 in the collapsed position, a distal ramp 33, and a proximal ramp 47. The first and second endplates 21, 22 each have a proximal end 24 that is slidable along the proximal ramp 47 and a distal end 30 that is slidable along the distal ramp 33.

Figure 26A:
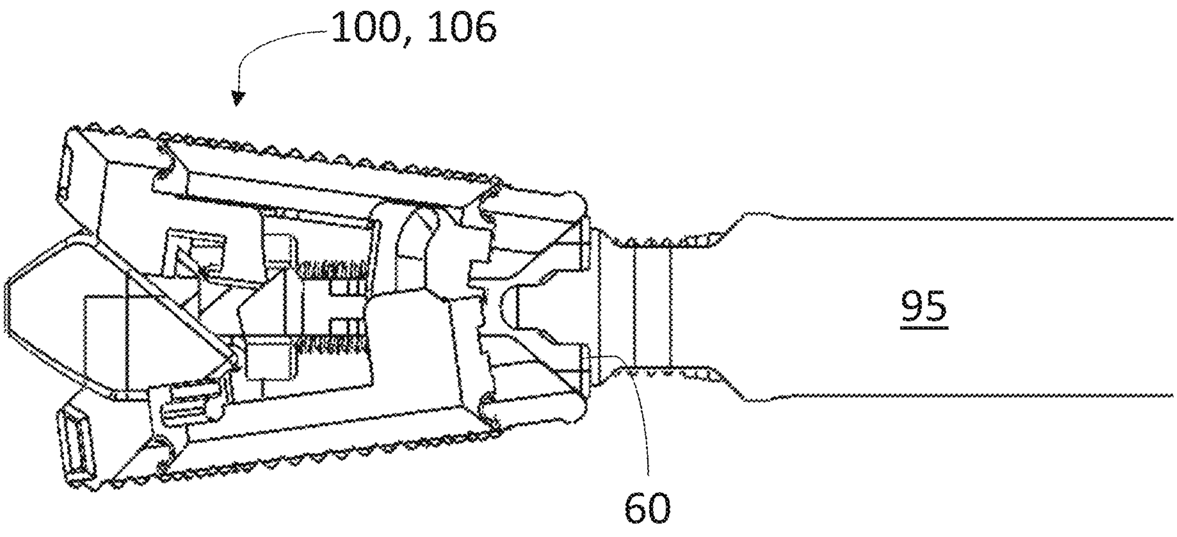
FIG. 26A illustrates a side view of the expandable interbody implant of FIGS. 10 through 16 attached to an inserter or driver and FIG. 26B illustrates a proximal perspective view of FIG. 26A.
Figure 26B:
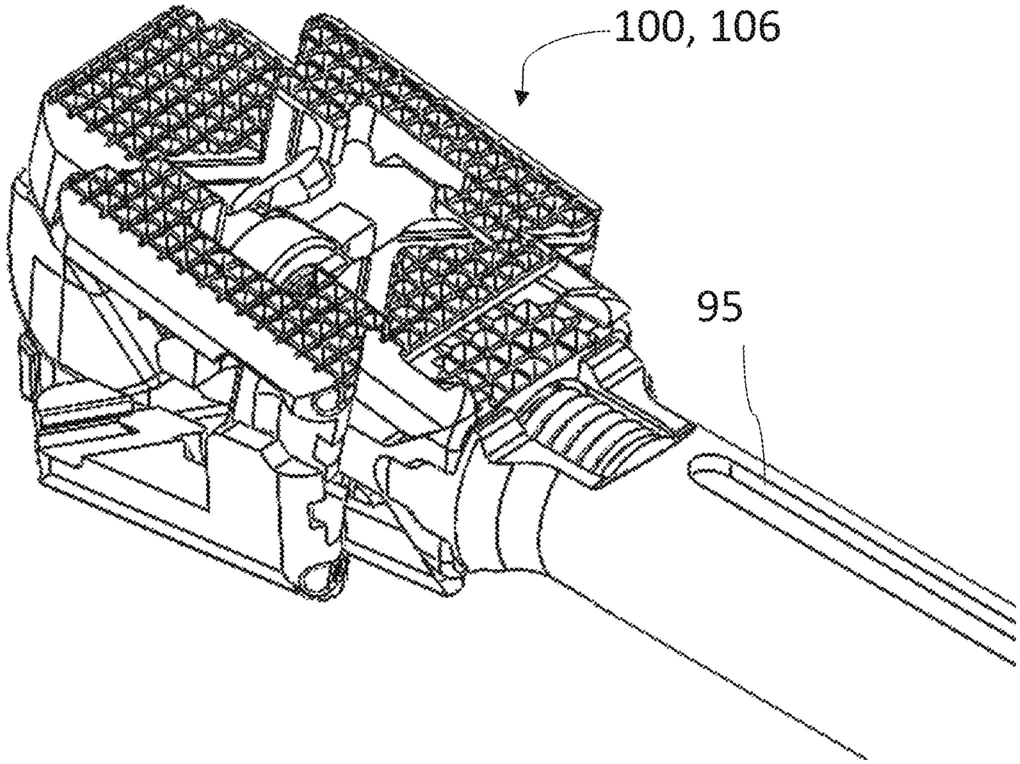
Figure 27:
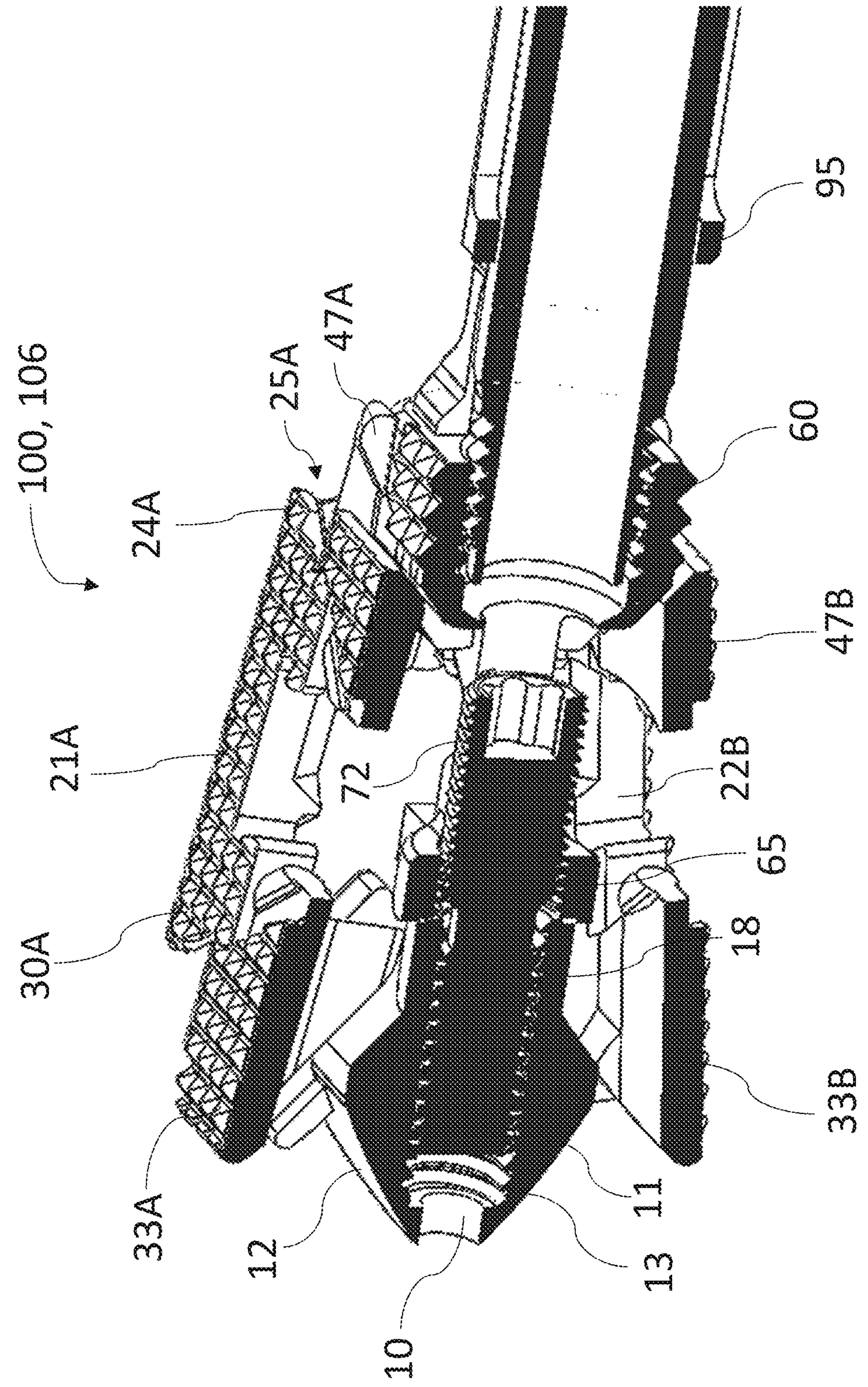
FIG. 27 illustrates a cross-sectional view of FIG. 26B.

FIGS. 26A through 27 illustrate the expandable interbody implant 100 of FIGS. 10 through 16 attached to an inserter or driver 95. The driver 95 is connectable to the proximal cage 60. The driver 95 may also engage the proximal end 74 of the drive screw 72 to facilitate translation of the distal cage 10 proximally towards the proximal cage 60.

Figure 28:
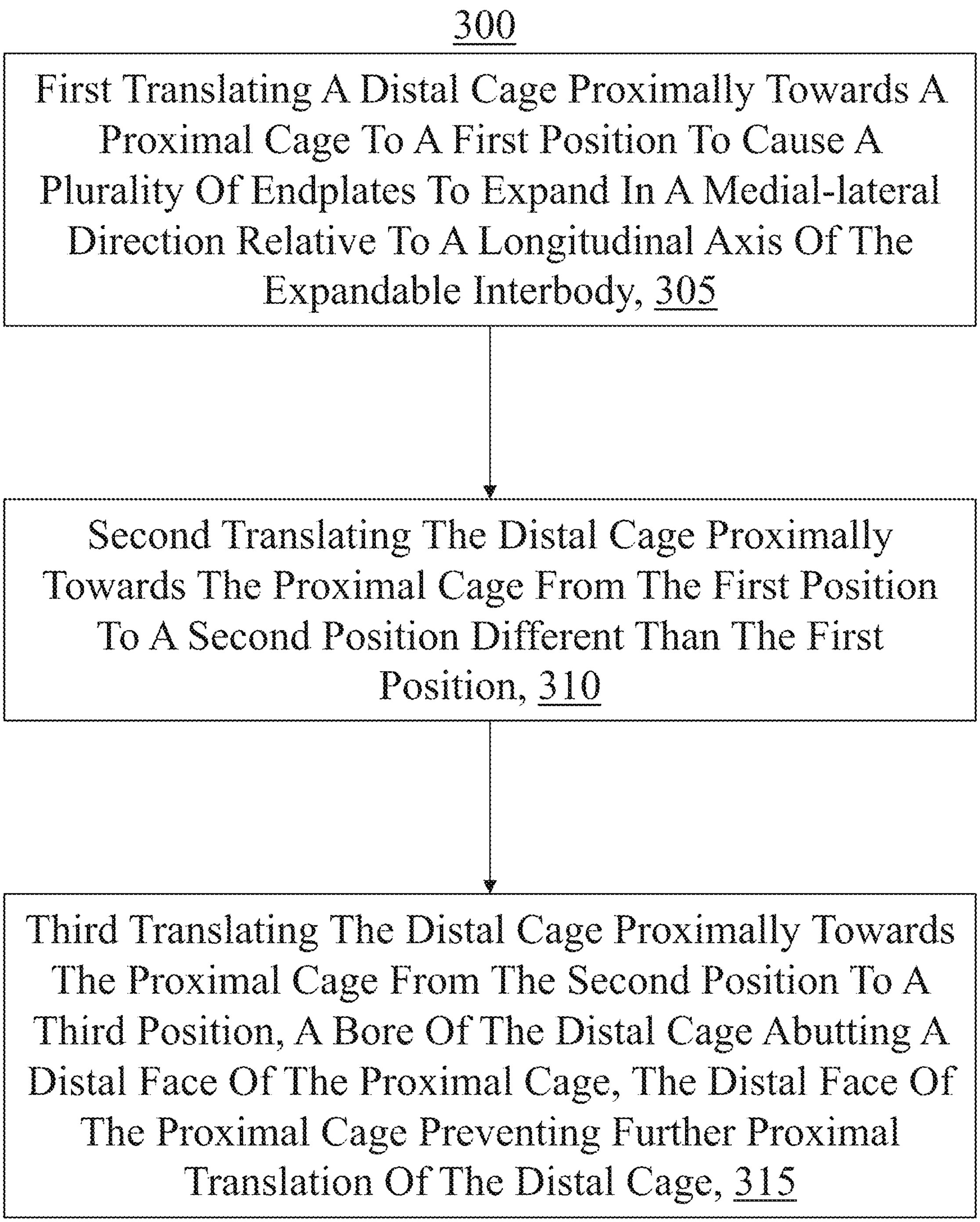
FIG. 28 is a flowchart of an illustrative method.

FIG. 28 is a flowchart of an example method 300 of expanding an expandable interbody implant, such as the expandable interbody implant 100 of FIGS. 1 through 16. The method 300 may include first translating a distal cage proximally towards a proximal cage to a first position to cause a plurality of endplates to expand in a medial-lateral direction relative to a longitudinal axis of the expandable interbody, at 305. The distal cage may be the distal cage 10 and the plurality of endplates may be incorporated into the top expandable assembly 20A and the corresponding bottom expandable assembly 20B. The method 300 may also include second translating the distal cage proximally towards the proximal cage from the first position to a second position different than the first position, at 310.

Translating the distal cage towards the proximal cage to the second position allows a locking hook or hook portion of a top distal ramp to clear a channel defined in a distal end of a first bottom endplate, and a locking hook of a bottom distal ramp to clear a channel defined in a distal end of a first top endplate. For example, referring briefly to FIGS. 9 and 11, the hook portion 37A of the top distal ramp 33A clears the channel 32B in the first bottom endplate 21B. Similarly, the hook portion 37B of the bottom distal ramp 33B clears the channel 32A in the first top endplate 21A.

Additionally, translating the distal cage towards the proximal cage to the second position causes: the top distal ramp to slide along the distal cage to achieve a desired lordosis (e.g., the ramped surface 44 slides along the top ramp 14 and the ramp portion 39 slides within the slot 15); a first projection of the proximal cage to clear a channel defined in a proximal end of the first bottom endplate (e.g., projection 61P clears the channel created by cut-out 29); and a second projection of the proximal cage to clear a channel defined in a proximal end of a second bottom endplate (e.g., projection 61P clears the channel created by cut-out 29).

The method 300 may additionally include third translating the distal cage proximally towards the proximal cage from the second position to a third position, a proximal extension of the distal cage abutting a stop of the proximal cage, the stop of the proximal cage preventing further proximal translation of the distal cage. Specifically, the proximal extension 18 of the distal cage 10 may abut the stop 65 of the proximal cage 60, preventing further proximal movement of the distal cage 10. The third translating may cause a top proximal ramp to slide along the proximal cage in a cranial-caudal direction, such that a protrusion of the first bottom endplate slides within a groove defined in a proximal extension of a second top endplate, thereby allowing the first bottom endplate to vertically separate from the second top endplate.

Referring briefly to FIG. 13, the protrusion 28B of the proximal extension 26B of the first bottom endplate 21B slides along and within the groove 27A defined in the proximal extension 26A of the second top endplate 22A. Similarly, the protrusion 28A of the proximal extension 26A of the first top endplate 21A slides along and within the groove 27B defined in the proximal extension 26B of the second bottom endplate 22B. As the protrusions 28A, 28B slide within the grooves 27A, 27B, the top expandable assembly 20A is moved vertically away from the bottom expandable assembly 20B.

First translating a distal cage proximally towards a proximal cage to a first position may include engaging internal threading of the distal cage with a distal end of a drive screw and engaging internal threading of the proximal cage with a proximal end of the drive screw. The internal threading of the proximal cage may be different from the internal threading of the distal cage. First translating may also include actuating the drive screw in a first direction, such that the distal cage is translated proximally towards the proximal cage.

Expanding a plurality of endplates in a medial-lateral direction may include sliding a proximal channel defined in the proximal end of the first bottom endplate along a first projection of a bottom proximal ramp and sliding a proximal channel defined in a proximal end of a second bottom endplate along a second projection of the bottom proximal ramp. Expanding the plurality of endplates in the medial-lateral direction may also include sliding a proximal channel defined in a proximal end of the first top endplate along a projection of the top proximal ramp and sliding a proximal channel defined in a proximal end of the second top endplate along a projection of the top proximal ramp. The first bottom endplate and the second bottom endplate may move away from each other, and similarly, the first top endplate and the second top endplate may move away from each other.

Second translating the distal cage proximally towards the proximal cage from the first position to a second position different from the first position may include engaging a ramp of the distal cage (e.g., the top ramp 14) with a ramp portion (e.g., ramp portion 39 at the bottom edge 38 of the top distal ramp 33A) of the top distal ramp. The ramp portion may have opposing edges, wherein each opposing edge includes a straight portion and a curved portion, the curved portion abuts the distal cage and the straight portion does not abut the distal cage. Second translating may also include driving the distal cage proximally towards the proximal cage, such that the straight portion of the ramp portion abuts the distal cage and the straight portion of the opposing edges is parallel to the ramp of the distal cage. Additionally, second translating may include moving the straight portion of the opposing edges along the distal cage, until the curved portion of the opposing edges extends beyond the distal cage. The straight portion of the opposing edges remains parallel to the ramp of the distal cage.

Figure 29:
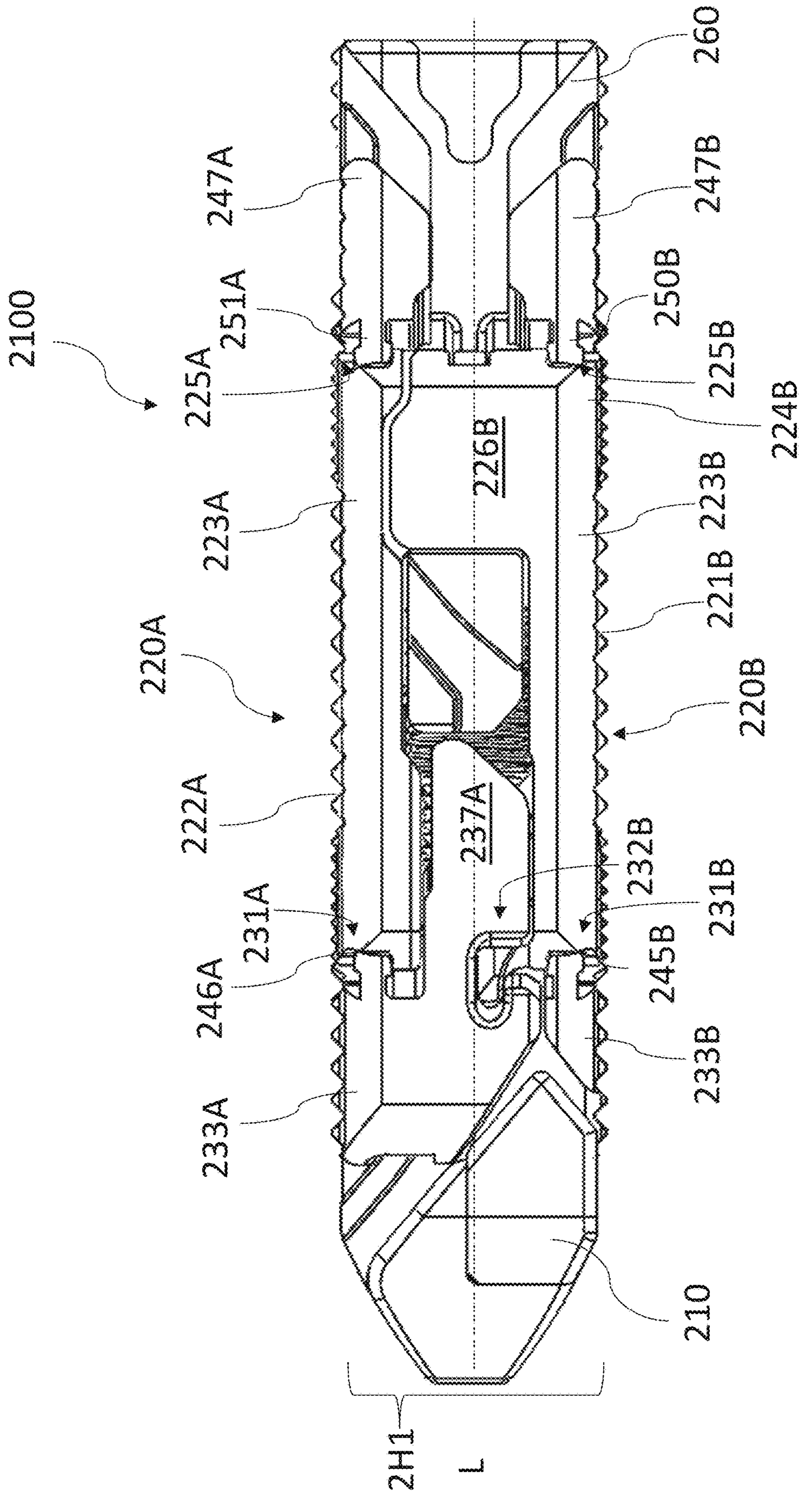
FIG. 29 is a side view of another configuration of an expandable interbody implant in a fully collapsed configuration.
Figure 30:
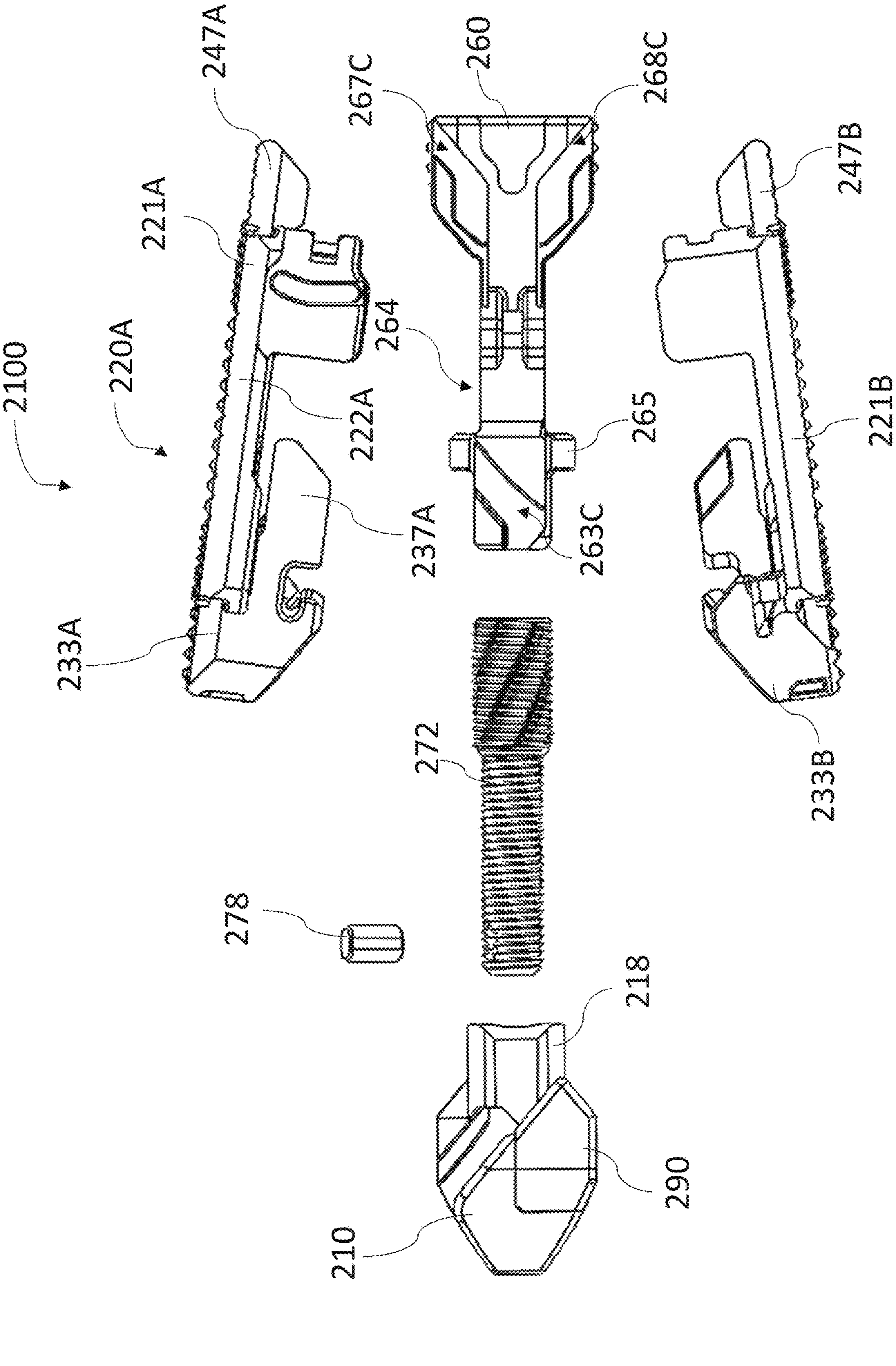
FIG. 30 is a side exploded view of the expandable interbody implant of FIG. 29.
Figure 31:
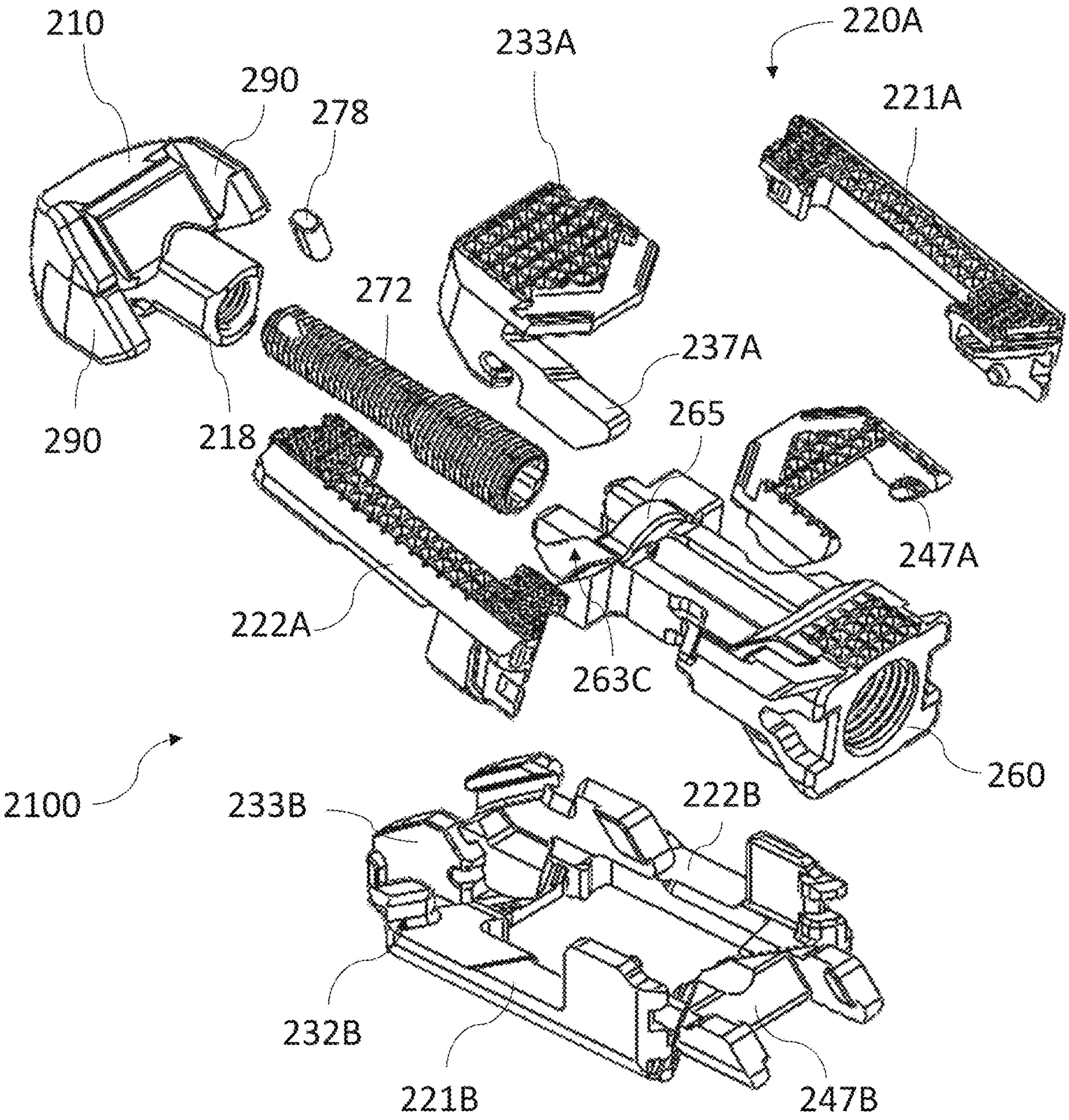
FIG. 31 is a perspective exploded view of the expandable interbody implant of FIG. 29.

FIGS. 29 through 31 illustrate another configuration of an expandable interbody implant 2100 in a fully collapsed configuration. Similar to the expandable interbody implant 100, the expandable interbody implant 2100 includes a distal cage 210, a top expandable assembly 220A, a proximal cage 260, and a bottom expandable assembly 220B. The distal cage 210 is mechanically connectable to the proximal cage 260 through a dual-threaded drive screw 272. The bottom expandable assembly 220B is identical or substantially identical to the top expandable assembly 220A, and is diagonally symmetrical to the top expandable assembly 220A about a longitudinal axis L of the expandable interbody implant 2100. In some configurations, the dual-threaded drive screw 272 interfaces with an insert 278 that provides torsional resistance for the dual-threaded drive screw 272. For example, a distal end 276 (see FIGS. 43A and 43B) of the drive screw 272 defines a bore 279 that receives the insert 278. The insert 278 is not threaded and rubs against the threads of the bore 279. In this way, the insert 278 provides torsional resistance to the dual-headed drive screw 272. In some embodiments, the insert 278 is formed from a thermoplastic (such as PEEK, or any other suitable high-performance thermoplastic), or the insert 278 can be formed from any other suitable material for providing torsional resistance. In other configurations, the insert may optionally be threaded or have a geometry for optimizing the desired torsional resistance.

The expandable interbody implant 2100 is expandable in at least three (3) directions. Firstly, the expandable interbody implant 2100 is expandable in a medial-lateral direction or a planar direction to increase the width of the expandable interbody implant 2100. Secondly, the expandable interbody implant 2100 is expandable in a lordotic direction or an angular direction. Thirdly, the expandable interbody implant 2100 is expandable in a cranial-caudal direction or a vertical direction to increase the height of the expandable interbody implant 2100. Translation of the distal cage 210 towards the proximal cage 260 facilitates expansion of the expandable interbody implant 2100 in each of the three directions. Additionally, each of the top expandable assembly 220A and the bottom expandable assembly 220B expands in the three directions.

The top expandable assembly 220A includes a first top endplate 221A, a second top endplate 222A adjacent to the first top endplate 221A in the collapsed configuration, a top distal pivot or ramp 233A and a top proximal pivot or ramp 247A. The top distal ramp 233A interfaces with and engages a surface (e.g., a top surface or other surface) of the distal cage 210. Likewise, the top proximal ramp 247A interfaces with and engages a surface (e.g., a top surface or other surface) of the proximal cage 260. For example, portions of the top proximal ramp 247A interface with and engage a top channel 263C' defined by the proximal cage 260. Similarly, portions of the bottom proximal ramp 247B interface with and engage a bottom channel 263C" defined by the proximal cage 260. Each of the first top endplate 221A and the second top endplate 222A has a body 223A extending between a proximal end 224A and a distal end 230A. The proximal end 224A interfaces with and engages the top proximal pivot or ramp 247A and the distal end 230A interfaces with and engages the top distal pivot or ramp 233A. The proximal end 224A of the first top endplate 221A and the second top endplate 222A also includes a proximal extension 226A that interfaces with and engages a corresponding proximal extension 226B of the first bottom endplate 221B or the second bottom endplate 222B as discussed in more detail below.

For example, the proximal end 224A of both the first top endplate 221A and the second top endplate 222A defines a channel 225A for engaging a first projection 250A or a second projection 251A of the top proximal ramp 247A. Similarly, the distal end 230A of both the first top endplate 221A and the second top endplate 222A defines a channel 231A for engaging a first projection 245A or a second projection 246A of the top distal ramp 233A.

The bottom expandable assembly 220B is identical to the top expandable assembly 220A (but diagonally symmetrical) and includes all of the same components as the top expandable assembly 220A. That is, the bottom expandable assembly 220B includes a first bottom endplate 221B, a second bottom endplate 222B adjacent to the first bottom endplate 221B, a bottom distal pivot or ramp 233B and a bottom proximal pivot or ramp 247B. Because of the diagonal symmetry, the first bottom endplate 221B is identical to the second top endplate 222A, and the second bottom endplate 222B is identical to the first top endplate 221A. The bottom distal ramp 233B interfaces with and engages a surface (e.g., a bottom surface) of the distal cage 210. Likewise, the bottom proximal ramp 247B interfaces with and engages a surface (e.g., a bottom surface) of the proximal cage 260. Each of the first bottom endplate 221B and the second bottom endplate 222B has a body 223B extending between a proximal end 224B and a distal end 230B. The proximal end 224B interfaces with and engages the bottom proximal pivot or ramp 247B and the distal end 230B interfaces with and engages with the bottom distal pivot or ramp 233B.

Additionally, as with the top expandable assembly 220A, the proximal end 224B of both the first bottom endplate 221B and the second bottom endplate 222B defines a channel 225B for engaging a first projection 250B or a second projection 251B of the bottom proximal ramp 247B. Similarly, the distal end 230B of both the first bottom endplate 221B and the second bottom endplate 222B defines a channel 231B for engaging a first projection 245B or a second projection 246B of the bottom distal ramp 233B. The proximal end 224B of the first bottom endplate 221B and the second bottom endplate 222B also includes a proximal extension 226B that interfaces with and engages with a corresponding proximal extension 226A of the first top endplate 221A or the second top endplate 222A.

Figure 39A:
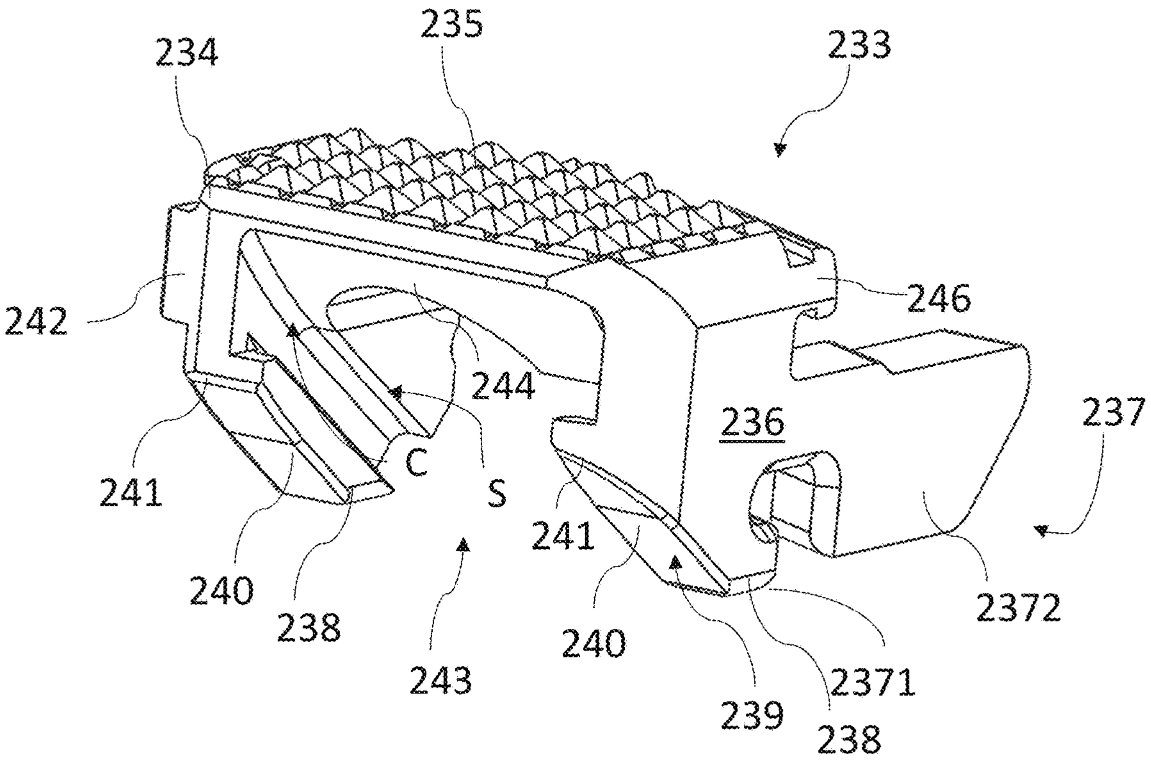
FIG. 39A illustrates a distal perspective view and FIG. 39B illustrates a proximal perspective view of the distal pivot or ramp from the expandable interbody implant of FIGS. 29 through 36.
Figure 39B:
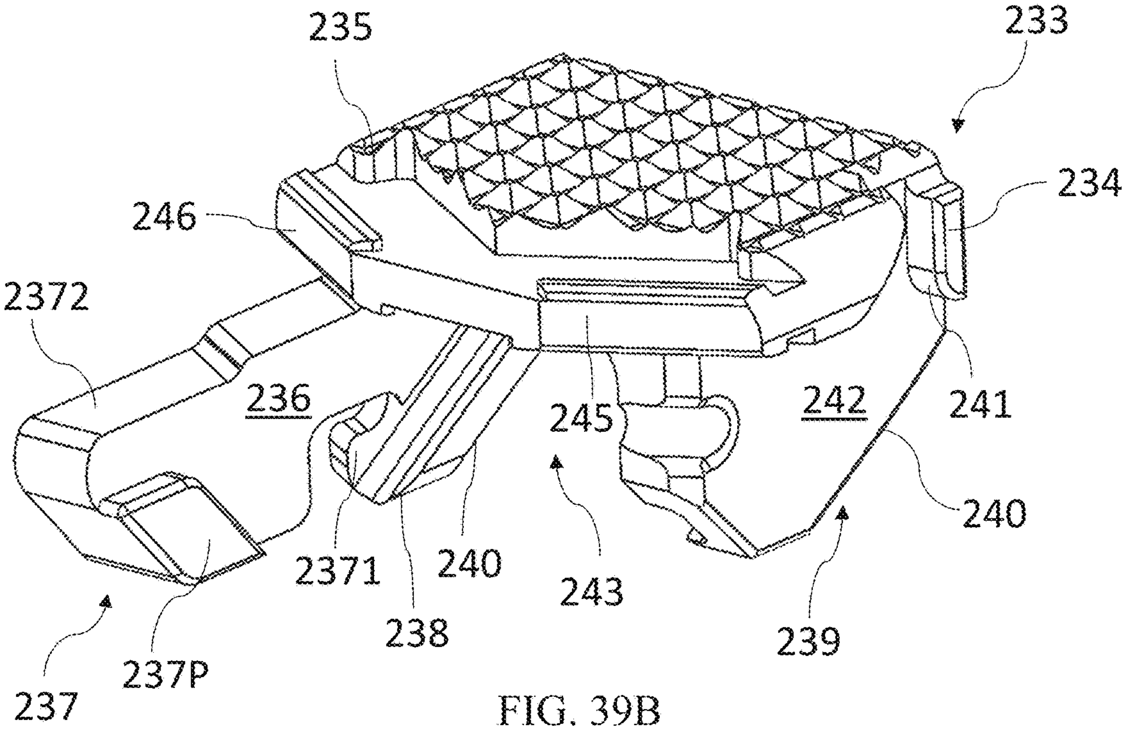

A portion of the top distal ramp 233A of the top expandable assembly 220A is connected to the first bottom endplate 221B of the bottom expandable assembly 220B. Specifically, a hook portion 237A of the top distal ramp 233A is connected to and engaged by a channel 232B defined in the distal end 230B of the first bottom endplate 221B. As the bottom expandable assembly 220B is identical to the top expandable assembly 220A, the bottom distal ramp 233B of the bottom expandable assembly 220B also includes a hook portion 237B that is connected to and engaged by a channel 232A defined in the distal end 230A of the first top endplate 221A. Referring briefly to FIGS. 39A and 39B, where a ramp 233 (e.g., either the top distal ramp 233A or the bottom distal ramp 233B) is illustrated, the hook portion 237 of the ramp 233 includes a first hook portion 2371 and a second hook portion 2372. The first hook portion 2371 engages the channel 232A or 232B of the first top endplate 221A or the first bottom endplate 221B, respectively. The second hook portion 2372 includes a projection 237P that engages with a channel 263C defined by the proximal cage 260. Engagement of the projection 237P with the channel 263C improves stability of the expandable interbody implant 2100 in the collapsed configuration. Additionally, as the expandable interbody implant 2100 moves through the first medial-lateral direction, the second lordotic or angular direction, and the third cranial-caudal direction, the projection 237P slides within the channel 263C on either side of the proximal cage 260, thereby stabilizing the expandable interbody implant 2100 as the expandable interbody implant 2100 moves through each of the three configurations.

The expandable interbody implant 2100 is diagonally symmetrical about the longitudinal axis L of the expandable interbody implant 2100. That is, the bottom expandable assembly 220B is identical to the top expandable assembly 220A rotated 180°. As such, the first top endplate 221A sits on top of and engages the second bottom endplate 222B. Likewise, the second top endplate 222A sits on top of and engages the first bottom endplate 221B.

Figure 32A:
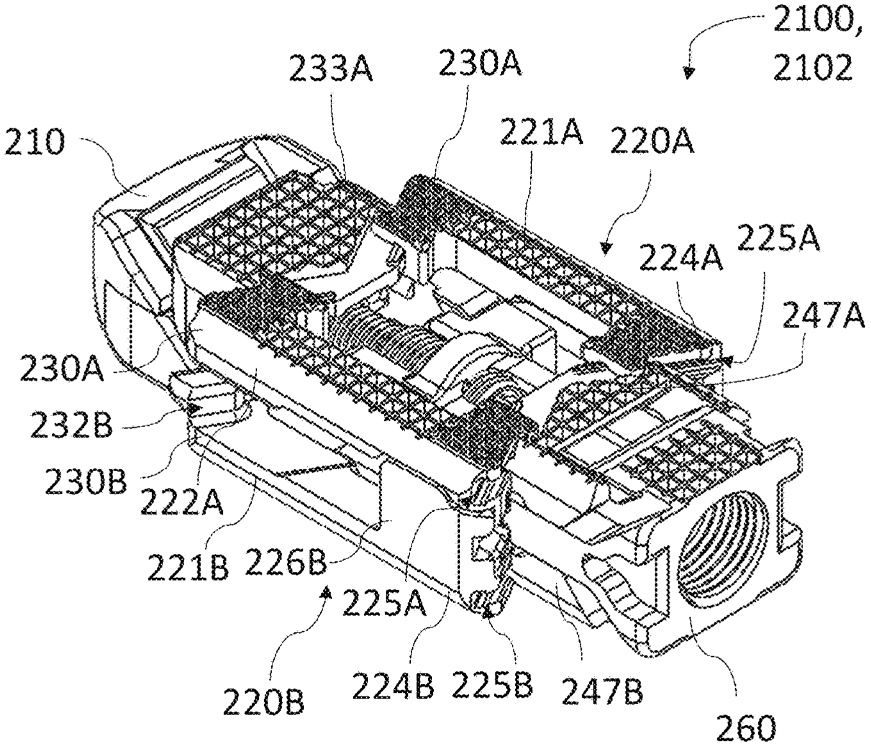
FIG. 32A is a perspective view of the expandable interbody implant of FIG. 29 in a first medial-lateral expanded configuration.
Figure 32B:
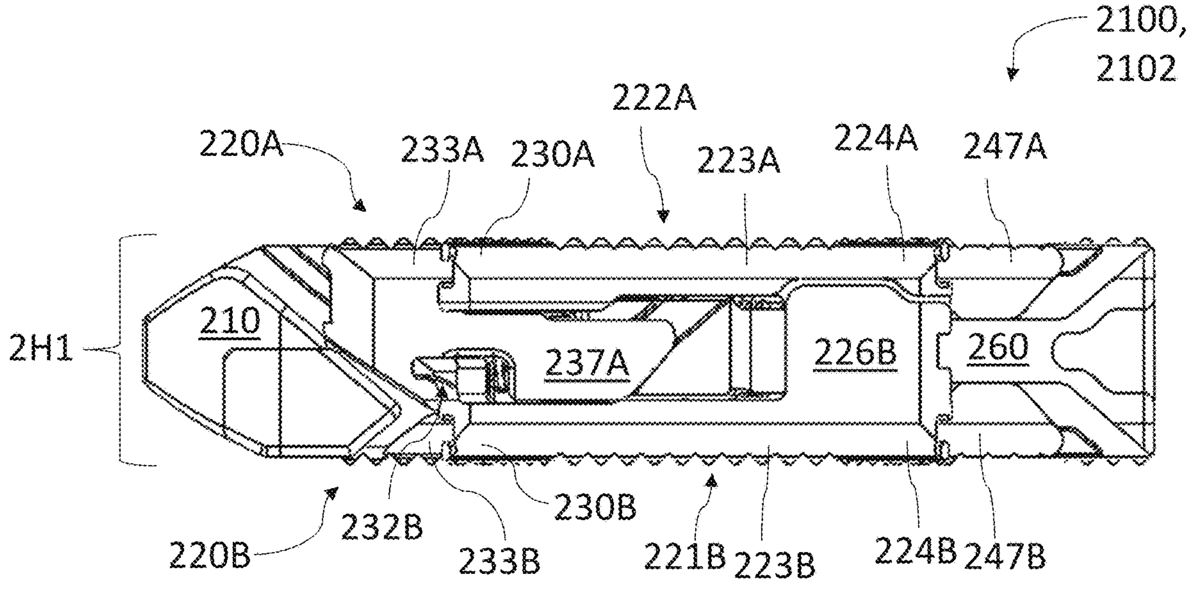
FIG. 32B illustrates a side view of the expandable interbody implant of FIG. 32A in the first medial-lateral expanded configuration.

FIGS. 32A and 32B illustrate views of the expandable interbody implant 2100 of FIGS. 29 through 31 in a first medial-lateral expanded configuration 2102 to increase the width of the implant 2100. Components from each of the top expandable assembly 220A and the bottom expandable assembly 220B expand in the medial-lateral direction. The distal cage 210 is driven or translated proximally towards the proximal cage 260 to a first position via action of the drive screw 272. Upon translation of the distal cage 210 proximally towards the proximal cage 260, the interbody 2100 expands laterally, with the first top endplate 221A and second top endplate 222A moving outwardly and away from each other, and similarly the first bottom endplate 221B and second bottom endplate 222B move outwardly and away from each other. To enable this outward movement of the endplates, slots and channels are provided at the distal and proximal ends. In one configuration, four slots/channels are provided in each of the distal and proximal ends.

At the distal end, the projection 246A of the top distal ramp 233A slides within channel 231A of the second top endplate 222A at the distal end, and the projection 246B of the bottom distal ramp 233B slides within the channel 231B of the first bottom endplate 221B at the distal end. Similarly, the projection 245A of the top distal ramp 233A slides within channel 231A of the first top endplate 221A at the distal end, and the projection 245B of the bottom distal ramp 233B slides within the channel 231B of the second bottom endplate 222B. However, the top distal ramp 233A and the bottom distal ramp 233B experience substantially no movement or sliding relative to the distal cage 210. That is, the top distal ramp 233A and the bottom distal ramp 233B stay substantially static relative to the distal cage 210, with the first top endplate 221A, the second top endplate 222A, the first bottom endplate 221B, and the second bottom endplate 222B moving in the medial-lateral direction.

At the proximal end, the proximal channel 225A at the proximal end 224A of the first top endplate 221A slides along the first projection 250A of the top proximal ramp 247A. Identically, the proximal channel 225A at the proximal end 224A of the second top endplate 222A slides along the second projection 251A of the top proximal ramp 247A. In this way, the first top endplate 221A and the second top endplate 222A may expand laterally away from a mid-line of the implant 2100 and away from each other. However, the top proximal ramp 247A and the bottom proximal ramp 247B experience substantially no movement or sliding relative to the proximal cage 260. That is, the top proximal ramp 247A and the bottom proximal ramp 247B stay substantially static relative to the proximal cage 260, with the first top endplate 221A, the second top endplate 222A, the first bottom endplate 221B, and the second bottom endplate 222B moving in the medial-lateral direction.

Similarly, the proximal channel 225B at the proximal end 224B of the first bottom endplate 221B slides along the first projection 250B of the bottom proximal ramp 247B. Identically, the proximal channel 225B at the proximal end 224B of the second bottom endplate 222B slides along the second projection 251B of the bottom proximal ramp 247B and the distal channel 231B in the distal end 230A of the second bottom endplate 222B slides along the second projection 246B of the bottom distal ramp 233B. In this way, the first bottom endplate 221B and the second bottom endplate 222B may expand laterally away from a mid-line of the implant 2100 and away from each other.

When the first bottom endplate 221B expands in the medial-lateral direction, the hook portion 237A of the top distal ramp 233A clears the channel 232B in the distal end 230B of the first bottom endplate 221B. Similarly, when the first top endplate 221A expands in the medial-lateral direction, the hook portion 237B of the bottom distal ramp 233B clears the channel 232A in the distal end 230A of the first top endplate 221A. This clearance of the hook portions 237A, 237B allows for further expansion of the implant 2100. In other words, the hook portions 237A, 237B, interact with the channels of the end plates to constrain movement of the endplates to the medial-lateral direction only until the hook portions 237A, 237B clear the channels. Additionally, as the hook portions 237A, 237B clear the channels 232A, 232B, the projections 237P of each ramp (e.g., of the top distal ramp 233A and the bottom distal ramp 233B) slide within the channels 263C of the proximal cage 260. The projections 237P remain engaged within the channels 263C, thereby stabilizing the expandable interbody implant 2100 during expansion in the first medial-lateral direction.

The proximal extension 226A (not visible in FIGS. 32A and 32B) of the second top endplate 222A is mechanically engaged with the proximal extension 226B of the first bottom endplate 221B. Together, the proximal extensions 226A and 226B define or create a cut-out 229 (see FIGS. 42A and 42B) that engages a projection 261P of the proximal cage 260 (see FIGS. 38A and 38B). When the top expandable assembly 220A and the bottom expandable assembly 220B expand in the medial-lateral direction, the projection 261P begins to clear the cut-out 229, allowing for additional expansion in the second top endplate 222A and the first bottom endplate 221B. A similar relationship and cut-out 229 is formed between the first top endplate 221A and the second bottom endplate 222B.

Little to no vertical gain is realized in the medial-lateral expanded configuration. Accordingly, the implant 2100 has a height 2H1 when the implant is expanded in the medial-lateral or first direction, which is substantially the same height as when the implant 2100 is fully collapsed, as in FIGS. 29 through 31. 2H1 may range from about 7 mm to about 9 mm, such as 7 mm, 7.5 mm, 8 mm, 8.5 mm, 9 mm, etc.

Figure 33:
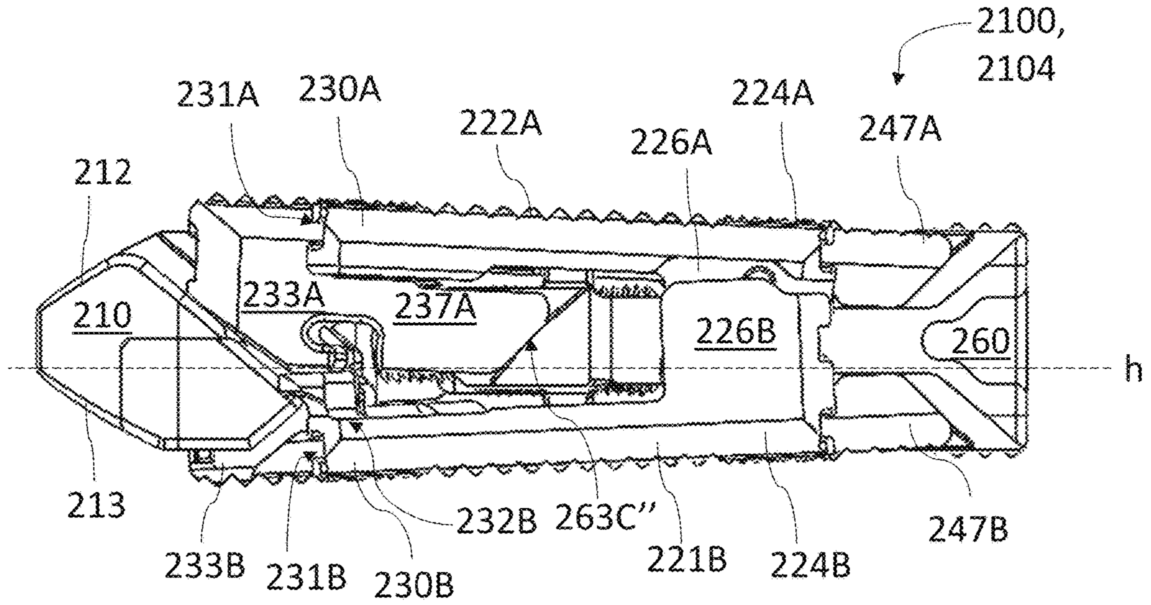
FIG. 33 illustrates a side view of the expandable interbody implant of FIG. 29 in a second lordotic or angular expanded configuration.
Figure 34:
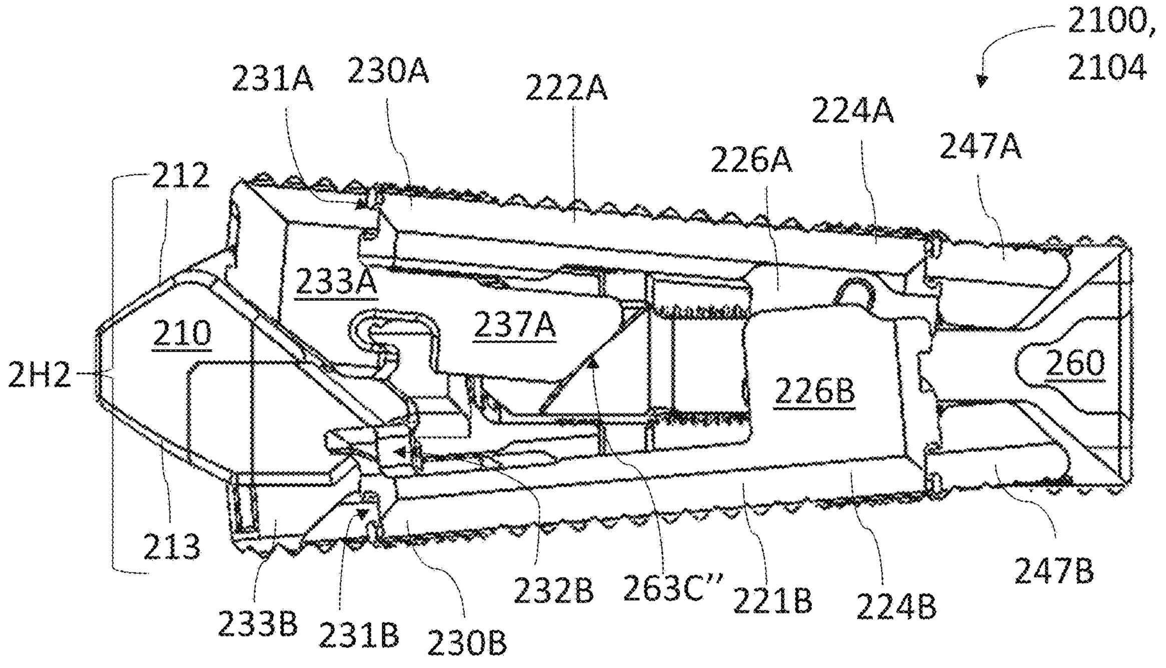
FIG. 34 illustrates a side view of the expandable interbody implant of FIG. 33 in the second lordotic or angular expanded configuration, relatively more expanded compared to FIG. 33.

FIGS. 33 and 34 illustrate side views of the expandable interbody implant of FIGS. 29 through 31 in a second lordotic or angular expanded configuration 2104. The medial-lateral expansion of the top expandable assembly 220A and the bottom expandable assembly 220B is maintained throughout the lordotic or angular expansion. Components from each of the top expandable assembly 220A and the bottom expandable assembly 220B expand in the lordotic or angular direction. The distal cage 210 is driven or translated proximally towards the proximal cage 260 to a second position via further action of the drive screw 272. Upon translation of the distal cage 210 proximally towards the proximal cage 260, the top expandable assembly 220A and the bottom expandable assembly 220B are vertically expanded away from each other until each of the top expandable assembly 220A and the bottom expandable assembly 220B are disposed at a desired angle relative to the horizontal (h). The desired angle may range from about 7° to about 20°, such as about 7.5°, 8°, 10°, 12°, 15°, 18°, or an angle within a range defined by any two of the foregoing values.

Figure 35:
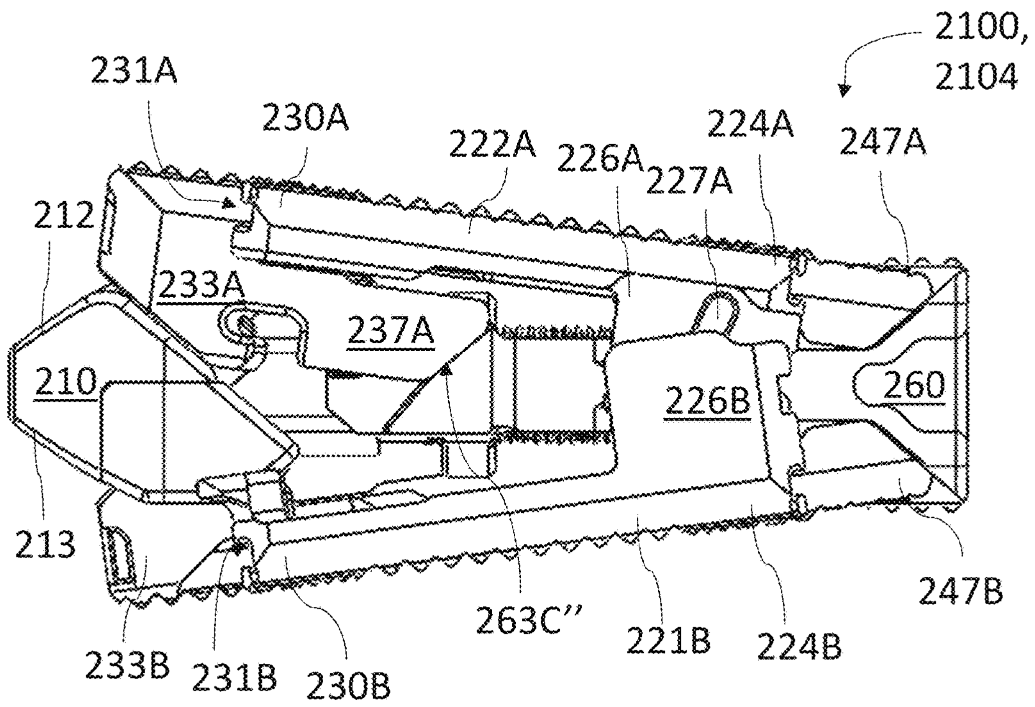
FIG. 35 illustrates a side view of the expandable interbody implant of FIG. 33 in the second lordotic or angular expanded configuration, relatively more expanded compared to FIG. 34.

As the distal cage 210 is driven or translated proximally towards the proximal cage 260, the top distal ramp 233A (and the bottom distal ramp 233B) slides along the surface of the distal cage 210. Referring briefly to FIGS. 39A and 39B, in which a ramp 233 is illustrated, the top distal ramp 233A (and the bottom distal ramp 233B) includes a first sidewall 236 which includes the hook portion 237 and a ramp portion 239. The ramp portion 239 includes a straight portion 240 and a curved portion 241. Referring now to FIGS. 33, 34, and 35, together with FIGS. 39A and 39B, as the top distal ramp 233A (and the bottom distal ramp 233B) continues to slide along the surface of the distal cage 210, the straight portion 240 of the ramp portion 239 becomes parallel to the surface of the distal cage 210.

When the implant 2100 is in the collapsed configuration and/or the medial-lateral expansion configuration 2102, the straight portion 240 of the ramp portion 239 is not parallel to and not in contact with the distal cage 210. However, as the distal cage 210 is driven proximally towards the proximal cage 260 to the second position, the straight portion 240 of the ramp portion 239 becomes parallel to and abuts the surface of the distal cage 210. This connection between the straight portion 240 of the ramp portion 239 and the distal cage 210 facilitates disposition of the top expandable assembly 220A in the desired angle. As translation of the distal cage 210 towards the proximal cage 260 continues, the straight portion 240 of the ramp portion 239 of the top distal ramp 233A (and the bottom distal ramp 233B) will continue to slide along the distal cage 210.

Figure 40A:
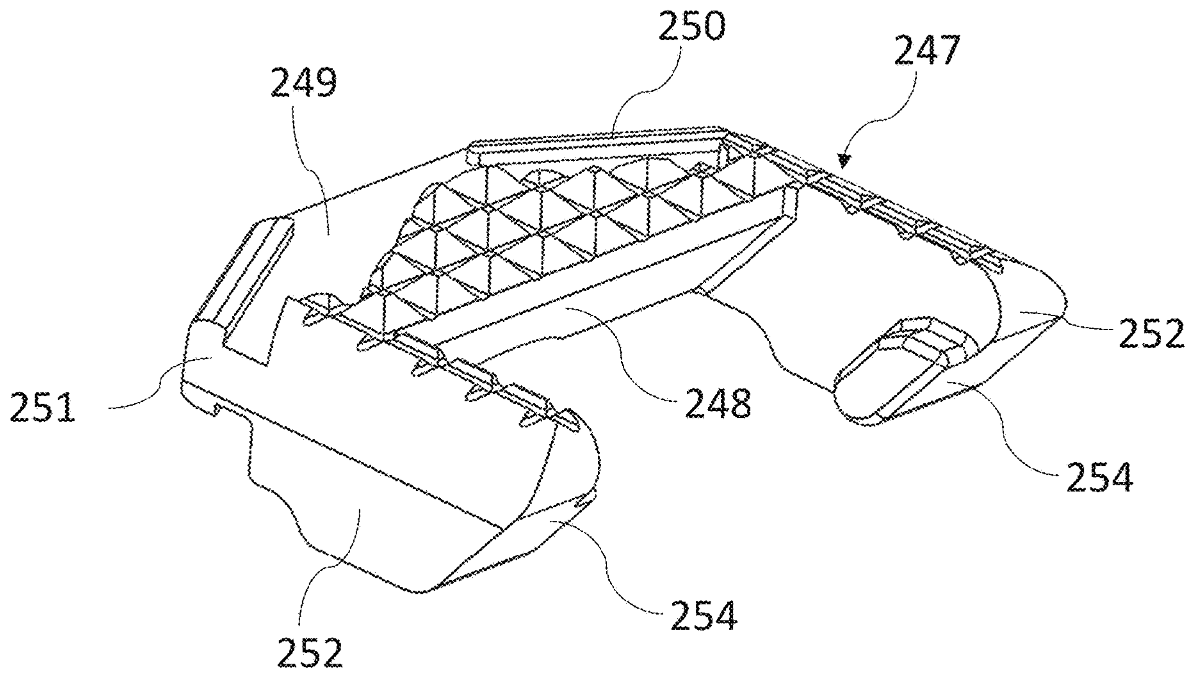
FIG. 40A illustrates a top, proximal perspective view
Figure 40B:
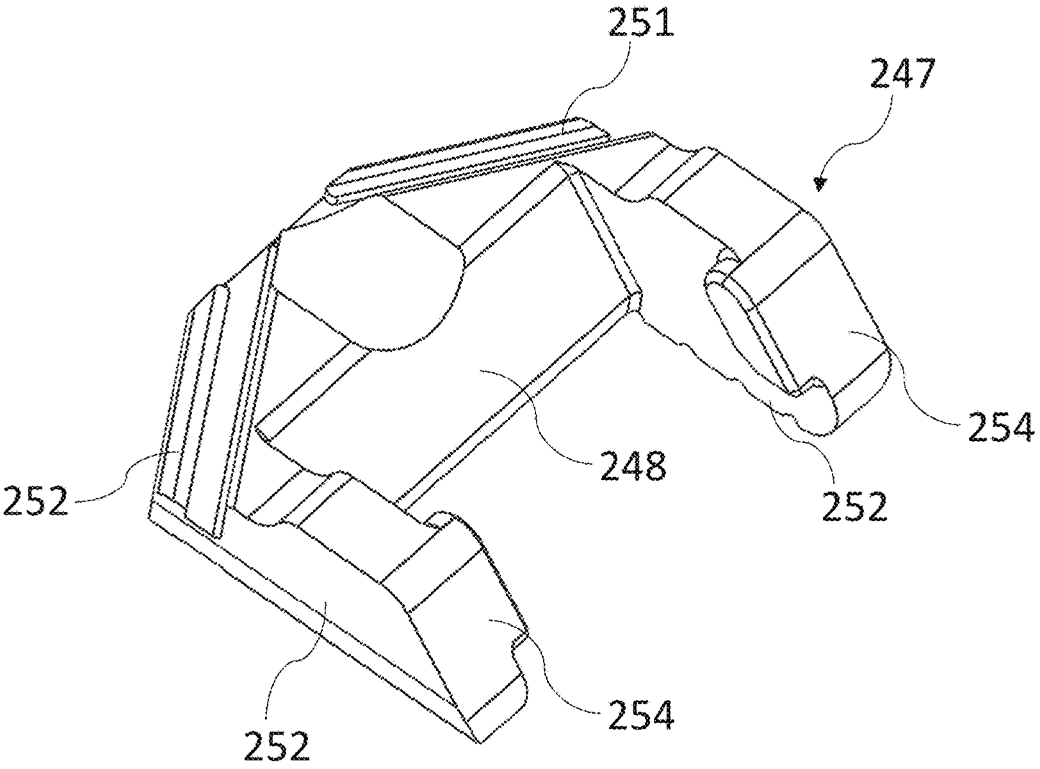
FIG. 40B illustrates a bottom, proximal perspective view of the proximal pivot or ramp from the expandable interbody implant of FIGS. 29 through 36.

A similar alignment occurs with the proximal ramps 247 (e.g., the top proximal ramp 247A and the bottom proximal ramp 247B) and the proximal cage 260. Referring briefly to FIGS. 40A and 40B, which illustrate a proximal ramp 247, the top proximal ramp 247A includes lateral wings 252 extending from a body 248. The lateral wings 252 each include a ramp portion 254 which interfaces with and engages the proximal cage 260. When the implant 2100 is in the medial-lateral expansion configuration 2102, the ramp portion 254 of the top proximal ramp 247A is not parallel to the proximal cage 260. However, as the distal cage 210 is driven proximally towards the proximal cage 260 to the second position, the ramp portion 254 of the top proximal ramp 247A becomes parallel to and abuts the surface of the proximal cage 260.

Clearance of the hook portion 237A from the channel 232B in the first bottom endplate 221B allows for the lordotic or angular expansion of the top and bottom expandable assemblies 220A and 220B. Specifically, clearance of the hook portion 237A from the channel 232B in the first bottom endplate 221B allows the top distal ramp 233A to slide along the distal cage 210. Engagement by the projections 237P of each ramp (e.g., of the top distal ramp 233A and the bottom distal ramp 233B) within the channels 263C of the proximal cage 260 continues to stabilize the expandable interbody implant 2100 during expansion in the second lordotic or angular direction. The projection 237P of the top ramp 233A continues to slide within the channel 263C, towards the top expandable assembly 220A. The projection 237P of the bottom ramp 233B continues to slide within the channel 263C, towards the bottom expandable assembly 220B.

Additionally, clearance of the cut-out 229 by the projection 261P of the proximal cage 260 allows for the lordotic or angular expansion of the top and bottom expandable assemblies 220A and 220B. Specifically, clearance of the cut-out 229 by the projection 261P of the proximal cage 260 allows the proximal extension 226A of the second top endplate 222A to hingedly move away from the proximal extension 226B of the first bottom endplate 221B. Clearance of the cut-out 229 by the projection 261P of the proximal cage 260 also allows the ramp portion 254 of the lateral wings 252 of the top proximal ramp 247A to abut the surface of the proximal cage 260 and slide along the proximal cage 260.

As the top expandable assembly 220A is moved vertically away from the bottom expandable assembly 220B to the desired angle, the implant 2100 increases in height from 2H1 to 2H2. 2H2 may range from about 9.5 mm to about 12.5 mm, such as 10, 10.5, 11, 11.5, 12 mm, or a height within a range defined by any two of the foregoing values. Additionally, to enable the angular movement of the top endplate assembly 220A away from the bottom endplate assembly 220B, the proximal extension 226A of the second top endplate 222A defines a groove 227A in which a projection 228B of the first bottom endplate 221B (not illustrated, see FIG. 41B) slides and moves. As the top distal ramp 233A and the bottom distal ramp 233B slide along distal cage 210, the projection or protrusion 228B of the first bottom endplate 221B moves along the groove 227A, allowing the second top endplate 222A to be moved angularly with respect to the first bottom endplate 221B. Similarly, the first top endplate 221A moves angularly with respect to the second bottom endplate 222B.

Figure 36:
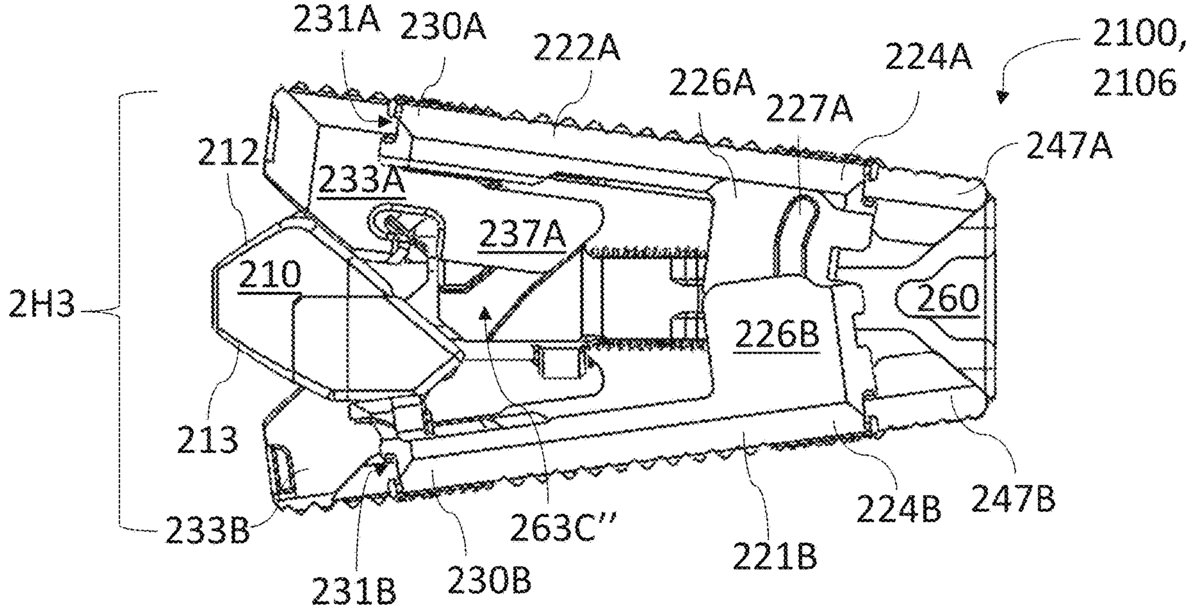
FIG. 36 illustrates a side view of the expandable interbody implant of FIG. 35 in a third cranial-caudal expanded configuration.

FIG. 36 illustrates a side view of the expandable interbody implant of FIG. 33 in a third cranial-caudal expanded configuration 2106. The medial-lateral expansion of the top expandable assembly 220A and the bottom expandable assembly 220B is maintained throughout the cranial-caudal or vertical expansion. The desired angle of the top expandable assembly 220A and the bottom expandable assembly 220B reached during the lordotic or angular expansion is also maintained throughout the cranial-caudal or vertical expansion.

Components from each of the top expandable assembly 220A and the bottom expandable assembly 220B expand in the cranial-caudal or vertical direction. The distal cage 210 is driven or translated proximally towards the proximal cage 260 to a third position via further action of the drive screw 272. In the third position, the distal cage 210 hits a stop 265 of the proximal cage 260 and cannot further move proximally. The distal cage 210 includes a proximal extension 218 that hits and abuts the stop 265 of the proximal cage 260, thereby arresting further proximal movement of the distal cage 210 towards the proximal cage 260. Upon translation of the distal cage 210 proximally towards the proximal cage 260, the top expandable assembly 220A and the bottom expandable assembly 220B are vertically expanded away from each other.

Specifically, each of the top distal ramp 233A and the bottom distal ramp 233B slide along respective surfaces (e.g., top surface 212 and bottom surface 213) of the distal cage 210. As the top distal ramp 233A and the bottom distal ramp 233B slide along distal cage 210, the top proximal ramp 247A and the bottom proximal ramp 247B slide along respective surfaces of the proximal cage 260. Additionally, the proximal extension 226A of the second top endplate 222A moves (e.g., in a hinge-type motion) along the proximal extension 226B of the first bottom endplate 221B vertically extending the endplates away from each other. The proximal extension 226A of the second top endplate 222A defines a groove 227A in which a projection 228B of the first bottom endplate 221B (not illustrated, see FIG. 41B) slides and moves. As the top distal ramp 233A and the bottom distal ramp 233B slide along distal cage 210, the projection or protrusion 228B of the first bottom endplate 221B slides along the groove 227A, allowing the second top endplate 222A to be moved vertically away from the first bottom endplate 221B.

The proximal extension 226A of the first top endplate 221A has the same hinged relationship with the proximal extension 226B of the second bottom endplate 222B. Specifically, the proximal extension 226A of the first top endplate 221A moves (e.g., in a hinge-type motion) vertically away from the proximal extension 226B of the second bottom endplate 222B. However, the second bottom endplate 222B defines a groove 227B through which a projection or protrusion 228A of the first top endplate 221A slides and moves.

As the top expandable assembly 220A is moved vertically away from the bottom expandable assembly 220B to the desired angle, the implant 2100 increases in height from 2H2 to 2H3. 2H3 may range from about 12.5 mm to about 17.5 mm, such as 13, 13.5, 14, 14.5, 15, 15.25, 15.5 mm, 16 mm, 16.5 mm, 17 mm, 17.5 mm, or a height within a range defined by any two of the foregoing values.

Figure 37A:
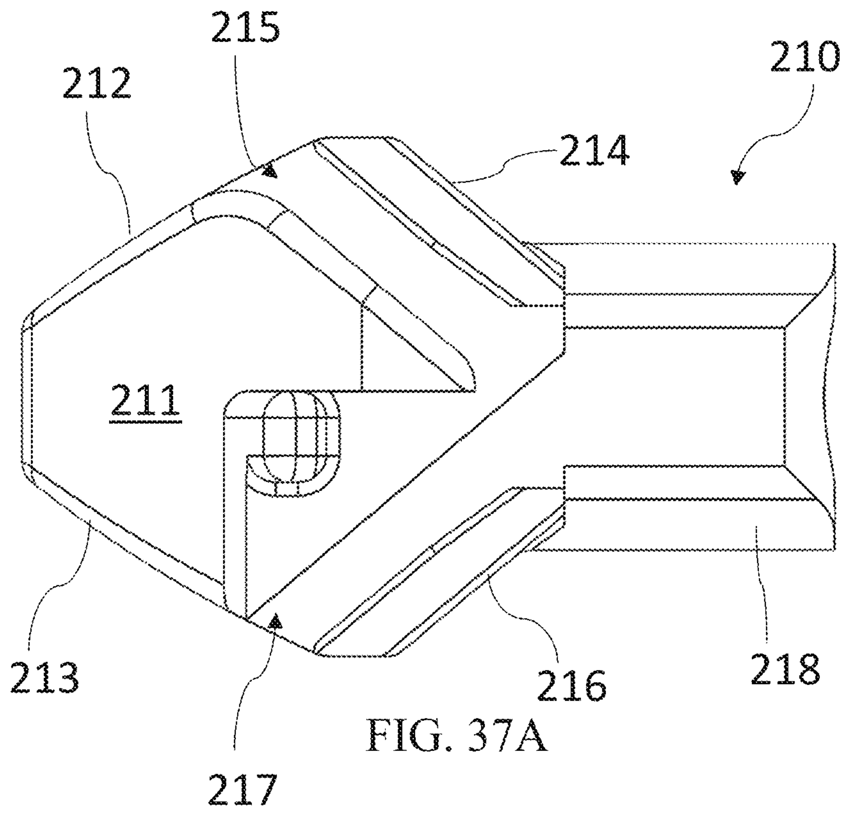
FIG. 37A illustrates a side view and FIG. 37B illustrates a proximal perspective view of the distal cage from the expandable interbody implant of FIGS. 29 through 36.
Figure 37B:
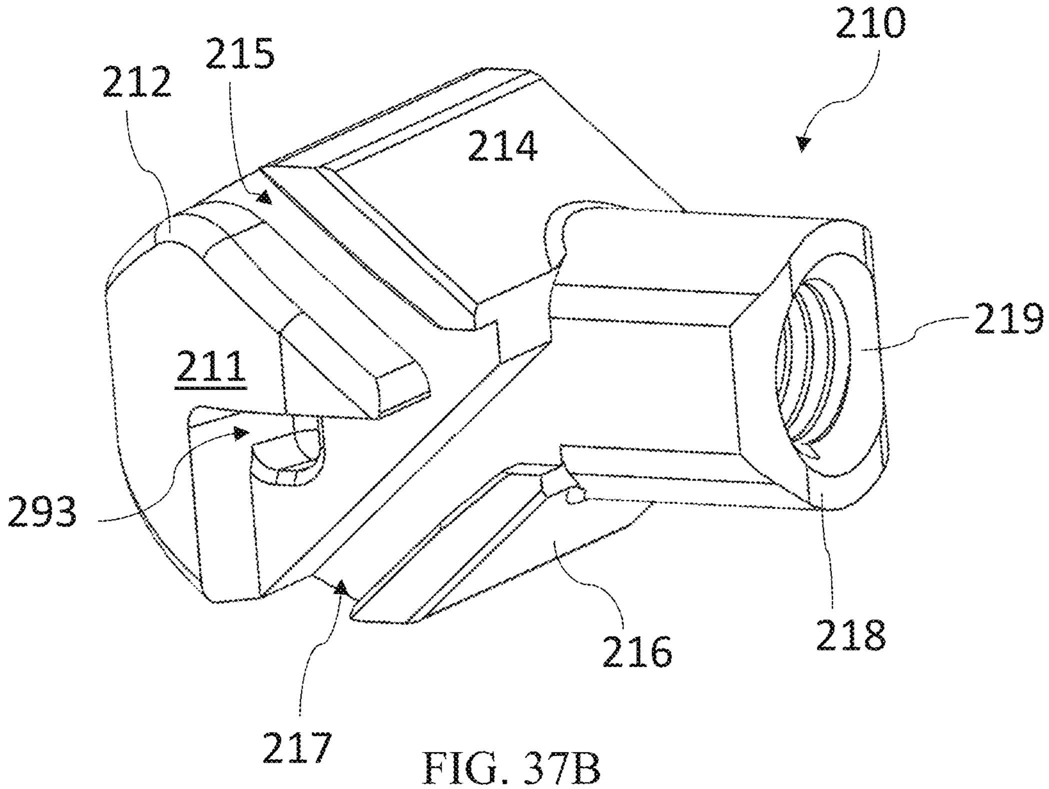

FIGS. 37A and 37B illustrate views of the distal cage 210 from the expandable interbody implant of FIGS. 29 through 36. The distal cage 210 includes a body 211 having a top surface 212 and a bottom surface 213 opposite the top surface 212. The body 211 may have a substantially diamond shape, where the top surface 212 tapers towards the bottom surface 213. In some embodiments, the body 211 may receive a cap 290, such as illustrated in FIGS. 44A and 44B. The cap may cover grooves of the distal cage 210 and may be welded onto the distal cage 210 during assembly. The body 211 also includes a proximal extension 218 that defines a threaded bore 219. The threaded bore 219 has threads that correspond to threadings at a distal end 276 of the drive screw 272 (see FIGS. 43A and 43B). The distal cage 210 is diagonally symmetrical about an axis A of the distal cage 210.

The top surface 212 of the body 211 includes a top ramp 214 and a top slot 215. The top surface 212 may taper towards the bottom surface 213 in an opposite direction of the top ramp 214. Similarly, the bottom surface 213 includes a bottom ramp 216 and a bottom slot 217. The top distal pivot or ramp 233A of the top expandable assembly 220A slides along the top ramp 214 of the distal cage 210 and engages the top slot 215. Similarly, the bottom distal pivot or ramp 233B of the bottom expandable assembly 220B slides along the bottom ramp 216 and engages the bottom slot 217. When the implant 2100 is in the lordotic expansion configuration 2104 and/or the cranial-caudal expansion configuration 2106, the straight portion 240 of the ramp portion 239 of the top distal ramp 233A is parallel to the top ramp 214 and the top slot 215. Likewise, the straight portion 240 of the ramp portion 239 of the bottom distal ramp 233B is parallel to the bottom ramp 216 and the bottom slot 217. As illustrated, the distal cage 210 additionally includes a void or hole 293 for engaging with a projection 292 of the cap 290. Such engagement may improve the connection between the distal cage 210 and the cap 290.

Figure 38A:
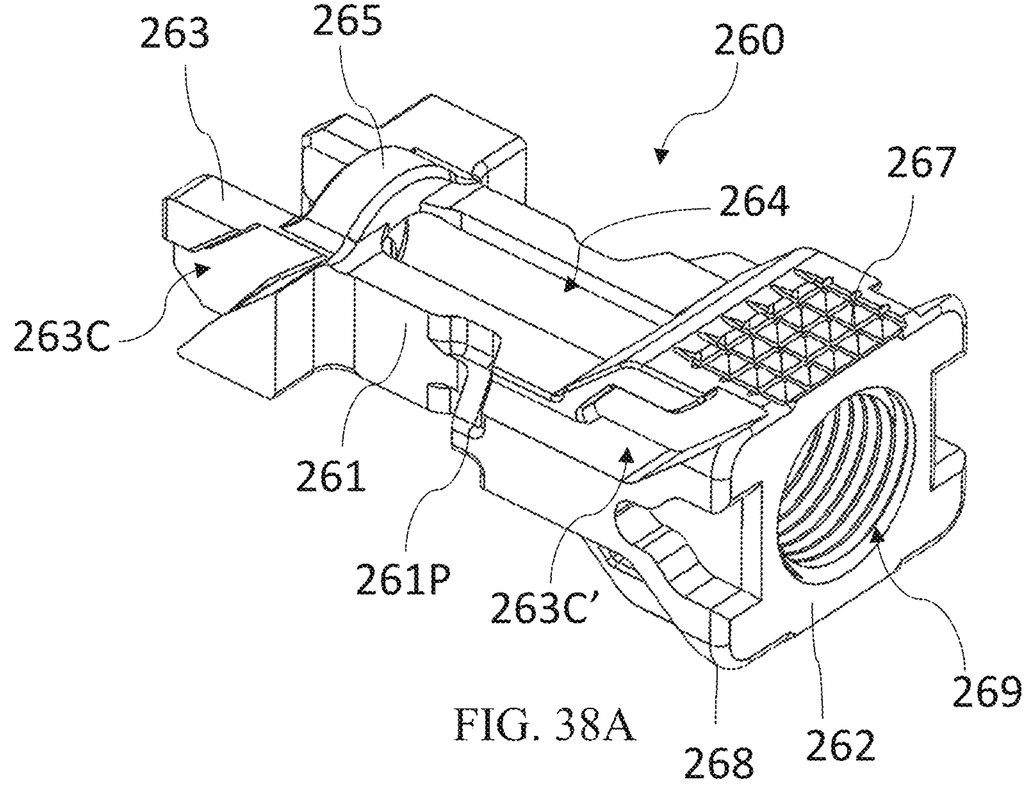
FIG. 38A illustrates a proximal perspective view and FIG. 38B illustrates a distal perspective view of the proximal cage from the expandable interbody implant of FIGS. 29 through 36.
Figure 38B:
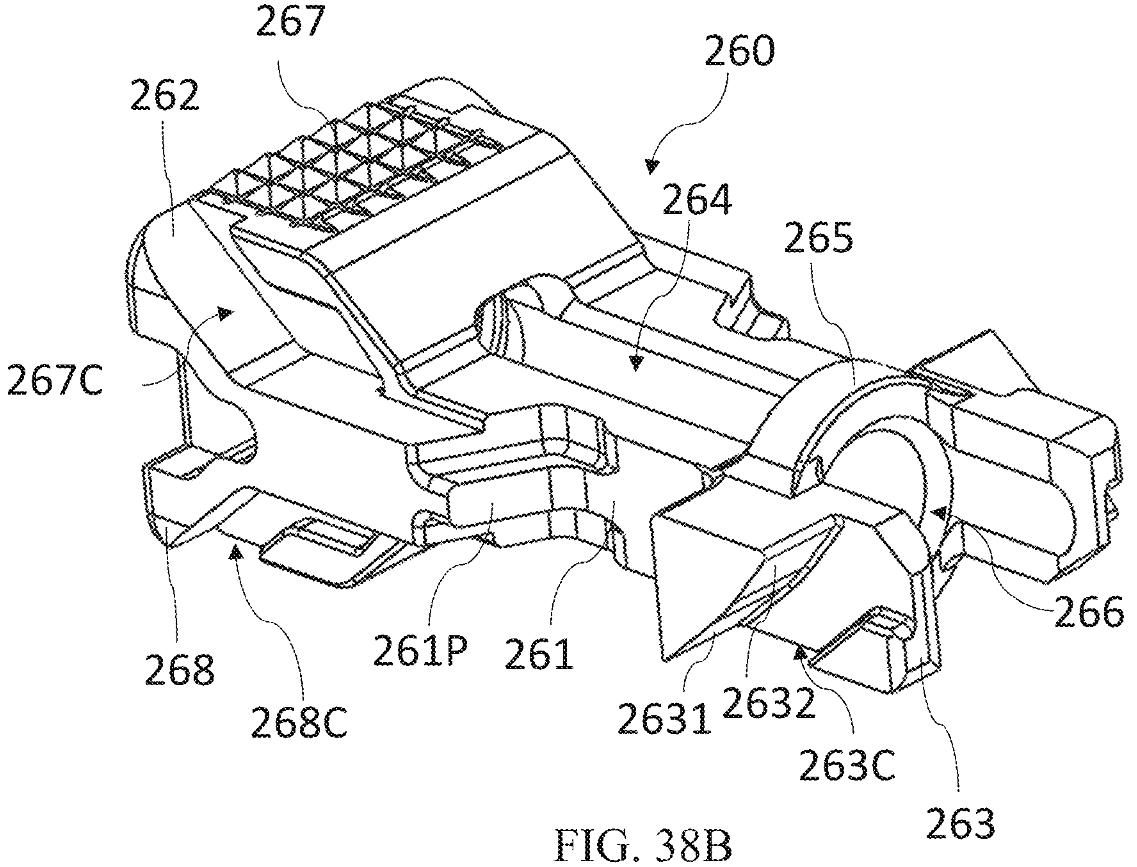

FIGS. 38A and 38B illustrate views of the proximal cage 260 from the expandable interbody implant of FIGS. 29 through 36. The proximal cage 260 includes a body 261 extending between a proximal end 262 and a distal end 263, and having a top surface 267 and a bottom surface 268. The proximal end 262 defines an opening 269 for receiving a driver or handle, such as the driver 95 in FIGS. 26A through 27. The distal end 263 may be open or substantially open to receive the proximal extension 218 of the distal cage 210 in the third position.

Disposed near the distal end 263 is the stop 265 which mechanically stops proximal motion of the distal cage 210 when the proximal extension 218 of the distal cage 210 is received within the distal end 263 of the proximal cage 260. The stop 265 defines an opening 266 to receive a proximal end 274 of the drive screw 272. Defined in the distal end 263 are channels 263C that engage with the hook portion 237 of the distal ramp 233. For example, as the top distal ramp 233A (or the bottom distal ramp 233B) slides along the distal cage 210, the hook portion 237A starts to engage the channel 263C. As the top distal ramp 233A (or the bottom distal ramp 233B) continues to slide along the distal cage 210, the hook portion 237A slides within the channel 263C, thereby facilitating the vertical expansion. This coupling of the hook portion 237A and the channel 263C stabilizes the expandable interbody implant 2100 during the cranial-caudal expansion 2106. Specifically, the projection 237P engages and slides within the channel 263C. The channel 263C may include a first portion 2631 that is more horizontal and a second portion 2632 that is more vertical than the first portion 2631. This transition from the first, horizontal portion 2631 to the second, vertical portion 2632 ensures strong engagement between the projection 237P and the channel 263C, thereby stabilizing the expandable interbody implant 2100.

The proximal cage 260 also defines one or more channels in the proximal end, 262. As shown in the configuration of FIGS. 28A-B, top channels 267C' and bottom channels 268C' are provided at the proximal end 262 of the proximal cage 260. Channels 267C and 268C facilitate translation of the top proximal ramp 247A and the bottom proximal ramp 247B, respectively, along the proximal cage 260. Channels 267C and 268C may also have a first portion that is more horizontal and a second portion that is more vertical than the first portion, facilitating engagement and stabilization as the expandable interbody implant 2100 transitions from a collapsed configuration to an expanded configuration.

The body 261 of the proximal cage 260 also defines a channel 264 extending between the stop 265, the opening 266, the proximal end 262, and the opening 269. The body 261 also includes projections 261P that engage the channel 229 defined in the proximal extensions 226A and 226B of the top and bottom expandable assemblies 220A and 220B.

FIGS. 39A and 39B illustrate views of the distal pivot or ramp 233 (either 233A or 233B) from the expandable interbody implant 2100 of FIGS. 29 through 36. As discussed, the top distal ramp 233A is identical to the bottom distal ramp 233B. Accordingly, the illustrated distal ramp 233 in FIGS. 39A and 39B will be discussed generally and it is to be understood that the features discussed in FIGS. 39A and 39B apply to both the top distal ramp 233A and the bottom distal ramp 233B. The distal ramp 233 includes a body 234 having an outer surface 235 and a ramped inner surface 244 opposite the outer surface 235. The outer surface 235 includes a first projection 245 for interfacing with the distal ends 230A, 230B of the second endplates 222A, 222B and a second projection 246 for interfacing with the distal ends 230A, 230B of the first endplates 221A, 221B. The body 234 includes a first sidewall 236 and a second sidewall 242 opposite the first sidewall 236.

The outer surface 235, the first sidewall 236, and the second sidewall 242 together define an open inner surface 243. The open inner surface 243 includes the ramped surface 244, which slides against the distal cage 210 when the interbody 2100 is expanded in the lordotic configuration 2104, and the cranial-caudal configuration 2106. The ramped surface 244 slides along the ramps 214 or 216 of the distal cage 210, as appropriate (i.e., a bottom ramped surface 244 of the bottom distal ramp 233B slides along the bottom ramp 216 of the distal cage 210). The first sidewall 236 includes the hook portion 237.

The ramped surface 244 includes a straight portion S and a curved portion C. The curved portion C of the ramped surface 244 facilitates engagement of the distal cage 210, such that the ramped surface 244 may slide along the distal cage 210. As the ramped surface 244 slides along the distal cage 210, the straight portion S will become parallel to a surface of the distal cage 210.

The hook portion 237 provides an interlock between the top expandable assembly 220A and the bottom expandable assembly 220B. Specifically, the hook portion 237A of the top distal ramp 233A interlocks with the first bottom endplate 221B (the channel 232B at the distal end 230B) of the bottom expandable assembly 220B. Simultaneously, the hook portion 237B of the bottom distal ramp 233B interlocks with the first top endplate 221A (the channel 232A at the distal end 230A) of the top expandable assembly 220A. Until the hook portion clears the channels, the interbody 2100 can only expand in the medial-lateral direction (i.e., in width).

The first sidewall 236 and the second sidewall 242 each also include a ramped portion 239. Specifically, the first sidewall 236 and the second sidewall 242 each extend from the outer surface 234 to an edge 238, which includes the ramp portion 239. The ramp portion 239 includes a straight portion 240 and a curved portion 241. The curved portion 241 of the ramp portion 239 facilitates engagement of the slots 215 or 217 of the distal cage 210, such that the ramp portion 239 may slide within the slots 215 or 217.

FIGS. 40A and 40B illustrate views of the proximal pivot or ramp 247 (either 247A or 247B) from the expandable interbody implant 2100 of FIGS. 29 through 36. As discussed, the top proximal ramp 247A is identical to the bottom proximal ramp 247B. Accordingly, the illustrated proximal ramp 247 in FIGS. 40A and 40B will be discussed generally and it is to be understood that the features discussed in FIGS. 40A and 40B apply to both the top proximal ramp 247A and the bottom proximal ramp 247B. The proximal ramp 247 includes a body 248 having an outer surface 249 and a ramped inner surface 253 opposite the outer surface 249. The outer surface 249 includes a first projection 250 for interfacing with the proximal ends 224A, 224B of the second endplates 222A, 222B and a second projection 251 for interfacing with the proximal ends 224A, 224B of the first endplates 221A, 221B.

The body 248 also includes lateral wings 252, which include a ramp portion 254. The ramped bottom surface 254 slides along a surface (e.g., a top surface 267 or a bottom surface 268) of the proximal cage 260. The ramp portion 254 of the lateral wings 252 also slides along the proximal cage 260.

Figure 41A:
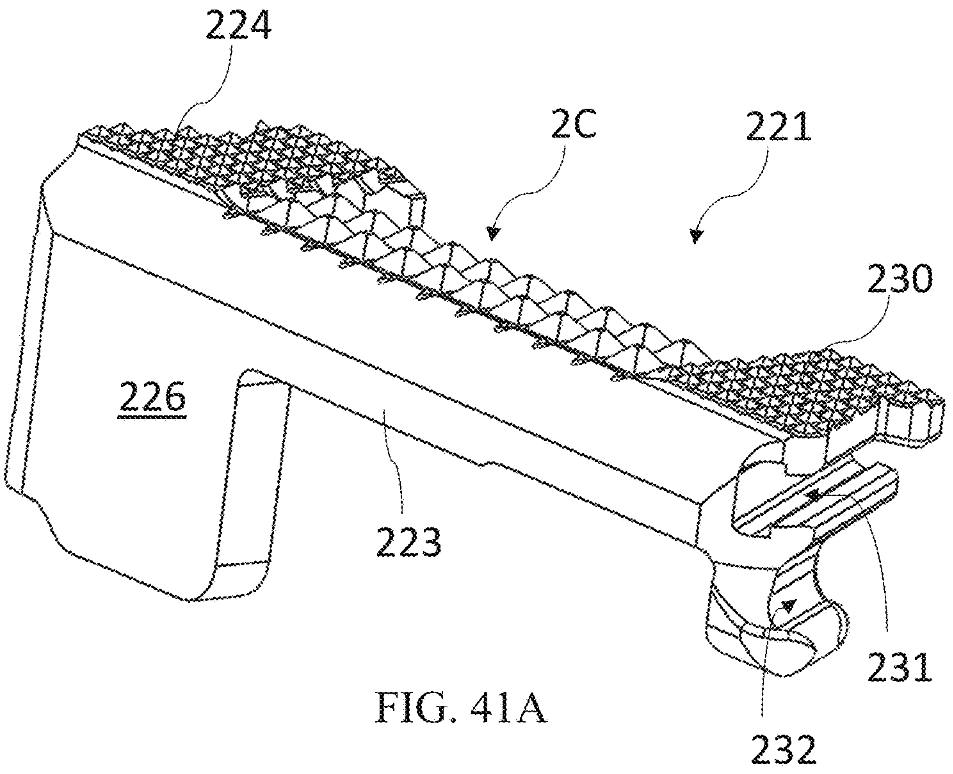
FIG. 41A and FIG. 41B illustrate perspective views of the first endplate of the top or bottom expandable assembly from the expandable interbody implant of FIGS. 29 through 36, the first endplate including a channel that locks with a hook portion of the distal pivot or ramp from FIGS. 39A and 39B.
Figure 41B:
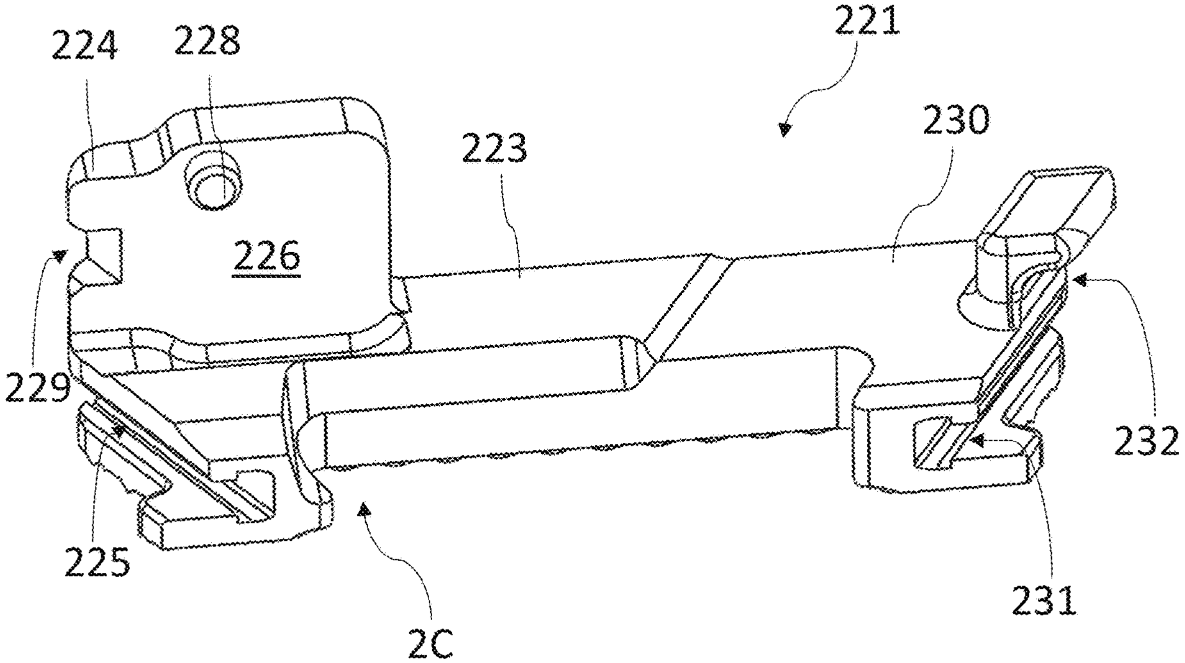

FIG. 41A and FIG. 41B illustrate views of the first endplate 221 of the top (221A) or bottom (221B) expandable assembly from the expandable interbody implant 2100 of FIGS. 29 through 36, the first endplate 221 including a channel 232 that locks with a hook portion 237 of the distal pivot or ramp 233 from FIGS. 39A and 39B. Similar to the distal ramp 233 and the proximal ramp 247, the first top endplate 221A is identical to the first bottom endplate 221B. Accordingly, the illustrated first endplate 221 in FIGS. 41A and 41B will be discussed generally and it is to be understood that the features discussed in FIGS. 41A and 41B apply to both the first top endplate 221A and the first bottom endplate 221B.

The first endplate 221 includes a body 223 extending between a proximal end 224 and a distal end 230. Defined in the proximal end 224 is a channel 225 for engaging and sliding along the second projection 251 of the proximal ramp 247. The proximal end 224 also includes a proximal extension 226 for mating and mechanically engaging a proximal extension 226 of a corresponding second endplate 222. The proximal extension 226 of the first endplate 221 includes a protrusion 228 that mechanically engages a groove 227 defined in the proximal extension 226 of the second endplate 222. The proximal extension 226 also defines a cut-out or channel 229 that mates and overlaps with the cut-out 229 in a corresponding second endplate 222. The joined cut-outs 229 receive the projection 261P of the proximal cage 260 when the implant 2100 is in the collapsed configuration.

The first endplate 221 includes or defines a channel 232 at the distal end 230 that locks with the hook portion 237 of the distal pivot or ramp 233 from FIGS. 39A and 39B. The hook portion 237 must clear the channel 232 to allow the implant 2100 to expand in the lordotic configuration 2104 and the cranial-caudal configuration 2106. The distal end 230 also includes or defines a channel 231 for engaging and sliding along the second projection 246 of the distal ramp 233. The first endplate 221 and/or the body 223 may also define a cut-out C in a medial edge, thereby reducing an amount of material required to form the first endplate 221.

Figure 42A:
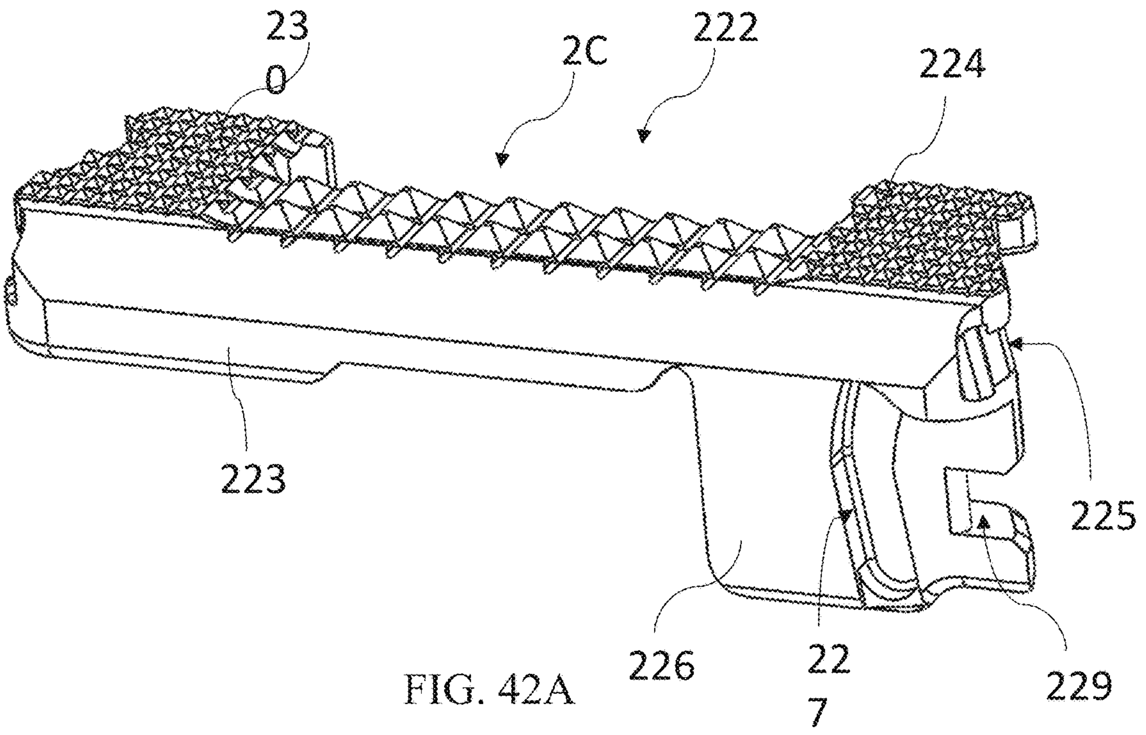
FIG. 42A illustrates a distal, perspective view
Figure 42B:
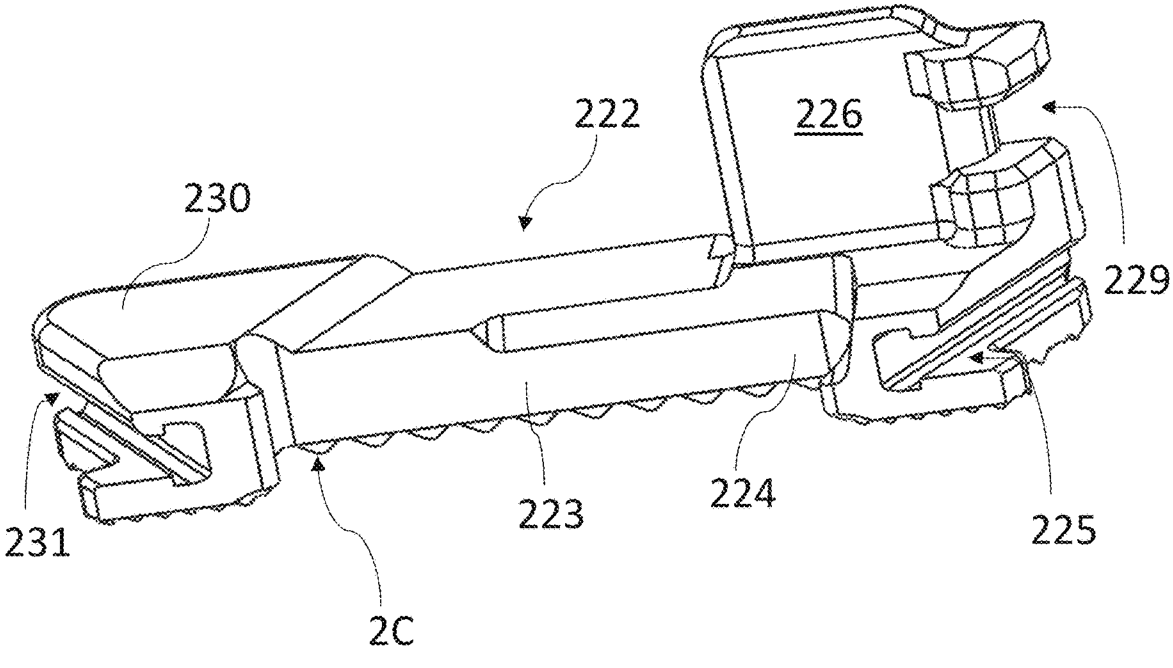
FIG. 42B illustrates a proximal perspective view of the second endplate of the top or bottom expandable assembly from the expandable interbody implant of FIGS. 29 through 36, the second endplate including a groove that engages with a projection of the first endplate of FIGS. 41A and 41B.

FIGS. 42A and 42B illustrate views of the second endplate 222 of the top (222A) or bottom (222B) expandable assembly 220A, 220B from the expandable interbody implant 2100 of FIGS. 29 through 36, the second endplate 222 including a groove 227 that engages with a projection 228 of the first endplate 221 of FIGS. 41A and 41B. As with the first endplate 221, the second top endplate 222A is identical to the second bottom endplate 222B. Accordingly, the illustrated second endplate 222 in FIGS. 42A and 42B will be discussed generally and it is to be understood that the features discussed in FIGS. 42A and 42B apply to both the second top endplate 222A and the second bottom endplate 222B. The second endplate 222 is also substantially identical to the first endplate 221, so like features will be labelled with like reference numbers.

The second endplate 222 includes a body 223 extending between a proximal end 224 and a distal end 230. Defined in the proximal end 224 is a channel 225 for engaging and sliding along the first projection 250 of the proximal ramp 247. The proximal end 224 also includes a proximal extension 226 for mating and mechanically engaging a proximal extension 226 of a corresponding first endplate 221. The proximal extension 226 of the second endplate 222 defines a groove 227 in which the projection 228 of the first endplate 221 slides and moves.

Referring briefly to FIGS. 22A and 22B, illustrating channel 27 to which the channel 227 is similar, the channel 227 is shaped to guide, first, the lordotic or angular movement and then, second, the cranial-caudal or height movement. Specifically, the shape of the groove 27 includes a curved section 27C then a substantially straight section 27S to facilitate these movements. The curved section 27C allows the top expandable assembly 220A and the bottom expandable assembly 220B to be angularly disposed in the lordotic direction. Then, the straight section 27S allows the top expandable assembly 220A and the bottom expandable assembly 220B to be vertically moved away from each other in the cranial-caudal direction.

The proximal extension 226 also defines a cut-out 229 that mates and overlaps with the cut-out 229 of the corresponding first endplate 221. The joined cut-outs 229 receive the projection 261P of the proximal cage 260 when the implant 2100 is in the collapsed configuration.

The distal end 230 of the second endplate 222 includes or defines a channel 231 for engaging and sliding along the first projection 245 of the distal ramp 233. The second endplate 222 and/or the body 223 may also define a cut-out 2C in a medial edge, thereby reducing an amount of material required to form the second endplate 222.

Figure 43A:
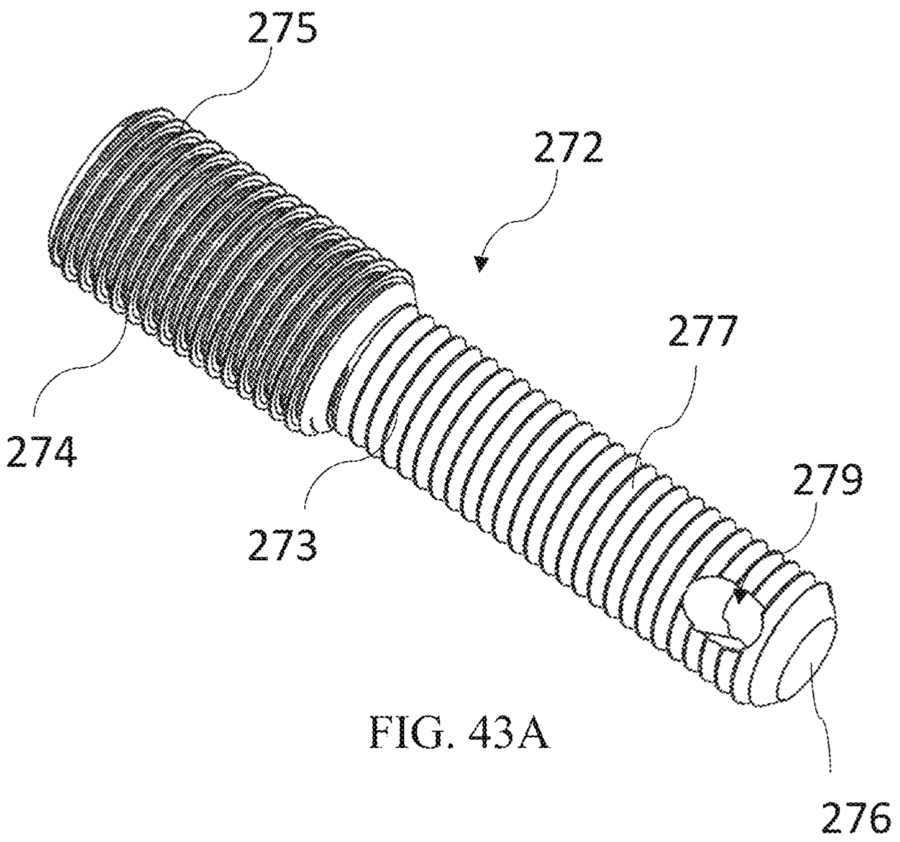
FIG. 43A illustrates a distal perspective view and FIG. 43B illustrates a proximal perspective view of the drive screw from the expandable interbody implant of FIGS. 29 through 36.
Figure 43B:
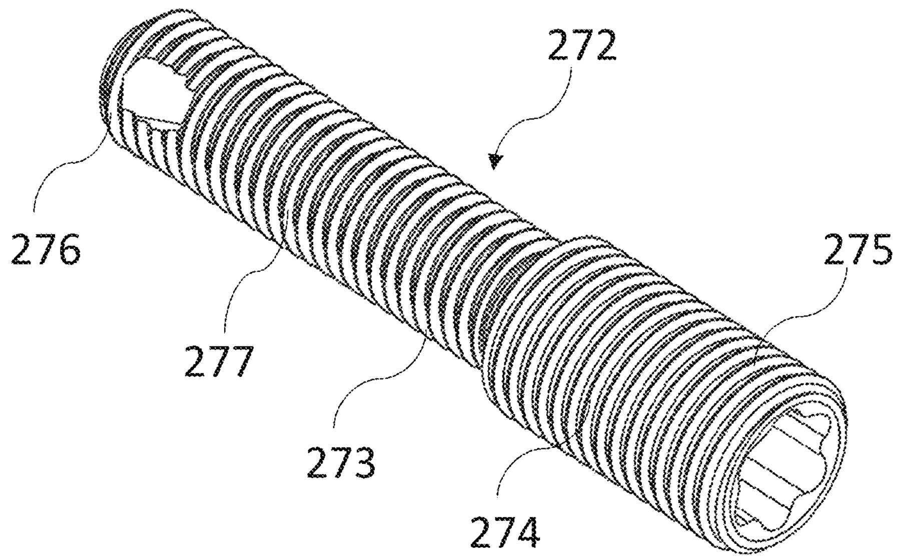
Figure 44A:
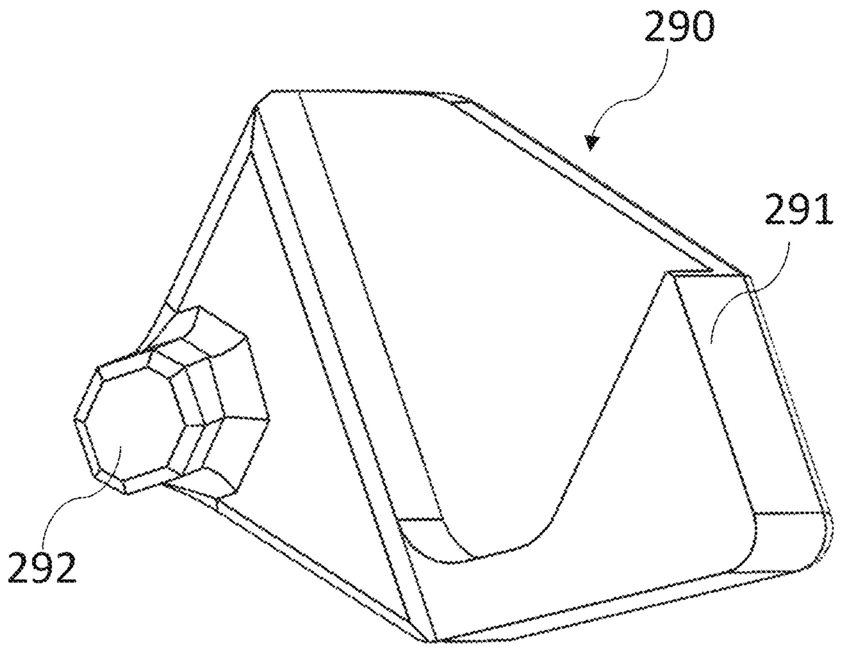
FIG. 44A illustrates a perspective, inside view
Figure 44B:
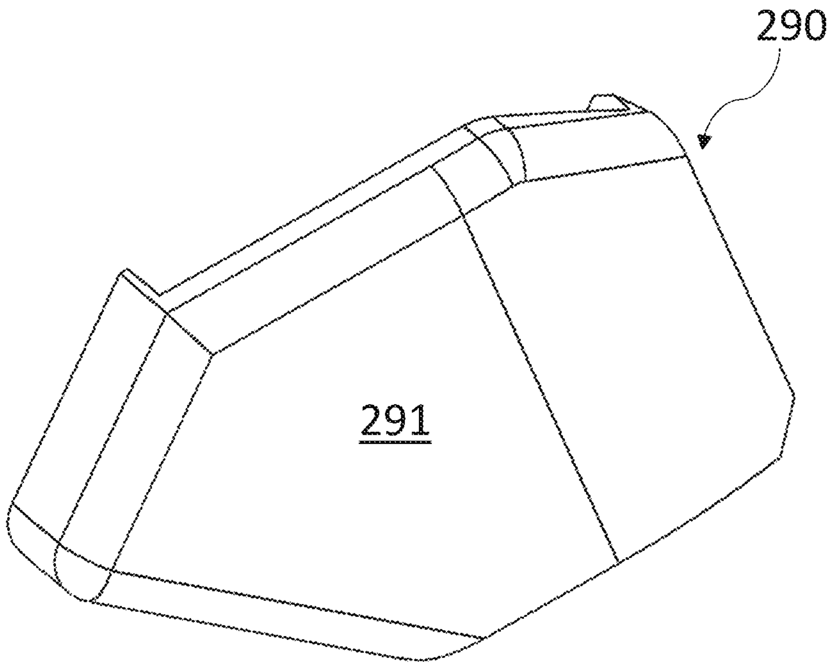
FIG. 44B illustrates a perspective view of a distal cage cap to cover a portion of the distal cage of FIGS. 37A and 37B.

FIGS. 43A and 43B illustrate views of the drive screw 272 from the expandable interbody implant 2100 of FIGS. 29 through 36. The drive screw 272 includes a body 273 extending between a proximal end 274 and a distal end 276.

The proximal end 274 includes threading 275 that corresponds to threading of the proximal cage 260. The distal end 276 includes threading 277 that corresponds to threading of the distal cage 210. The threadings 275 and 277 may be different from each other. Driving of the drive screw 272 causes the distal cage 210 to be translated proximally towards the proximal cage 260, thereby causing the implant 2100 to expand firstly in the medial-lateral direction, secondly in the lordotic direction, and thirdly in the cranial-caudal direction. Defined near the distal end 276, the drive screw 272 may include a void or bore 279 for receiving an insert 278 (e.g., a PEEK insert, etc.) that provides torsional resistance to the drive screw 272 within the expandable interbody implant 2100.

FIGS. 44A and 44B illustrate views of a distal cage cap 290 to cover a portion of the distal cage 210 of FIGS. 37A and 37B. The distal cage cap 290 includes a body 291 and a projection 292. The projection 292 is for engaging a portion of the distal cage 210, thereby improving a connection between the distal cage cap 290 and the distal cage 210.

EMBODIMENTS

The following embodiments are provided as examples only of specific configurations, materials, arrangements, etc. contemplated by the authors of this disclosure:

Embodiment 1. An expandable implant for use in a surgical procedure, the expandable implant comprising:

- a distal cage;
- a proximal cage opposite the distal cage;
- a drive screw connecting the distal cage to the proximal cage;
- a top distal pivot slidable along a top surface of the distal cage;
- a bottom distal pivot slidable along a bottom surface of the distal cage, the bottom surface opposite the top surface;
- a top proximal pivot slidable along a top surface of the proximal cage;
- a bottom proximal pivot slidable along a bottom surface of the proximal cage, the bottom surface opposite the top surface;
- a top pair of endplates, each top endplate having a proximal end slidable along a surface of the top proximal pivot,
  - the proximal end defining a proximal channel for slidably receiving a projection of the top proximal pivot,
- each top endplate also having a distal end slidable along a surface of the top distal pivot, the distal end defining a distal channel for slidably receiving a projection of the top distal pivot,
- a first endplate of the top pair of endplates connected to a hook portion of the bottom distal pivot when the expandable implant is in a collapsed state; and
- a bottom pair of endplates, each endplate having a proximal end slidable along a surface of the bottom proximal pivot,
  - the proximal end defining a proximal channel for slidably receiving a projection of the bottom proximal pivot,
- each bottom endplate also having a distal end slidable along a surface of the bottom distal pivot, the distal end defining a distal channel for slidably receiving a projection of the bottom distal pivot,
- a first endplate of the bottom pair of endplates connected to a hook portion of the top distal pivot when the expandable implant is in the collapsed state; and
- wherein the expandable implant is expandable firstly in a medial-lateral direction, secondly in a lordotic direction, and thirdly a cranial-caudal direction.

Embodiment 2. The expandable implant of claim 1, wherein the distal cage comprises:

- a body defining a bore for engaging a distal end of the drive screw and having the top surface and the bottom surface opposite the top surface, and
- wherein the top surface has a top ramp and a top slot for engaging the top distal pivot and the bottom surface has a bottom ramp and a bottom slot for engaging the bottom distal pivot.

Embodiment 3. The expandable implant of claim 2, wherein the body has a substantially diamond shape.

Embodiment 4. The expandable implant of either one of claim 2 or 3, wherein the top surface tapers toward the bottom surface, the top surface tapering in a direction opposite the top ramp.

Embodiment 5. The expandable implant of any one of claim 2, 3, or 4, wherein the bore comprises a first threading to match a distal threading of the drive screw.

Embodiment 6. The expandable implant of any one of claim 1, 2, 3, 4, or 5, wherein the top distal pivot comprises a body having:

- a top surface;
- a first sidewall extending from the top surface and having the hook portion for engaging the distal end of the first endplate of the bottom pair of endplates, a bottom edge of the first sidewall having an edge ramp for slidably engaging the top surface of the distal cage,
- the edge ramp comprising a straight portion and a curved portion, the straight portion of the edge ramp parallel to the top surface of the distal cage when the expandable implant is expanded in the lordotic and cranial-caudal directions; and
- a second sidewall extending from the top surface opposite the first sidewall,
- the top surface, the first sidewall, and the second sidewall together defining an open bottom opposite the top surface,
- the first and second sidewalls engaging a slot defined by the top surface of the distal cage, and
- the open bottom having a ramp slidable along the top surface of the distal cage.

Embodiment 7. The expandable implant of claim 6, wherein the bottom distal pivot is identical to the top distal pivot and symmetrically oriented about a longitudinal axis of the expandable implant.

Embodiment 8. The expandable implant of any one of claim 1, 2, 3, 4, 5, 6, or 7, wherein the top pair of endplates comprises the first endplate and a second endplate, each endplate comprising:

- a body extending between the proximal end and the distal end;
- an extension at the proximal end for engaging with the proximal end of each endplate of the bottom pair of endplates; and
- a cut-out defined in a medial edge of the body,
- the distal end of the body defining a distal slot to slidably engage the top surface of the distal pivot, and
- the proximal end of the body defining the proximal channel to slidably receive the projection of the top proximal pivot, the distal end of the body defining the distal channel to slidably receive the projection of the top distal pivot, and each endplate movable in the medial-lateral direction.

Embodiment 9. The expandable implant of claim 8, wherein the bottom pair of endplates comprises the first endplate and a second endplate, each of the endplates being identical to the top endplates and being diagonally symmetrically arranged about the longitudinal axis of the expandable implant.

Embodiment 10. The expandable implant of any one of claim 1, 2, 3, 4, 5, 6, 7, 8, or 9, wherein the top proximal pivot comprises:

a body having the projection for slidably engaging the proximal ends of each endplate of the top pair of endplates;

lateral wings extending from the body, the lateral wings slidably engaging a portion of the top surface of the proximal cage; and a ramp on an underside of the body, the ramp for sliding along the top surface of the proximal cage.

Embodiment 11. The expandable implant of claim 10, wherein the bottom proximal pivot is identical to the top proximal pivot and symmetrically oriented about the longitudinal axis of the expandable implant.

Embodiment 12. An expandable implant for use in a surgical procedure, the expandable implant comprising:

a distal cage;

a proximal cage opposite the distal cage;

a drive screw connecting the distal cage to the proximal cage;

a top expandable assembly, the top expandable assembly having:

a distal portion in communication with a top surface of the distal cage, a proximal portion in communication with a top surface of the proximal cage, a first top endplate having a distal end in connection with the distal portion and a proximal end in connection with the proximal portion, and a second top endplate adjacent to the first endplate, the second endplate having a distal end in connection with the distal portion and a proximal end in connection with the proximal portion; and a bottom expandable assembly, a distal portion of the bottom expandable assembly in communication with a bottom surface of the distal cage and a proximal portion of the bottom expandable assembly in communication with a bottom surface of the proximal cage, the bottom surface of the distal cage opposite the top surface and the bottom surface of the proximal cage opposite the top surface, the distal portion of the top expandable assembly comprising a hook for mechanically connecting to a distal end of a first bottom endplate of the bottom expandable assembly, and the distal portion of the bottom expandable assembly comprising a hook for mechanically connecting to the distal end of the second top endplate of the top expandable assembly, the expandable first in a medial-lateral direction, second in a lordotic direction, and third in a cranial-caudal direction.

Embodiment 13. The expandable implant of claim 12, wherein the bottom expandable assembly is identical to the top expandable assembly and disposed diagonally symmetrical about the longitudinal axis of the expandable implant.

Embodiment 14. The expandable implant of either claim 12 or 13, wherein a proximal extension of the first bottom endplate is mechanically engaged with a proximal extension of the first top endplate, such that the first bottom endplate and the first top endplate move together in the medial-lateral direction.

Embodiment 15. The expandable implant of any one of claim 12, 13, or 14, wherein a proximal extension of a second bottom endplate is mechanically engaged with a proximal extension of the second top endplate.

Embodiment 16. An expandable interbody for use in a surgical procedure, the expandable interbody comprising:

a distal cage;

a proximal cage in mechanical communication with the distal cage;

a top distal ramp slidable along a top surface of the distal cage;

a bottom distal ramp slidable along a bottom surface of the distal cage, the bottom surface opposite the top surface, the top and bottom distal ramps facilitating expansion of the expandable interbody in a lordotic direction and a cranial-caudal direction;

a top proximal ramp slidable along a top surface of the proximal cage;

a bottom proximal ramp slidable along a bottom surface of the proximal cage, the bottom surface opposite the top surface, the top and bottom proximal ramps facilitating expansion of the expandable interbody in the cranial-caudal direction; and a plurality of endplates in mechanical connection with the top distal ramp, the bottom distal ramp, the top proximal ramp, and the bottom proximal ramp, the plurality of endplates expandable in a medial-lateral direction, the expandable interbody being diagonally symmetrical about a longitudinal axis of the expandable interbody.

Embodiment 17. The expandable interbody of claim 16, further comprising a drive screw mechanically connecting the distal cage and the proximal cage.

Embodiment 18. The expandable interbody of either one of claim 16 or 17, wherein the plurality of endplates comprises four (4) endplates, each endplate comprising:

a body extending between a proximal end and a distal end;

an extension at the proximal end for engaging with the proximal end of each endplate of a bottom pair of endplates;

a cut-out defined in a medial edge of the body.

Embodiment 19. A method of expanding an expandable interbody, the method comprising:

first translating a distal cage proximally towards a proximal cage to a first position to cause a plurality of endplates to expand in a medial-lateral direction relative to a longitudinal axis of the expandable interbody;

second translating the distal cage proximally towards the proximal cage from the first position to a second position different than the first position, such that a locking hook of a top distal ramp clears a channel defined in a distal end of a first bottom endplate, and such that a locking hook of a bottom distal ramp clears a channel defined in a distal end of a first top endplate;

the second translating causing:

the top distal ramp to slide along the distal cage to achieve a desired lordosis;

a first projection of the proximal cage to clear a channel defined in a proximal end of the first bottom endplate, and a second projection of the proximal cage to clear a channel defined in a proximal end of a second bottom endplate;

third translating the distal cage proximally towards the proximal cage from the second position to a third position, a bore of the distal cage abutting a distal face of the proximal cage, the distal face of the proximal cage preventing further proximal translation of the distal cage; and the third translating causing a top proximal ramp to slide along the proximal cage in a cranial-caudal direction, such that a protrusion of the first bottom endplate slides within a groove defined in a proximal extension of a second top endplate, thereby allowing the first bottom endplate to vertically separate from the second top endplate.

Embodiment 20. The method of claim 19, wherein the first translating comprises:

engaging internal threading of the distal cage with a distal end of a drive screw;

engaging internal threading of the proximal cage with a proximal end of the drive screw, the internal threading of the proximal cage being different than the internal threading of the distal cage; and actuating the drive screw in a first direction, such that the distal cage is translated proximally towards the proximal cage.

Embodiment 21. The method of either one of claim 19 or 20, wherein firstly expanding a plurality of endplates in a medial-lateral direction comprises:

sliding a proximal channel defined in the proximal end of the first bottom endplate along a projection of a bottom proximal ramp;

sliding a proximal channel defined in a proximal end of a second bottom endplate along a projection of the bottom proximal ramp;

sliding a proximal channel defined in a proximal end of the first top endplate along a projection of the top proximal ramp; and sliding a proximal channel defined in a proximal end of the second top endplate along a projection of the top proximal ramp, wherein the first bottom endplate and the second bottom endplate move away from each other, and wherein the first top endplate and the second top endplate move away from each other.

Embodiment 22. The method of any one of claim 19, 20, or 21, wherein the second translation comprises engaging a ramp of the distal cage with a ramp portion of the top distal ramp, the ramp portion having opposing edges, each opposing edge comprising a straight portion and a curved portion at a distal end of the opposing edge, the curved portion abutting the distal cage and the straight portion not abutting the distal cage;

driving the distal cage proximally towards the proximal cage, such that the straight portion of the opposing edges of the ramp portion abuts the distal cage and the straight portion of the opposing edges is parallel to the ramp of the distal cage; and moving the straight portion of the opposing edges along the distal cage, until the curved portion of the opposing edges extends beyond the distal cage, the straight portion of the opposing edges remaining parallel to the ramp of the distal cage.

Embodiment 23. An expandable implant for use in a surgical procedure, the expandable implant comprising:

a distal cage;

a proximal cage opposite the distal cage;

a drive screw connecting the distal cage to the proximal cage;

a top distal pivot slidable along a top surface of the distal cage;

a bottom distal pivot slidable along a bottom surface of the distal cage, the top and bottom distal pivots being structurally identical to each other;

a top proximal pivot slidable along a top surface of the proximal cage;

a bottom proximal pivot slidable along a bottom surface of the proximal cage, the top and bottom proximal pivots being structurally identical to each other;

a pair of top endplates, each top endplate having a proximal end slidable along a surface of the top proximal pivot and a distal end slidable along a surface of the top distal pivot;

a pair of bottom endplates, each bottom endplate having a proximal end slidable along a surface of the bottom proximal pivot and a distal end slidable along a surface of the bottom distal pivot;

wherein a first top endplate of the pair of top endplates is structurally identical to a first bottom endplate of the pair of bottom endplates, and a second top endplate of the pair of top endplates is structurally identical to a second bottom endplate of the pair of bottom endplates.

Embodiment 24. The expandable implant of embodiment 23, wherein each distal pivot comprises a hook portion configured to engage one of the pair of top and bottom endplates, respectively, when the implant is in an unexpanded configuration.

Embodiment 25. The expandable implant of embodiment 24, wherein the hook portion is further configured to engage a channel in a distal end of the proximal cage when the implant is in a vertically expanded configuration.

Embodiment 26. The expandable implant of any one of embodiments 23, 24, or 25, wherein the rotation of the drive screw causes the distal cage to translate proximally toward the proximal cage expanding the implant first laterally, second lordotically, and third vertically.

Embodiment 27. The expandable implant of any one of embodiments 23, 24, 25, or 26, wherein each of the top and bottom endplates comprises an extension containing a channel configured to slide along respective ridges of the proximal cage during lateral expansion.

Embodiment 28. The expandable implant of embodiment 27, wherein the ridges sliding along the channels of the top and bottom endplates prevents the implant from expanding lordotically or vertically.

Embodiment 29. The expandable implant of any one of embodiments 24, 25, 26, 27, or 28, wherein engagement of one of the pair of top endplates with the hook portion of the distal pivot constrains the expansion of the top endplates to only lateral expansion.

Embodiment 30. An expandable implant for use in a surgical procedure, the expandable implant comprising:

a distal cage;

a proximal cage opposite the distal cage;

a drive screw connecting the distal cage to the proximal cage;

top and bottom expansion assemblies, each in sliding engagement with both the distal and proximal cages;

wherein rotation of the drive screw in a first direction causes the distal cage to translate along the drive screw proximally toward the proximal cage expanding the implant first laterally, second lordotically, and third vertically; and wherein, during lateral expansion, the top and bottom expansion assemblies are slidingly engaged to each other.

Embodiment 31. The expandable implant of embodiment 30, wherein the sliding engagement between the top and bottom expansion assemblies during lateral expansion prevents the top and bottom expansion assemblies from expanding lordotically and vertically.

Embodiment 32. The expandable implant of either one of embodiment 30 or 31, wherein full lateral expansion is required to achieve disengagement of the top and bottom expansion assemblies from each other.

Embodiment 33. The expandable implant of any one of embodiments 30, 31, or 32, wherein the top and bottom expansion assemblies are structurally inverse images of each other across a diagonal plane.

Additional Terms and Definitions

While particular embodiments have been illustrated and described herein, it should be understood that various other changes and modifications may be made without departing from the spirit and scope of the claimed subject matter. Moreover, although various aspects of the claimed subject matter have been described herein, such aspects need not be utilized in combination. It should also be noted that some of the embodiments disclosed herein may have been disclosed in relation to an expandable interbody implant (e.g., an interbody for spine surgeries); however, other interbody implants (e.g., limb surgery, particular spine surgeries, etc.) are also contemplated.

In one embodiment, the terms "about" and "approximately" refer to numerical parameters within 10% of the indicated range. The terms "a," "an," "the," and similar referents used in the context of describing the embodiments of the present disclosure (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the embodiments of the present disclosure and does not pose a limitation on the scope of the present disclosure. No language in the specification should be construed as indicating any non-claimed element essential to the practice of the embodiments of the present disclosure.

Groupings of alternative elements or embodiments disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments are described herein, including the best mode known to the author(s) of this disclosure for carrying out the embodiments disclosed herein. Of course, variations on these described embodiments will become apparent to those of ordinary skill in the art upon reading the foregoing description. The author(s) expects skilled artisans to employ such variations as appropriate, and the author(s) intends for the embodiments of the present disclosure to be practiced otherwise than specifically described herein. Accordingly, this disclosure includes all modifications and equivalents of the subject matter recited in the claims appended hereto as permitted by applicable law. Moreover, any combination of the above-described elements in all possible variations thereof is encompassed by the present disclosure unless otherwise indicated herein or otherwise clearly contradicted by context.

Specific embodiments disclosed herein may be further limited in the claims using consisting of or consisting essentially of language. When used in the claims, whether as filed or added per amendment, the transition term "consisting of" excludes any element, step, or ingredient not specified in the claims. The transition term "consisting essentially of" limits the scope of a claim to the specified materials or steps and those that do not materially affect the basic and novel characteristic(s). Embodiments of this disclosure so claimed are inherently or expressly described and enabled herein.

Although this disclosure provides many specifics, these should not be construed as limiting the scope of any of the claims that follow, but merely as providing illustrations of some embodiments of elements and features of the disclosed subject matter. Other embodiments of the disclosed subject matter, and of their elements and features, may be devised which do not depart from the spirit or scope of any of the claims. Features from different embodiments may be employed in combination. Accordingly, the scope of each claim is limited only by its plain language and the legal equivalents thereto.

What is claimed:

1. An expandable implant for use in a surgical procedure, the expandable implant comprising:

a distal cage;

a proximal cage opposite the distal cage;

a drive screw connecting the distal cage to the proximal cage;

a top distal pivot slidable along a top surface of the distal cage;

a bottom distal pivot slidable along a bottom surface of the distal cage, the bottom surface opposite the top surface;

a top proximal pivot slidable along a top surface of the proximal cage;

a bottom proximal pivot slidable along a bottom surface of the proximal cage, the bottom surface opposite the top surface;

a top pair of endplates, each top endplate having a proximal end slidable along a surface of the top proximal pivot, the proximal end defining a proximal channel for slidably receiving a projection of the top proximal pivot, each top endplate also having a distal end slidable along a surface of the top distal pivot, the distal end defining a distal channel for slidably receiving a projection of the top distal pivot, a first endplate of the top pair of endplates connected to a hook portion of the bottom distal pivot when the expandable implant is in a collapsed state; and a bottom pair of endplates, each endplate having a proximal end slidable along a surface of the bottom proximal pivot, the proximal end defining a proximal channel for slidably receiving a projection of the bottom proximal pivot, each bottom endplate also having a distal end slidable along a surface of the bottom distal pivot, the distal end defining a distal channel for slidably receiving a projection of the bottom distal pivot, a first endplate of the bottom pair of endplates connected to a hook portion of the top distal pivot when the expandable implant is in the collapsed state; and wherein the expandable implant is expandable firstly in a medial-lateral direction, secondly in a lordotic direction, and thirdly a cranial-caudal direction.

2. The expandable implant of claim 1, wherein the distal cage comprises:

a body defining a bore for engaging a distal end of the drive screw and having the top surface and the bottom surface opposite the top surface, and wherein the top surface has a top ramp and a top slot for engaging the top distal pivot and the bottom surface has a bottom ramp and a bottom slot for engaging the bottom distal pivot.

3. The expandable implant of claim 2, wherein the body has a substantially diamond shape.

4. The expandable implant of claim 2, wherein the top surface tapers toward the bottom surface, the top surface tapering in a direction opposite the top ramp.

5. The expandable implant of claim 2, wherein the bore comprises a first threading to match a distal threading of the drive screw.

6. The expandable implant of claim 1, wherein the top distal pivot comprises a body having:

a top surface;

a first sidewall extending from the top surface and having the hook portion for engaging the distal end of the first endplate of the bottom pair of endplates, a bottom edge of the first sidewall having an edge ramp for slidably engaging the top surface of the distal cage, the edge ramp comprising a straight portion and a curved portion, the straight portion of the edge ramp parallel to the top surface of the distal cage when the expandable implant is expanded in the lordotic and cranial-caudal directions; and a second sidewall extending from the top surface opposite the first sidewall, the top surface, the first sidewall, and the second sidewall together defining an open bottom opposite the top surface, the first and second sidewalls engaging a slot defined by the top surface of the distal cage, and the open bottom having a ramp slidable along the top surface of the distal cage.

7. The expandable implant of claim 6, wherein the bottom distal pivot is identical to the top distal pivot and symmetrically oriented about a longitudinal axis of the expandable implant.

8. The expandable implant of claim 1, wherein the top pair of endplates comprises the first endplate and a second endplate, each endplate comprising:

a body extending between the proximal end and the distal end;

an extension at the proximal end for engaging with the proximal end of each endplate of the bottom pair of endplates; and a cut-out defined in a medial edge of the body, the distal end of the body defining a distal slot to slidably engage the top surface of the distal pivot, and the proximal end of the body defining the proximal channel to slidably receive the projection of the top proximal pivot, the distal end of the body defining the distal channel to slidably receive the projection of the top distal pivot, and each endplate moveable in the medial-lateral direction.

9. The expandable implant of claim 8, wherein the bottom pair of endplates comprises the first endplate and a second endplate, each of the endplates being identical to the top endplates and being diagonally symmetrically arranged about the longitudinal axis of the expandable implant.

10. The expandable implant of claim 1, wherein the top proximal pivot comprises:

a body having the projection for slidably engaging the proximal ends of each endplate of the top pair of endplates;

lateral wings extending from the body, the lateral wings slidably engaging a portion of the top surface of the proximal cage; and a ramp on an underside of the body, the ramp for sliding along the top surface of the proximal cage.

11. The expandable implant of claim 10, wherein the bottom proximal pivot is identical to the top proximal pivot and symmetrically oriented about the longitudinal axis of the expandable implant.

12. An expandable implant for use in a surgical procedure, the expandable implant comprising:

a distal cage;

a proximal cage opposite the distal cage;

a drive screw connecting the distal cage to the proximal cage;

a top expandable assembly, the top expandable assembly having:

a distal portion in communication with a top surface of the distal cage, a proximal portion in communication with a top surface of the proximal cage, a first top endplate having a distal end in connection with the distal portion and a proximal end in connection with the proximal portion, and a second top endplate adjacent to the first endplate, the second endplate having a distal end in connection with the distal portion and a proximal end in connection with the proximal portion; and a bottom expandable assembly, a distal portion of the bottom expandable assembly in communication with a bottom surface of the distal cage and a proximal portion of the bottom expandable assembly in communication with a bottom surface of the proximal cage, the bottom surface of the distal cage opposite the top surface and the bottom surface of the proximal cage opposite the top surface, the distal portion of the top expandable assembly comprising a hook for mechanically connecting to a distal end of a first bottom endplate of the bottom expandable assembly, and the distal portion of the bottom expandable assembly comprising a hook for mechanically connecting to the distal end of the second top endplate of the top expandable assembly, the expandable implant is expandable first in a medial-lateral direction, second in a lordotic direction, and third in a cranial-caudal direction.

13. The expandable implant of claim 12, wherein the bottom expandable assembly is identical to the top expandable assembly and disposed diagonally symmetrical about the longitudinal axis of the expandable implant.

14. The expandable implant of claim 12, wherein a proximal extension of the first bottom endplate is mechanically engaged with a proximal extension of the first top endplate, such that the first bottom endplate and the first top endplate move together in the medial-lateral direction.

15. The expandable implant of claim 12, wherein a proximal extension of a second bottom endplate is mechanically engaged with a proximal extension of the second top endplate.

16. An expandable interbody for use in a surgical procedure, the expandable interbody comprising:

a distal cage;

a proximal cage in mechanical communication with the distal cage;

a top distal ramp slidable along a top surface of the distal cage;

a bottom distal ramp slidable along a bottom surface of the distal cage, the bottom surface opposite the top surface, the top and bottom distal ramps facilitating expansion of the expandable interbody in a lordotic direction and a cranial-caudal direction;

a top proximal ramp slidable along a top surface of the proximal cage;

a bottom proximal ramp slidable along a bottom surface of the proximal cage, the bottom surface opposite the top surface, the top and bottom proximal ramps facilitating expansion of the expandable interbody in the cranial-caudal direction; and a plurality of endplates in mechanical connection with the top distal ramp, the bottom distal ramp, the top proximal ramp, and the bottom proximal ramp, the plurality of endplates expandable in a medial-lateral direction, the expandable interbody being diagonally symmetrical about a longitudinal axis of the expandable interbody.

17. The expandable interbody of claim 16, further comprising a drive screw mechanically connecting the distal cage and the proximal cage.

18. The expandable interbody of claim 16, wherein the plurality of endplates comprises four (4) endplates, each endplate comprising:

a body extending between a proximal end and a distal end;

an extension at the proximal end for engaging with the proximal end of each endplate of a bottom pair of endplates;

a cut-out defined in a medial edge of the body.

19. A method of expanding an expandable interbody, the method comprising:

first translating a distal cage proximally towards a proximal cage to a first position to cause a plurality of endplates to expand in a medial-lateral direction relative to a longitudinal axis of the expandable interbody;

second translating the distal cage proximally towards the proximal cage from the first position to a second position different than the first position, such that a locking hook of a top distal ramp clears a channel defined in a distal end of a first bottom endplate, and such that a locking hook of a bottom distal ramp clears a channel defined in a distal end of a first top endplate;

the second translating causing:

the top distal ramp to slide along the distal cage to achieve a desired lordosis;

a first projection of the proximal cage to clear a channel defined in a proximal end of the first bottom endplate, and a second projection of the proximal cage to clear a channel defined in a proximal end of a second bottom endplate;

third translating the distal cage proximally towards the proximal cage from the second position to a third position, a bore of the distal cage abutting a distal face of the proximal cage, the distal face of the proximal cage preventing further proximal translation of the distal cage; and the third translating causing a top proximal ramp to slide along the proximal cage in a cranial-caudal direction, such that a protrusion of the first bottom endplate slides within a groove defined in a proximal extension of a second top endplate, thereby allowing the first bottom endplate to vertically separate from the second top endplate.

20. The method of claim 19, wherein the first translating comprises:

engaging internal threading of the distal cage with a distal end of a drive screw;

engaging internal threading of the proximal cage with a proximal end of the drive screw, the internal threading of the proximal cage being different than the internal threading of the distal cage; and actuating the drive screw in a first direction, such that the distal cage is translated proximally towards the proximal cage.

21. The method of claim 19, wherein firstly expanding a plurality of endplates in a medial-lateral direction comprises:

sliding a proximal channel defined in the proximal end of the first bottom endplate along a projection of a bottom proximal ramp;

sliding a proximal channel defined in a proximal end of a second bottom endplate along a projection of the bottom proximal ramp;

sliding a proximal channel defined in a proximal end of the first top endplate along a projection of the top proximal ramp; and sliding a proximal channel defined in a proximal end of the second top endplate along a projection of the top proximal ramp, wherein the first bottom endplate and the second bottom endplate move away from each other, and wherein the first top endplate and the second top endplate move away from each other.

22. The method of claim 19, wherein the second translation comprises engaging a ramp of the distal cage with a ramp portion of the top distal ramp, the ramp portion having opposing edges, each opposing edge comprising a straight portion and a curved portion at a distal end of the opposing edge, the curved portion abutting the distal cage and the straight portion not abutting the distal cage;

driving the distal cage proximally towards the proximal cage, such that the straight portion of the opposing edges of the ramp portion abuts the distal cage and the straight portion of the opposing edges is parallel to the ramp of the distal cage; and moving the straight portion of the opposing edges along the distal cage, until the curved portion of the opposing edges extends beyond the distal cage, the straight portion of the opposing edges remaining parallel to the ramp of the distal cage.

* * * * *